United States Patent
Avkin-Nachum et al.

(10) Patent No.: US 10,144,928 B2
(45) Date of Patent: Dec. 4, 2018

(54) DOUBLE STRANDED OLIGONUCLEOTIDE COMPOUNDS COMPRISING POSITIONAL MODIFICATIONS

(71) Applicant: Quark Pharmaceuticals, Inc., Fremont, CA (US)

(72) Inventors: Sharon Avkin-Nachum, Nes Zionna (IL); Elena Feinstein, Rehovot (IL); Leonid Beigelman, San Mateo, CA (US)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 14/996,493

(22) Filed: Jan. 15, 2016

(65) Prior Publication Data

US 2016/0355805 A1    Dec. 8, 2016

Related U.S. Application Data

(63) Continuation of application No. 13/991,610, filed on Aug. 23, 2013, now abandoned.

(51) Int. Cl.
  *C07H 21/04*    (2006.01)
  *C12N 15/11*    (2006.01)

(52) U.S. Cl.
  CPC ........ *C12N 15/111* (2013.01); *C12N 2310/14* (2013.01); *C12N 2310/319* (2013.01); *C12N 2310/323* (2013.01); *C12N 2310/344* (2013.01); *C12N 2310/346* (2013.01); *C12N 2320/50* (2013.01); *C12N 2320/51* (2013.01)

(58) Field of Classification Search
  None
  See application file for complete search history.

(56) References Cited

U.S. PATENT DOCUMENTS

| 7,691,997 B2 | 4/2010 | Khvorova et al. |
| 2005/0048529 A1 | 3/2005 | McSwiggen |
| 2006/0058266 A1 | 3/2006 | Manoharan et al. |
| 2008/0076701 A1 | 3/2008 | Quay et al. |
| 2008/0146788 A1 | 6/2008 | Bhat et al. |
| 2008/0269156 A1 | 10/2008 | Feinstein et al. |

FOREIGN PATENT DOCUMENTS

WO    WO 09/044392    4/2009

OTHER PUBLICATIONS

International Preliminary Report on Patentability dated Jun. 20, 2013 in connection with PCT International Application No. PCT/US2011/063365.
Prakash et al., (2006)' RNA interference by 2', 5'-linked nucleic acid duplexes in mammalian cells, Bioorg Med Chem Lett., vol. 16:3238-40 (2006).
Schöning et al., (2000), "Chemical Etiology of Nucleic Acid 3 Structure: The a-Threofuranosyl-(3'2') Oligonucleotide System", Science, vol. 290:1347-1351 (2000).

*Primary Examiner* — Kimberly Chong
(74) *Attorney, Agent, or Firm* — Fish & Richardson P.C.

(57) ABSTRACT

Disclosed herein are double stranded RNA molecules which have been modified to exhibit one of the following, increased activity, enhanced nuclease stability, reduced off target activity and or reduced immunogenicity, to pharmaceutical compositions comprising such compounds and to methods of use. Further disclosed is a method for the synthesis of threose nucleic acid phosphoramidites and methods of use thereof.

23 Claims, 8 Drawing Sheets

Specification includes a Sequence Listing.

MYD88_11_S1297

Sense detection

Antisense detection

MYD88_11_S889

Sense detection

Antisense detection

FIGURE 5E

|  | Ctrl | 1 | 1 |
|---|---|---|---|
| MYD88_11_S1_1788 | 300 nM | 0.99 | 0.97 |
|  | 100 nM | 0.76 | 0.78 |
|  | 33 nM | 1.17 | 0.85 |
| MYD88_11_S1_1789 | 300 nM | 1.38 | 0.00 |
|  | 100 nM | 5.22 | 0.37 |
|  | 33 nM | 1.25 | 0.79 |
| MYD88_11_S1_1790 | 300 nM | 2.69 | 0.81 |
|  | 100 nM | 0.92 | 0.76 |
|  | 33 nM | 0.86 | 0.75 |
| MYD88_11_S4_1276 | 300 nM | 1.00 | 0.75 |
|  | 100 nM | 2.12 | 1.57 |
|  | 33 nM | 1.20 | 0.73 |
| MYD88_11_S5_782 | 300 nM | 1.28 | 0.68 |
|  | 100 nM | 1.21 | 0.81 |
|  | 33 nM | 1.14 | 0.96 |
| Poly I:C (ug/ml) | 0.56 | 129.39 | 24.14 |
|  | 1.7 | 265.65 | 28.49 |
|  | 5 | 346.07 | 81.31 |
| CL075 (ug/ml) | 0.12 | 98.14 |  |
|  | 0.67 | 73.44 | 34.00 |
|  | 2 | 96.00 | 54.00 |

STRUC2_S1322

STRUC2_S1315

STRUC2_S1316

STRUC2_S1317

STRUC2_S1318

STRUC2_S1319

DOUBLE STRANDED OLIGONUCLEOTIDE COMPOUNDS COMPRISING POSITIONAL MODIFICATIONS

RELATED APPLICATIONS

This application is a continuation application of and claims priority to U.S. application Ser. No. 13/991,610 filed on Aug. 23, 2013, which is a § 371 national stage of PCT International Application No. PCT/US2011/063365, filed on Dec. 6, 2011 claiming the benefit of U.S. Provisional Application Nos. 61/419,910 filed on Dec. 6, 2010 and 61/419,918 filed on Dec. 6, 2010, the contents of each of these applications are hereby incorporated by reference in their entirety into this application.

SEQUENCE LISTING

The instant application contains a Sequence Listing which has been submitted electronically in ASCII format and is hereby incorporated by reference in its entirety. The ASCII copy, created on Mar. 29, 2018, is named 40792-0004002_SL.txt and is 69,869 bytes in size.

FIELD OF THE INVENTION

Disclosed herein are positionally modified double stranded nucleic acid molecules including double stranded RNA (dsRNA), siRNA and siNA, pharmaceutical compositions comprising same and methods of use thereof for the inhibition of gene expression. The molecules include positional modifications on the sense strand on the antisense strand or on both the sense strand and the antisense strand thereby imparting on the molecules beneficial properties including one or more of increased knock down activity of target gene expression, increased stability to endo- and or exonucleases, reduced off-target effects and/or lack of immunomodulating effects and are useful in the treatment of subjects suffering from diseases or conditions and or symptoms associated with such diseases or conditions or at risk of contracting diseases or conditions in which target gene expression has adverse consequences. Further provided is a method for the synthesis of threose nucleic acid (TNA) phosphoramidites and nucleic acid molecules comprising TNA moieties.

BACKGROUND OF THE INVENTION

PCT Patent Publication Nos. WO 2008/104978, WO 2009/044392, WO 2011/066475 and WO 2011/084193 to the assignee of the present invention and hereby incorporated by reference in their entirety, disclose nucleic acid sequences and modifications useful in generating dsRNA molecules.

The synthesis of (L)-alpha-threofuranosyl (TNA) phosphoramidites is described in Scheming et al., Helv. Chim. Acta 85:4111-4153 (2002). Attempts by the present inventors to repeat the syntheses described therein for the preparation of cytosine- and adenine-containing TNAs were unsuccessful.

There remains a need for active and effective dsRNA therapeutic agents which exhibit knock down on target activity and/or reduced off target effects.

SUMMARY OF THE INVENTION

The double stranded RNA (dsRNA) compounds disclosed herein possess structures and modifications which may, for example increase activity, increase stability, reduce immunogenicity, reduce off-target effects, enhance loading into the RISC complex, and or minimize toxicity when compared to an unmodified dsRNA molecule; the novel modifications are beneficially applied to double stranded RNA useful in down regulating, preventing, inhibiting or attenuating target gene expression.

Provided herein are double stranded (duplex) nucleic acid molecules useful for the down regulation of gene expression. In various embodiments, provided are nucleic acid molecules comprising at least one threose nucleic acid (TNA) moiety. In some embodiments the nucleic acid molecule is a single stranded nucleic acid molecule, including antisense, miRNA or antagomir. In some embodiments the nucleic acid molecule is a double stranded nucleic acid molecule, including dsRNA, siRNA and siNA. The TNA moiety is present in the sense strand, in the antisense strand or in the both the sense strand and the antisense strand.

Further provided are double stranded nucleic acid molecules comprising TNA moieties, 2'5' nucleotides including 2'5' deoxyribonucleotides and 2'5' ribonucleotides, pseudouridine moieties at various positions in the sense strand, in the antisense strand or in the both the sense strand and the antisense strand thereby imparting on the molecules beneficial properties when compared to an unmodified molecule.

According to one aspect provided are double stranded nucleic acid molecules having structure A1 set forth below:

(A1) 5' (N)x-Z 3' (antisense strand)
3' Z'-(N')y-z" 5' (sense strand)

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides or non-nucleotide moieties or a combination thereof covalently attached at the 3' terminus of the strand in which it is present;
wherein z" may be present or absent, but if present is a capping moiety covalently attached at the 5' terminus of (N')y;
wherein each of x and y is independently an integer between 18 and 25;
wherein the sequence of (N')y has complementarity to the sequence of (N)x and (N)x includes an antisense sequence complementary to a consecutive sequence in a target RNA; and
wherein the double stranded nucleic acid comprises one or more of the following modifications a. a threose nucleic acid moiety, a 2'5' nucleotide or a mirror nucleotide in the antisense strand in at least one of positions 5, 6, 7, 8, or 9 from the 5' terminus;
   b. a threose nucleic acid moiety, a 2'5' nucleotide or a pseudoUridine in the sense strand in at least one of positions 9 or 10 from the 5' terminus;
   c. from 1-10 threose nucleic acid moieties or 2'5' nucleotides in the sense strand at the 3' terminal or penultimate positions.

In some embodiments the covalent bond joining each consecutive N or N' is a phosphodiester bond.

In some embodiments x=y and each of x and y is 19, 20, 21, 22 or 23. In various embodiments x=y=19.

In some embodiments the sequence of (N')y is fully complementary to the sequence of (N)x. In some embodiments the sequence of (N)x is fully complementary to the target RNA.

In preferred embodiments x=19. In some embodiments (N)x comprises a threose nucleic acid moiety in position 5 from the 5' terminus. In some embodiments (N)x comprises a threose nucleic acid moiety in position 6 from the 5' terminus. In some embodiments (N)x comprises a threose nucleic acid moiety in position 7 from the 5' terminus. In some embodiments (N)x comprises a threose nucleic acid moiety in position 8 from the 5' terminus. In some embodiments (N)x comprises a threose nucleic acid moiety in position 9 from the 5' terminus. In some embodiments (N)x comprises two threose nucleic acid moiety in positions 5-6, 6-7, 7-8 or 8-9 from the 5' terminus.

In some embodiments (N)x comprises a 2'5' nucleotide in position 5 from the 5' terminus. In some embodiments (N)x comprises a 2'5' nucleotide in position 6 from the 5' terminus. In some embodiments (N)x comprises a 2'5' nucleotide in position 7 from the 5' terminus. In some embodiments (N)x comprises a 2'5' nucleotide in position 8 from the 5' terminus. In some embodiments (N)x comprises a 2'5' nucleotide in position 9 from the 5' terminus.

In some embodiments (N)x comprises a mirror nucleotide in position 5 from the 5' terminus. In some embodiments (N)x comprises a mirror nucleotide in position 6 from the 5' terminus. In some embodiments (N)x comprises a mirror nucleotide in position 7 from the 5' terminus. In some embodiments (N)x comprises a mirror nucleotide in position 8 from the 5' terminus. In some embodiments (N)x comprises a mirror nucleotide in position 9 from the 5' terminus.

In preferred embodiments y=19. In some embodiments (N')y comprises a threose nucleic acid moiety in position 9 from the 5' terminus. In some embodiments (N')y comprises a threose nucleic acid moiety in position 10 from the 5' terminus.

In some embodiments (N')y comprises a 2'5' nucleotide in position 9 from the 5' terminus. In some embodiments (N')y comprises a 2'5' nucleotide in position 10 from the 5' terminus.

In some embodiments (N')y comprises a pseudoUridine in position 9 from the 5' terminus. In some embodiments (N')y comprises a pseudoUridine in position 10 from the 5' terminus.

In preferred embodiments y=19. In some embodiments (N')y comprises 2, 3, 4, 5, 6, 7, 8, 9 or 10 threose nucleic acid moieties at the 3' terminal or penultimate positions of (N')y. In some embodiments (N')y comprises 2, 3, 4, 5, 6, 7 or 8 consecutive threose nucleic acid moieties at the 3' terminal or penultimate positions of (N')y. In some embodiments (N')y comprises threose nucleic acid moieties in positions 18-19, 17-18, 16-17, or 15-16 from the 5' terminus. In some embodiments (N')y comprises threose nucleic acid moieties in positions 15-17, 15-18 or 15-19 from the 5' terminus. In some embodiments (N')y comprises threose nucleic acid moieties in positions 11-19, 12-19, 13-19, 14-19, 15-19, 16-19, 17-19, from the 5' terminus. In some embodiments (N')y comprises threose nucleic acid moieties in positions 11-18, 12-18, 13-18, 14-18, 15-18, 16-18 from the 5' terminus.

In preferred embodiments y=19. In some embodiments (N')y comprises 4, 5 or 6 2'5' nucleotides at the 3' terminal or penultimate positions of (N')y. In some embodiments (N')y comprises 4 or 5, consecutive 2'5' nucleotides at the 3' terminal or penultimate positions of (N')y. In some embodiments (N')y comprises 2'5' nucleotides in positions 18-19, 17-18, 16-17, or 15-16 from the 5' terminus. In some embodiments (N')y comprises 2'5' nucleotides in positions 15-17, 15-18 or 15-19 from the 5' terminus. In some embodiments (N')y comprises 2'5' nucleotides in positions 16-19 or 17-19, from the 5' terminus.

In various embodiments the double stranded molecule comprises a mismatch to the target mRNA at the 5' terminal nucleotide of the guide strand. Accordingly in various embodiments provided are double stranded nucleic acid molecule having the following structure:

(A2) 5' $N^1$-(N)x-Z 3' (antisense strand)
3' Z'-$N^2$-(N')y-z" 5' (sense strand)

wherein each of $N^2$, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 24;

wherein the sequence of (N')y has complementarity to the sequence of (N)x and (N)x comprises an antisense sequence complementary to a consecutive sequence in a target RNA;

wherein $N^1$ is covalently bound to (N)x and is mismatched to the target RNA or is a complementary DNA moiety to the target RNA;

wherein $N^1$ is a moiety selected from the group consisting of natural or modified uridine, deoxyribouridine, ribothymidine, deoxyribothymidine, adenosine or deoxyadenosine;

wherein z" may be present or absent, but if present is a capping moiety covalently attached at the 5' terminus of $N^2$-(N')y;

wherein each of Z and Z' is independently present or absent, but if present is independently 1-5 consecutive nucleotides, consecutive non-nucleotide moieties or a combination thereof covalently attached at the 3' terminus of the strand in which it is present; and wherein the double stranded nucleic acid comprises one or more of the following modifications a. a threose nucleic acid moiety, a 2'5' nucleotide or a mirror nucleotide in at least one of positions 5, 6, 7, 8, or 9 from the 5' terminus of the antisense strand (N)x;

b. a threose nucleic acid moiety, a 2'5' nucleotide or a pseudoUridine in at least one of positions 9 or 10 from the 5' terminus of (N')y;

c. 1, 2, 3, 4, 5, 6, 7, 8, 9 or 10 threose nucleic acid moieties or 2'5' nucleotides at the 3' terminal or penultimate positions of (N')y.

In some embodiments the sequence of (N')y is fully complementary to the sequence of (N)x. In various embodiments sequence of $N^2$-(N')y is complementary to the sequence of $N^1$-(N)x. In some embodiments (N)x comprises an antisense that is fully complementary to about 17 to about 24 consecutive nucleotides in a target RNA. In other embodiments (N)x comprises an antisense that is substantially complementary to about 17 to about 39 consecutive nucleotides in a target RNA.

In some embodiments N and $N^2$ form a Watson-Crick base pair. In some embodiments $N^1$ and $N^2$ form a non-Watson-Crick base pair. In some embodiments a base pair is formed between a ribonucleotide and a deoxyribonucleotide.

In some embodiments x=y=18, x=y=19 or x=y=20. In preferred embodiments x=y=18.

In some embodiments $N^1$ is covalently bound to (N)x and is mismatched to the target RNA. In various embodiments $N^1$ is covalently bound to (N)x and is a DNA moiety complementary to the target RNA.

In some embodiments $N^1$ is covalently bound to (N)x and is a DNA moiety complementary to the target RNA.

In some embodiments $N^1$ is selected from adenosine, deoxyadenosine, deoxyuridine, ribothymidine or deoxythymidine, and wherein the nucleotide in the pairing nucleotide in the target RNA is adenosine. In preferred embodiments $N^1$ selected from adenosine, deoxyadenosine or deoxyuridine.

In some embodiments $N^1$ is selected from adenosine, deoxyadenosine, uridine, deoxyuridine, ribothymidine or deoxythymidine and wherein the nucleotide in the pairing nucleotide in the target RNA is cytidine. In preferred embodiments $N^1$ is selected from adenosine, deoxyadenosine, uridine or deoxyuridine.

In some embodiments $N^1$ is selected from adenosine, deoxyadenosine, uridine, deoxyuridine, ribothymidine or deoxythymidine and wherein the nucleotide in the pairing nucleotide in the target RNA is guanosine.

In preferred embodiments $N^1$ is selected from adenosine, deoxyadenosine, uridine or deoxyuridine.

In some embodiments $N^1$ is selected from deoxyadenosine, deoxyuridine, ribothymidine or deoxythymidine and wherein the nucleotide in the pairing nucleotide in the target RNA is uridine. In preferred embodiments $N^1$ is selected from deoxyadenosine or deoxyuridine.

In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

In some embodiments of the double stranded nucleic acid molecules of Structures A1 and A2, N in at least one of positions 5, 6, 7, 8, or 9 from the 5' terminus of the antisense strand [(N)x or $N^1$-(N)x] is selected from a threose nucleic acid (TNA) moiety, a 2'5' nucleotide, a mirror nucleotide or a combination thereof. Without wishing to be bound to theory, a double stranded nucleic acid molecule having a threose nucleic acid (TNA) moiety, a 2'5' nucleotide, a mirror nucleotide at any one or more of the aforementioned positions confers increased on target activity and/or decreased off target activity and or increased stability to nucleases.

In some embodiments the antisense strand [(N)x of Structure A1 or $N^1$-(N)x of Structure A2] comprises a TNA moiety in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments the antisense strand [(N)x of Structure A1 or $N^1$-(N)x of Structure A2] comprises a threose nucleic acid moiety in position 5 from the 5' terminus. In some embodiments the antisense strand [(N)x of Structure A1 or $N^1$-(N)x of Structure A2] comprises a threose nucleic acid moiety in position 6 from the 5' terminus. In some embodiments the antisense strand [(N)x of Structure A1 or $N^1$-(N)x of Structure A2] comprises a threose nucleic acid moiety in position 7 from the 5' terminus. In some embodiments the antisense strand [(N)x of Structure A1 or $N^1$-(N)x of Structure A2] comprises a threose nucleic acid moiety in position 8 from the 5' terminus. In some embodiments the antisense strand [(N)x of Structure A1 or $N^1$-(N)x of Structure A2] comprises a threose nucleic acid moiety in position 9 from the 5' terminus. In some embodiments the antisense strand [(N)x of Structure A1 or $N^1$-(N)x of Structure A2] comprises two threose nucleic acid moiety in positions 5-6, 6-7, 7-8 or 8-9 from the 5' terminus.

In some embodiments the antisense strand comprises a 2'5' nucleotide in position 5 from the 5' terminus. In some embodiments the antisense strand comprises a 2'5' nucleotide in position 6 from the 5' terminus. In some embodiments the antisense strand comprises a 2'5' nucleotide in position 7 from the 5' terminus. In some embodiments the antisense strand comprises a 2'5' nucleotide in position 8 from the 5' terminus. In some embodiments the antisense strand comprises a 2'5' nucleotide in position 9 from the 5' terminus.

In some embodiments the antisense strand comprises a mirror nucleotide in position 5 from the 5' terminus. In some embodiments the antisense strand comprises a mirror nucleotide in position 6 from the 5' terminus. In some embodiments the antisense strand comprises a mirror nucleotide in position 7 from the 5' terminus. In some embodiments the antisense strand comprises a mirror nucleotide in position 8 from the 5' terminus. In some embodiments the antisense strand comprises a mirror nucleotide in position 9 from the 5' terminus.

In some embodiments the sense strand [(N')y of Structure A1 or N2-(N')y of structure A2] comprises a threose nucleic acid moiety in position 9 from the 5' terminus. In some embodiments the sense strand comprises a threose nucleic acid moiety in position 10 from the 5' terminus.

In some embodiments the sense strand comprises a 2'5' nucleotide in position 9 from the 5' terminus. In some embodiments the sense strand comprises a 2'5' nucleotide in position 10 from the 5' terminus.

In some embodiments the sense strand comprises a pseudoUridine in position 9 from the 5' terminus. In some embodiments the sense strand comprises a pseudoUridine in position 10 from the 5' terminus.

In some embodiments the sense strand comprises 2, 3, 4, 5, 6, 7, 8, 9 or 10 threose nucleic acid moieties at the 3' terminal or penultimate positions of the sense strand. In some embodiments the sense strand comprises 2, 3, 4, 5, 6, 7 or 8 consecutive threose nucleic acid moieties at the 3' terminal or penultimate positions of the sense strand. In some embodiments the sense strand comprises threose nucleic acid moieties in positions 18-19, 17-18, 16-17, or 15-16 from the 5' terminus. In some embodiments the sense strand comprises threose nucleic acid moieties in positions 15-17, 15-18 or 15-19 from the 5' terminus. In some embodiments the sense strand comprises threose nucleic acid moieties in positions 11-19, 12-19, 13-19, 14-19, 15-19, 16-19, 17-19, from the 5' terminus. In some embodiments the sense strand comprises threose nucleic acid moieties in positions 11-18, 12-18, 13-18, 14-18, 15-18, 16-18 from the 5' terminus.

In some embodiments the double stranded molecule includes a combination of the following modifications
a) the antisense strand includes a 2'5' nucleotide, TNA moiety or a mirror nucleotide in at least one of positions 5, 6, 7, 8, or 9 from the 5' terminus; and
b) the sense strand includes at least one of a 2'5' nucleotide, TNA moiety and a pseudoUridine in positions 9 or 10 from the 5' terminus.

In some embodiments the sense strand further includes a capping moiety covalently attached to the 5' terminus (z"). In some embodiments Z and or Z' is present and includes a nucleotide or non-nucleotide overhang covalently attached to the 3' terminus of the strand in which it is present. In some embodiments Z includes a dTdT dinucleotide overhang or a C3Pi-C3Pi non-nucleotide overhang. In some embodiments Z' includes a dTdT dinucleotide overhang or a C3Pi or C3OH non-nucleotide overhang.

In some embodiments the double stranded molecule includes a combination of the following modifications
a) the antisense strand includes a 2'5' nucleotide, TNA moiety or a mirror nucleotide in at least one of positions 5, 6, 7, 8, or 9 from the 5' terminus; and c) the sense strand includes 1, 2, 3, 4, 5, 6, 7, 8, 9 or 10 TNA at the 3' penultimate or 3' terminal positions.

In some embodiments the sense strand further includes a capping moiety covalently attached to the 5' terminus (z"). In some embodiments Z and or Z' is present and includes a nucleotide or non-nucleotide overhang covalently attached to the 3' terminus of the strand in which it is present. In some embodiments Z includes a dTdT dinucleotide overhang or a C3Pi-C3Pi non-nucleotide overhang. In some embodiments Z' includes a dTdT dinucleotide overhang or a C3Pi or C3OH non-nucleotide overhang.

In some embodiments the double stranded molecule includes a combination of the following modifications
a) the antisense strand includes a 2'5' nucleotide, TNA moiety or a mirror nucleotide in at least one of positions 5, 6, 7, 8, or 9 from the 5' terminus; and
c) the sense strand includes 4, 5, 6 2'5' nucleotides at the 3' penultimate or 3' terminal positions.

In some embodiments the sense strand further includes a capping moiety covalently attached to the 5' terminus (z"). In some embodiments Z and or Z' is present and includes a nucleotide or non-nucleotide overhang covalently attached to the 3' terminus of the strand in which it is present. In some embodiments Z includes a dTdT dinucleotide overhang or a C3Pi-C3Pi non-nucleotide overhang. In some embodiments Z' includes a dTdT dinucleotide overhang or a C3Pi or C3OH non-nucleotide overhang.

In some embodiments the sense strand [(N')y of Structure A1 or $N^2$-(N')y of Structure A2] comprises a TNA moiety in position 12, in position 13, in position 14, in position 15, in position 16, in position 17, in position 18, in position 19, in positions 12-13, in positions 13-14, in positions 14-15, in positions 15-16, in positions 16-17, in positions 17-18, in positions 18-19, in positions 12-14, in positions 13-15, in positions 14-16, in positions 15-17, in positions 16-18, in positions 17-19, in positions 12-15, in positions 13-16, in positions 14-17, in positions 15-18, in positions 16-19, in positions 12-16, in positions 13-17, in positions 14-18, in positions 15-19, in positions 12-17, in positions 13-18, in positions 14-19, in positions 12-18, in positions 13-19 or in positions 12-19. In some embodiments any one of positions 12-19 is independently a TNA or unmodified. For example, in some embodiments a TNA is present in positions 14 and 16-19, in positions 13-14 and 16-19, or in positions 12-14 and 16-19. In particular embodiments the sense strand [(N')y of Structure A1 or $N^2$-(N')y of Structure A2] comprises a TNA moiety in position 19, positions 18-19, positions 17-19, positions 16-19, positions 15-19, positions 14-19, positions 13-19 or in positions 12-19. In some embodiments the sense strand [(N')y of Structure A1 or $N^2$-(N')y of Structure A2] further comprises a TNA nucleic acid moiety at one or more of positions (5'>3') 2, 3, 4, 5, 6, 7, 8, 9 or 10.

In some embodiments the antisense strand [(N)x of Structure A1 or $N^1$-(N)x of Structure A2] comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments the antisense strand [(N)x of Structure A1 or $N^1$-(N)x of Structure A2] comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments of the double stranded nucleic acid molecules, N' in at least one of positions 9 or 10 from the 5' terminus of the sense strand [(N')y in Structure A1 or $N^2$-(N')y in Structure A2] is selected from a threose nucleic acid (TNA) moiety, a 2'5' nucleotide, a pseudoUridine or a combination thereof. Without wishing to be bound to theory, a double stranded nucleic acid molecule having a threose nucleic acid (TNA) moiety, a 2'5' nucleotide, or a pseudoUridine at any one or more of positions 9 or 10 in the sense (passenger) strand confers increased on target activity and/or increased nuclease stability.

In some embodiments (N')y in Structure A1 or $N^2$-(N')y in Structure A2 comprises a threose nucleic acid (TNA) moiety in position 9, or in position 10 or in positions 9-10.

In some embodiments (N')y in Structure A1 or $N^2$-(N')y in Structure A2 comprises a 2'5' nucleotide in position 9, or in position 10 or in positions 9-10.

In some embodiments (N')y in Structure A1 or $N^2$-(N')y in Structure A2 comprises a pseudoUridine in position 9, or in position 10 or in positions 9-10.

In some embodiments of the double stranded nucleic acid molecules, N' comprises 2, 3, 4, 5, 6, 7, 8, 9 or 10 consecutive 2'5' nucleotides or TNA nucleotides at the 3' terminus of the sense strand [(N')y in Structure A1 or $N^2$-(N')y in Structure A2], from the terminal or penultimate position. Without wishing to be bound to theory, such a double stranded nucleic acid molecule confers increased nuclease stability to the duplex and or reduced off target effect of the sense (passenger) strand. In some embodiments the sense strand further comprises Z'. In some embodiments Z comprises a C3 moiety (for example C3Pi, C3-OH) or a 3' terminal phosphate (Pi).

In some embodiments of Structure A1 and A2 the sense strand comprises four consecutive 2'5' nucleotides at the 3' terminal or penultimate position. In some embodiments of structure A1 x=y=19 and (N')y comprises 2'5' nucleotides in positions 15, 16, 17, and 18 or in positions 16, 17, 18, and 19. In some embodiments of structure A2 x=y=18 and $N^2$-(N')y comprises 2'5' nucleotides in positions 15, 16, 17, and 18 or in positions 16, 17, 18, and 19.

In some embodiments of Structure A1 and A2 the sense strand comprises five consecutive 2'5' nucleotides at the 3' terminal or penultimate position. In some embodiments of structure A1 x=y=19 and (N')y comprises 2'5' nucleotides in positions 14, 15, 16, 17, and 18 or in positions 15, 16, 17, 18, and 19. In some embodiments of structure A2 x=y=18 and $N^2$-(N')y comprises 2'5' nucleotides in positions 14, 15, 16, 17, and 18 or in positions 15, 16, 17, 18, and 19.

In some embodiments of Structure A1 and A2 the sense strand comprises six consecutive 2'5' nucleotides at the 3' terminal or penultimate position. In some embodiments of structure A1 x=y=19 and (N')y comprises 2'5' nucleotides in positions 13, 14, 15, 16, 17, and 18 or in positions 14, 15, 16, 17, 18, and 19. In some embodiments of structure A2 x=y=18 and $N^2$-(N')y comprises 2'5' nucleotides in positions 13, 14, 15, 16, 17, and 18 or in position 14, 15, 16, 17, 18, and 19.

In preferred embodiments the double stranded nucleic acid molecule comprises modifications according to a) and b) or a) and c). For example, in one embodiment a double stranded molecule includes
a threose nucleic acid moiety or a 2'5' nucleotide in at least one of positions 5, 6, 7, 8, or 9 from the 5' terminus of the antisense strand and a threose nucleic acid moiety or a 2'5' nucleotide in at least one of positions 9 or 10 from the 5' terminus of the sense strand. In additional embodiments the sense strand and or the antisense strand further includes 2'OMe sugar modified pyrimidine ribonucleotides. The double stranded molecule may further include a capping moiety covalently attached to the 5' terminus of the sense strand.

In another embodiment a double stranded molecule includes a threose nucleic acid moiety or a 2'5' nucleotide or a mirror nucleotide in at least one of positions 5, 6, 7, 8, or 9 from the 5' terminus of the antisense strand and
1, 2, 3, 4, 5, 6, 7, 8, 9 or 10 threose nucleic acid moieties at the 3' terminal or penultimate positions of (N')y. In additional embodiments the sense strand and or the antisense strand further includes 2'OMe sugar modified pyrimidine ribonucleotides. The double stranded molecule may further include a capping moiety covalently attached to the 5' terminus of the sense strand.

In another embodiment a double stranded molecule includes a threose nucleic acid moiety or a 2'5' nucleotide or a mirror nucleotide in at least one of positions 5, 6, 7, 8, or 9 from the 5' terminus of the antisense strand and
4, 5, or 6, 2'5' nucleotide at the 3' terminal or penultimate positions of (N')y.

In one preferred embodiment the double stranded molecule further comprises a 2'5' nucleotide in position 9 or 10 in the sense strand. In additional embodiments the sense strand and or antisense strand further includes 2'OMe modified pyrimidine ribonucleotides.

In another embodiment a double stranded molecule includes
N in at least one of positions 5, 6, 7, 8, or 9 from the 5' terminus of the antisense strand is selected from a threose nucleic acid moiety, a 2'5' nucleotide or a mirror nucleotide; and
N' in 1, 2, 3, 4, 5, 6, 7, 8, 9, or 10 positions at the 3' terminal or penultimate position positions of the sense strand comprises a 2'5' nucleotide.

In another embodiment a double stranded molecule includes
N in at least one of positions 5, 6, 7, 8, or 9 from the 5' terminus of the antisense strand is selected from a threose nucleic acid moiety, a 2'5' nucleotide or a mirror nucleotide; and
N' in 1, 2, 3, 4, 5, 6, 7, 8, 9, or 10 positions at the 3' terminal or penultimate position positions of the sense strand comprises a TNA moiety. In some embodiments the double stranded nucleic acid molecule is a siRNA, siNA or a miRNA.

In another aspect provided are pharmaceutical compositions comprising a molecule according to Structure (A1) or (A2), in an amount effective to inhibit mammalian or non-mammalian gene expression; and a pharmaceutically acceptable carrier. In some embodiments the mammalian gene is a human gene. In some embodiments the non-mammalian gene is a bacterial gene or a viral gene. In some embodiments the non-mammalian gene is involved in a mammalian disease, preferably human disease.

Further provided are methods for treating or preventing the incidence or severity of a disease or condition and/or for reducing the risk or severity of a disease or condition in a subject in need thereof wherein the disease or condition and/or a symptom and/or risk associated therewith is associated with expression of a mammalian or a non-mammalian gene. In a preferred embodiment the subject is a human subject.

In some embodiments the disease or condition is selected from hearing loss, acute renal failure (ARF), Delayed Graft Function (DGF) after kidney transplantation, glaucoma, ocular ischemic conditions including anterior ischemic optic neuropathy, age-related macular degeneration (AMD), Ischemic Optic Neuropathy (ION), dry eye syndrome, acute respiratory distress syndrome (ARDS) and other acute lung and respiratory injuries, chronic obstructive pulmonary disease (COPD), primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, organ transplantation including lung, liver, heart, pancreas, and kidney transplantation, nephro- and neurotoxicity, spinal cord injury, brain injury, neurodegenerative disease or condition, pressure sores, oral mucositis fibrotic conditions including liver fibrosis, lung fibrosis; ocular neuropathy, elevated intraocular pressure (IOP), Sjögrens Syndrome, diabetic retinopathy (DR), diabetic macular edema (DME), optic neuritis, central retinal vein occlusion, brunch retinal vein occlusion, optic nerve injury, retinopathy of prematurity (ROP), retinitis pigmentosa (RP), retinal ganglion degeneration, macular degeneration, hereditary optic neuropathy, Leber's hereditary optic neuropathy, neuropathy due to a toxic agent and neuropathy caused by an adverse drug reaction or a vitamin deficiency; Meniere's disease and cancer. Such methods involve administering to a mammal in need of such treatment a prophylactically or therapeutically effective amount of one or more such compounds, which inhibit or reduce expression or activity of at least one such gene.

In another aspect, provided herein is a method for the synthesis of TNA phosphoramidites and for their use in generating oligonucleotides, including single stranded and double stranded nucleic acid molecules.

There are provided, in accordance with embodiments of the invention, methods for synthesizing cytosine- and adenine-containing TNAs, as well as certain intermediates thereto.

In one aspect, provided is a method for the synthesis of (L)-alpha-threofuranosyl oligonucleotides (TNA) phosphoramidites.

In one embodiment, there is provided a method for making a compound of the formula

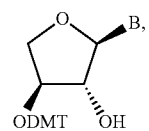

wherein DMT is dimethoxytrityl and B is chosen from

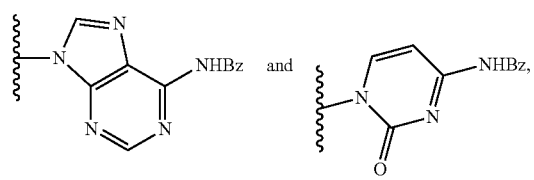

wherein Bz stands for benzoyl, comprising reacting a compound of the formula

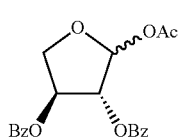

with a compound of the formula B—H to form a compound of formula

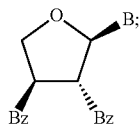

converting said compound of formula

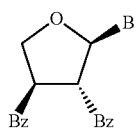

to a compound of formula

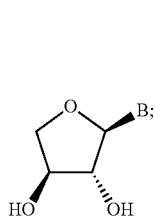

and reacting said compound of formula

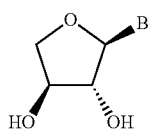

with 1-(chloro(4-methoxyphenyl)(phenyl)methyl)-4-methoxybenzene in the presence of silver nitrate and silver triflate to form a compound of formula

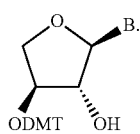

In some embodiments, the compound of formula

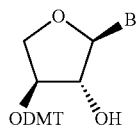

is separated from a compound of formula

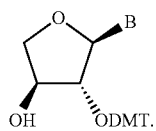

In some embodiments the separation is effected by column chromatography. In some embodiments, a base is employed along with the silver nitrate and silver triflate. In some embodiments, the base is lutidine. In some embodiments, B is

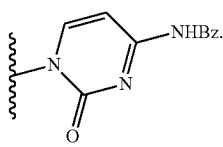

In some embodiments, B is

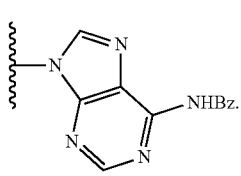

There is also provided, in accordance with an embodiment of the invention, a method of making a compound of the formula

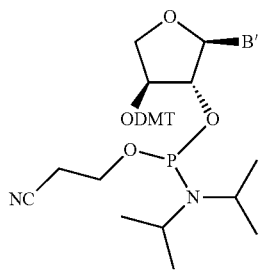

wherein B' is selected from

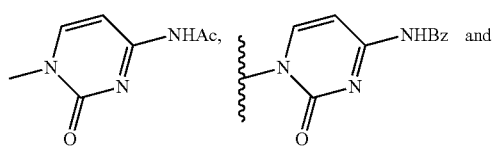

-continued

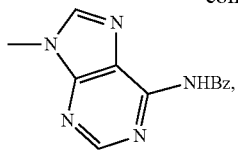

comprising preparing a compound of formula

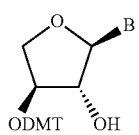

as described above; optionally, when B is

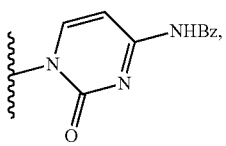

replacing the benzoyl moiety with an acetyl moiety; and contacting the compound with chloro(2-cyanoethoxy)-(diisopropylamino)phosphine in the presence of a base to form the compound of formula

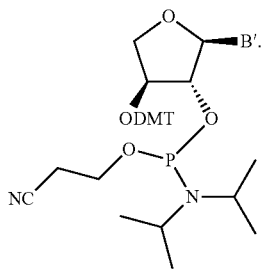

In another aspect provided are nucleic acid molecules comprising TNA moieties in one or more positions. In some embodiments the nucleic acid molecules are selected from antisense molecules, siNA molecules, dsRNA molecules, siRNA molecules and miRNA molecules.

Use of the TNA Phosphoramidites to Synthesize Oligonucleotides

TNA phosphoramidites were synthesized using a novel method developed by the applicant. The synthesis of dsRNA including chimeric oligonucleotides including RNA and TNA phosphoramidites was carried out using established solid phase synthesis methods, with some modifications to optimize the coupling yields (Schoning et al, 2002. Helvetica Chimica ACTA 85:4111-4153).

The TNA phosphoramidites disclosed herein were incorporated into oligonucleotides, in particular into antisense strands and sense strands useful in generating double stranded nucleic acid molecules, including siRNA, siNA, miRNA. Applicants have shown that a dsRNA comprising at least one TNA moiety, and preferably 2, 3, 4, 5, 6, 7, 8, 9 or 10 TNA moieties in the sense strand, exhibits reduced off-target activity, increased on-target activity and or stability, compared to an unmodified dsRNA molecule.

In one embodiment, provided are double stranded nucleic acid molecules having the structure (A3):

(A3) 5' (N)x-Z 3' (antisense strand)
3' Z'-(N')y-z" 5' (sense strand)

wherein each of N and N' is a ribonucleotide which may be unmodified or modified, or an unconventional moiety and wherein at least one of N or N' is a TNA moiety;

wherein each of (N)x and (N')y is an oligonucleotide in which each consecutive N or N' is joined to the next N or N' by a covalent bond;

wherein each of Z and Z' is independently present or absent, but if present independently includes 1-5 consecutive nucleotides or non-nucleotide moieties or a combination thereof covalently attached at the 3' terminus of the strand in which it is present;

wherein z" may be present or absent, but if present is a capping moiety covalently attached at the 5' terminus of (N')y;

wherein each of x and y is independently an integer between 18 and 40;

wherein the sequence of (N')y has complementarity to the sequence of (N)x; and wherein (N)x includes an antisense sequence to a target gene.

In some embodiments the covalent bond joining each consecutive N or N' is a phosphodiester bond.

In some embodiments x=y and each of x and y is 19, 20, 21, 22 or 23. In various embodiments x=y=19.

In some embodiments the double stranded nucleic acid molecule is a siRNA, siNA or a miRNA.

In some embodiments the sense strand comprises a TNA moiety at one or more of the 10 most 3' terminal positions strand. In some embodiments the sense strand comprises 2, 3, 4, 5, 6, 7, 8, 9, or 10 TNA moieties at the 3' terminus of the strand. In some embodiments each of the sense strand and the antisense strand comprises at least one TNA moiety.

In various embodiments the double stranded molecule comprises a mismatch to the target mRNA at the 5' terminal nucleotide of the guide strand. Accordingly in various embodiments provided are double stranded nucleic acid molecule having the following structure:

(A4) 5' $N^1$-(N)x-Z 3' (antisense strand)
3' Z'-$N^2$-(N')y-z" 5' (sense strand)

wherein each of $N^2$, N and N' is an unmodified or modified ribonucleotide, or an unconventional moiety and wherein at least one of N or N' is a TNA moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y has complementarity to the sequence of (N)x and (N)x has complementarity to a consecutive sequence in a target RNA;

wherein $N^1$ is covalently bound to (N)x and is mismatched to the target RNA or is a complementary DNA moiety to the target RNA;

wherein $N^1$ is a moiety selected from the group consisting of natural or modified uridine, deoxyribouridine, ribothymidine, deoxyribothymidine, adenosine or deoxyadenosine;

wherein z" may be present or absent, but if present is a capping moiety covalently attached at the 5' terminus of $N^2$-(N')y; and wherein each of Z and Z' is independently present or absent, but if present is independently 1-5 consecutive nucleotides, consecutive non-nucleotide moieties or a combination thereof covalently attached at the 3' terminus of the strand in which it is present.

In some embodiments the sequence of (N')y is fully complementary to the sequence of (N)x. In various embodiments sequence of $N^2$-(N')y is complementary to the sequence of $N^1$-(N)x. In some embodiments (N)x comprises an antisense that is fully complementary to about 17 to about 24 consecutive nucleotides in a target RNA. In other embodiments (N)x comprises an antisense that is substantially complementary to about 17 to about 39 consecutive nucleotides in a target RNA.

In some embodiments $N^1$ and $N^2$ form a Watson-Crick base pair. In some embodiments $N^1$ and $N^2$ form a non-Watson-Crick base pair. In some embodiments a base pair is formed between a ribonucleotide and a deoxyribonucleotide.

In some embodiments x=y=18, x=y=19 or x=y=20. In preferred embodiments x=y=18.

In some embodiments $N^1$ is covalently bound to (N)x and is mismatched to the target RNA. In various embodiments $N^1$ is covalently bound to (N)x and is a DNA moiety complementary to the target RNA.

In some embodiments $N^1$ is selected from adenosine, deoxyadenosine, deoxyuridine, ribothymidine or deoxythymidine, and wherein the nucleotide in the pairing nucleotide in the target RNA is adenosine. In preferred embodiments $N^1$ selected from adenosine, deoxyadenosine or deoxyuridine.

In some embodiments $N^1$ is selected from adenosine, deoxyadenosine, uridine, deoxyuridine, ribothymidine or deoxythymidine and wherein the nucleotide in the pairing nucleotide in the target RNA is cytidine. In preferred embodiments N1 is selected from adenosine, deoxyadenosine, uridine or deoxyuridine.

In some embodiments $N^1$ is selected from adenosine, deoxyadenosine, uridine, deoxyuridine, ribothymidine or deoxythymidine and wherein the nucleotide in the pairing nucleotide in the target RNA is guanosine.

In preferred embodiments $N^1$ is selected from adenosine, deoxyadenosine, uridine or deoxyuridine.

In some embodiments $N^1$ is selected from deoxyadenosine, deoxyuridine, ribothymidine or deoxythymidine and wherein the nucleotide in the pairing nucleotide in the target RNA is uridine. In preferred embodiments $N^1$ selected from deoxyadenosine or deoxyuridine.

In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

In some embodiments each of the sense strand and antisense strand is 19 nucleotides in length. In some embodiments N' in at least one of positions 11, 12, 13, 14, 15, 16, 17, 18, or 19 from the 5' terminus of the sense strand [(N')y in Structure A1 or $N^2$-(N')y in Structure A2] comprises a TNA moiety. In some embodiments a TNA moiety is present in the 3' terminal position of the sense strand. In some embodiments a TNA moiety is present in the 3' terminal position and the 3' penultimate position of the sense strand. In some embodiments a TNA moiety is present in the three 3' terminal positions of the sense strand. In some embodiments a TNA moiety is present in the four 3' terminal positions of the sense strand. In some embodiments a TNA moiety is present in the five 3' terminal positions of the sense strand. In some embodiments a TNA moiety is present in the six 3' terminal positions of the sense strand. In some embodiments a TNA moiety is present in the seven 3' terminal positions of the sense strand. In some embodiments a TNA moiety is present in the eight 3' terminal positions of the sense strand. In some embodiments a TNA moiety is present in the nine 3' terminal positions of the sense strand.

In some embodiments a TNA moiety is present in the ten 3' terminal positions of the sense strand.

In some embodiments the sense strand comprises 2, 3, 4, 5, 6, 7, 8, 9, or 10 TNA moieties. In some embodiments the sense strand comprises 2, 3, 4, 5, 6, 7, 8, 9, or 10 consecutive TNA moieties.

In some embodiments the presence of a TNA moiety in the sense strand increases resistance of the sense strand to nuclease activity. In other embodiments the presence of a TNA moiety in the sense strand of a dsRNA compound increases resistance of the dsRNA compound to nuclease activity. In other embodiments the presence of a TNA moiety in the sense strand of a dsRNA compound increases activity of the dsRNA compound.

In some embodiments of the double stranded nucleic acid molecules N in at least one of positions 5, 6, 7, 8, or 9 from the 5' terminus of the antisense strand [(N)x or $N^1$-(N)x] comprises a threose nucleic acid (TNA) moiety. In some embodiments of the double stranded nucleic acid molecules, N in at least one of positions 5, 6, 7, 8, or 9 from the 5' terminus of the antisense strand [(N)x or $N^1$-(N)x] comprises a 2'5' nucleotide or a mirror nucleotide or a combination thereof. Without wishing to be bound to theory, a double stranded nucleic acid molecule having a threose nucleic acid (TNA) moiety, a 2'5' nucleotide, a mirror nucleotide at any one or more of the aforementioned positions confers increased on target activity and/or decreased off target activity and/or decreased immunogenicity and/or increased stability to nucleases.

In some embodiments the antisense strand [(N)x of Structure A1 or $N^1$-(N)x of Structure A2] comprises a TNA moiety in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments the antisense strand [(N)x of Structure A1 or $N^1$-(N)x of Structure A2] comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments the antisense strand [(N)x of Structure A1 or $N^1$-(N)x of Structure A2] comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments of the double stranded nucleic acid molecules, N' in at least one of positions 9 or 10 from the 5' terminus of the sense strand [(N')y in Structure A1 or $N^2$-(N')y in Structure A2] is selected from a threose nucleic acid (TNA) moiety, a 2'5' nucleotide, a pseudoUridine or a combination thereof. Without wishing to be bound to theory, a double stranded nucleic acid molecule having a threose nucleic acid (TNA) moiety, at any one or more of positions 9 or 10 in the sense (passenger) strand confers increased on target activity and/or increased nuclease stability to the compound. Without wishing to be bound to theory, a double stranded nucleic acid molecule having a threose nucleic acid (TNA) moiety in the sense or antisense strand and further comprising a TNA, a 2'5' nucleotide, or a pseudoUridine at any one or more of positions 9 or 10 in the sense (passenger) strand confers increased on target activity and/or increased nuclease stability.

In some embodiments (N')y in Structure A1 or N²-(N')y in Structure A2 comprises a threose nucleic acid (TNA) moiety in position 9, or in position 10 or in positions 9-10.

In some embodiments (N')y in Structure A1 or N²-(N')y in Structure A2 comprises a 2'5' nucleotide in position 9, or in position 10 or in positions 9-10.

In some embodiments (N')y in Structure A1 or N²-(N')y in Structure A2 comprises a pseudoUridine in position 9, or in position 10 or in positions 9-10.

In some embodiments the sense strand comprises Z'. In some embodiments Z' comprises a C3 moiety (for example C3Pi, C3-OH, C3Pi-C3Pi, C3Pi-C3OH) or a 3' terminal phosphate (Pi). In some embodiments the antisense strand comprises Z. In some embodiments Z comprises a C3 moiety (for example C3Pi, C3-OH, C3Pi-C3Pi, C3Pi-C3OH) or a 3' terminal phosphate (Pi).

In another aspect provided are pharmaceutical compositions comprising a molecule according to Structure (A1) or (A2), in an amount effective to inhibit mammalian or non-mammalian gene expression; and a pharmaceutically acceptable carrier. In some embodiments the mammalian gene is a human gene. In some embodiments the non-mammalian gene is involved in a mammalian disease, preferably human disease.

Further provided are methods for treating or preventing the incidence or severity of a disease or condition and/or for reducing the risk or severity of a disease or condition in a subject in need thereof wherein the disease or condition and/or a symptom and/or risk associated therewith is associated with expression of a mammalian or a non-mammalian gene. In a preferred embodiment the subject is a human subject.

BRIEF DESCRIPTION OF THE FIGURES

FIGS. 5A-5E show stability, on-target activity, off-target activity and immune response data, respectively, for dsRNA molecules targeting MYD88 and comparing TNA. FIGS. 5A and 5B shows stability of sense strand and antisense strands in HCT116 cytosolic extract and human plasma as analyzed by gel electrophoresis. FIG. 5C shows on-target activity (knock down of MYDD88 mRNA). FIG. 5D shows off-target activity as analyzed in the psiCHECK system. FIG. 5E provides immune stimulation data of several molecules in comparison to Poly I:C and CL075.

FIGS. 6B-6F show TNA modified dsRNAs are stable for at least 24 hours whereas a compound that includes 2'OMe modified ribonucleotides on both strands is stable for less than 30 min. (FIG. 6A). STRUC2_S1322 sense strand includes 2'OMe sugar modified ribonucleotides in positions 2, 4, 6, 8, 10, 12, 14, 16, 18 and a 3' terminal dTdT; the antisense strand includes 2'OMe sugar modified ribonucleotides in positions 2, 4, 6, 7, 9, 11, 16-19 and a 3' terminal dTdT. STRUC2_S1315, STRUC2_S1316, STRUC2_S1317, STRUC2_S1318, and STRUC2_S1319 have the same an antisense strand as STRUC2_S1322. STRUC2_S1315 sense strand includes TNA in positions 15-19; STRUC2_S1316 sense strand includes TNA in positions 14-19, STRUC2_S1317 sense strand includes TNA in positions 13-19, STRUC2_S1318 sense strand includes TNA in positions 12-19, and STRUC2_S1319 sense strand includes TNA in positions 11-19.

Figure 1:
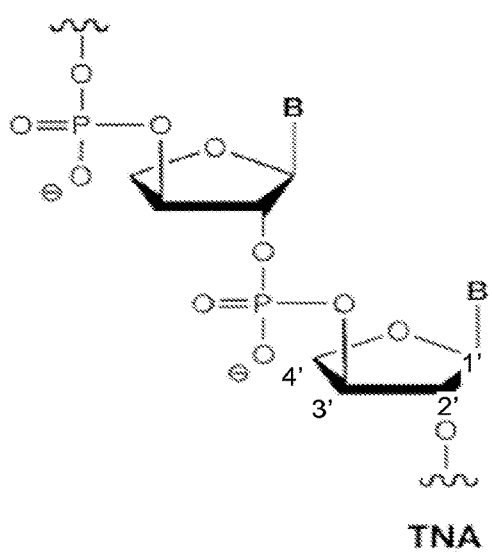
FIG. 1 shows the chemical structure of a TNA dimer compared to a RNA dimer. TNA is coupled to another TNA via the 2' and 3' positions of the threofuranose ring as opposed to the 3' and 5' positions of the sugar ring in DNA and RNA.
Figure 1:
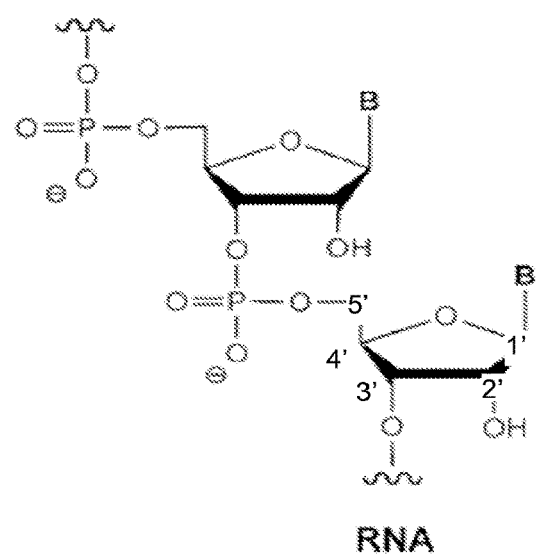
Figure 2:
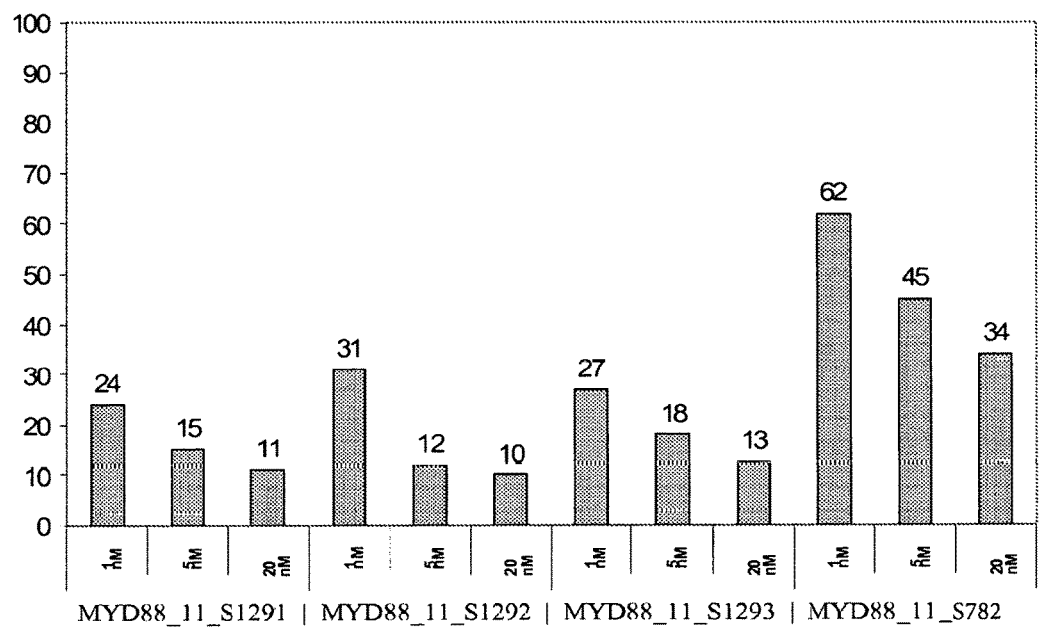
FIG. 2 shows activity of three chimeric dsRNA compounds that include RNA and TNA moieties on the sense strand compared to similar dsRNA compound with an unmodified ribonucleotide sense strand. MYD88_11_S1291, MYD88_11_S1292, MYD88_11_S1293 and MYD88_11_S782 are 19 mer double stranded compound with the same antisense strand based paired to different sense strands. The shared antisense strand includes 2'OMe sugar modified ribonucleotides in positions 2, 4, 6, 8, 11, 13, 15, 17, and 19 (5'>3') and MYD88_11_S1291 includes TNA moieties in positions 14, 16-19; MYD88_11_S1292 includes TNA moieties in positions 13, 14, 16-19; MYD88_11_S1293 includes TNA moieties in positions 12-14, 16-19.
Figure 3A:
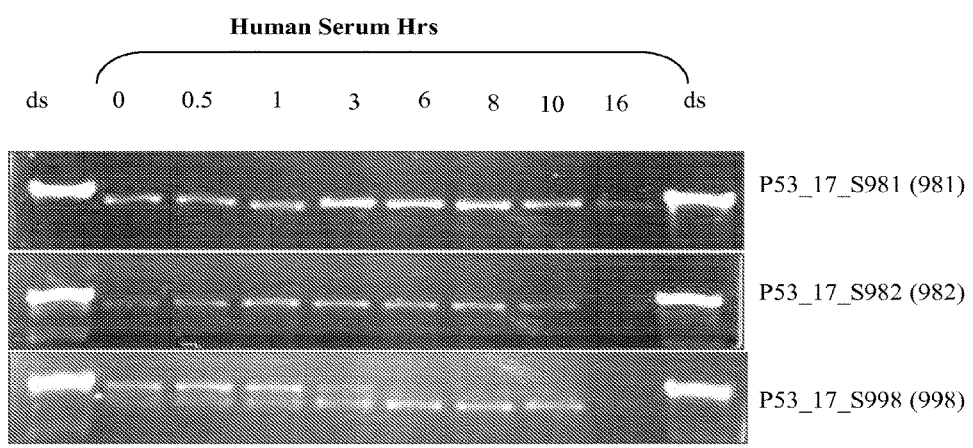
FIGS. 3A and 3B show human serum stability (in hours) of the dsRNA compounds including TNA moieties. P53_17_S981 (981), P53_17_S982 (982) and P53_17_S998 (998) share the same antisense strand. The shared antisense strand includes 2'OMe sugar modified ribonucleotides in positions 1, 3, 5, 7, 9, 11, 13, 15, 17, and 19 (5'>3') and P53_17_S981 includes TNA moieties in positions 15-19; P53_17_S982 includes TNA moieties in positions 13, 15-19; P53_17_S98 includes unmodified ribonucleotide sense strand. Ethidium bromide staining (FIG. 4A) shows that the dsRNA comprising the TNA moieties are stable in 100% human serum for at least 16 hours while the dsRNA comprising an unmodified sense strand is stable for less than 30 min (0.5 hr). The dsRNA were also loaded on a denaturing gel and sense and antisense strands were detection by labeled probes (4B). The results indicate that the sense strand modified with TNA is protected from cleavage in human serum.
Figure 3B:
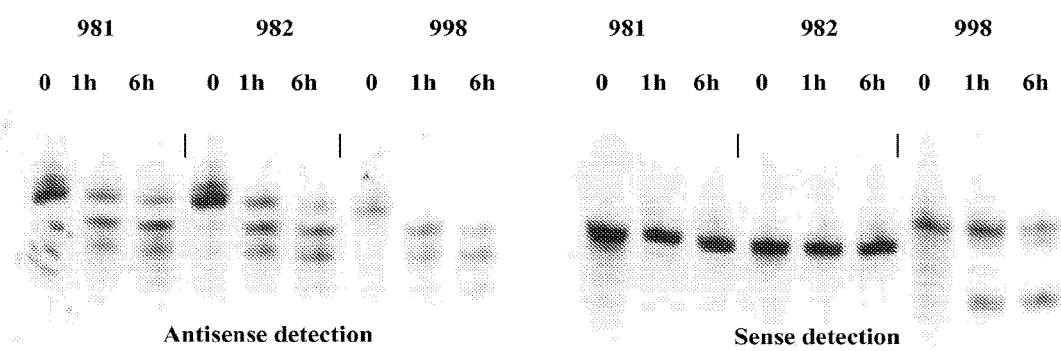
Figure 4A:
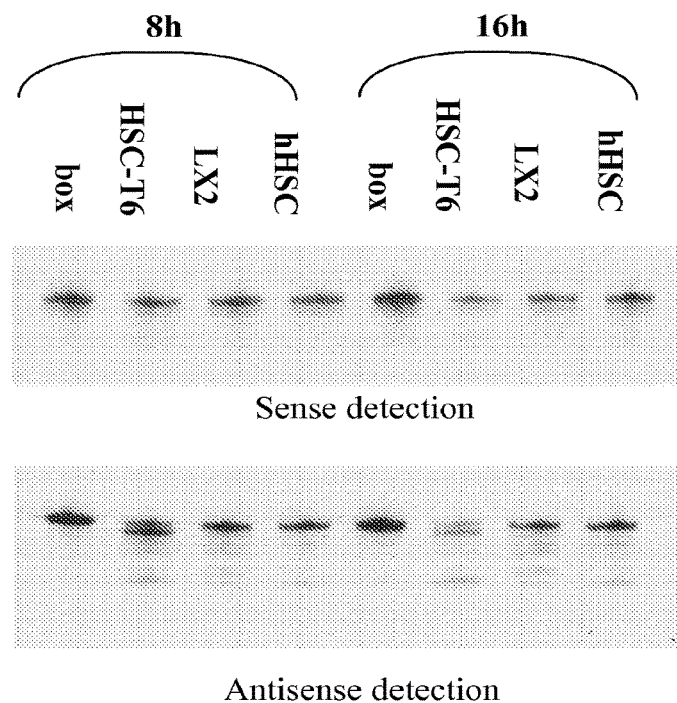
FIGS. 4A and 4B show stability of TNA modified dsRNA in cell extracts, HSC-T16 (immortalized rat liver stellate cells), LX2 (human hepatic stellate cell line derived from normal human stellate cells) and hHSC (human hepatic stellate cell line). MYD88_11_S1297 and MYD88_11_S889 share an antisense strand which includes 2'OMe sugar modified ribonucleotides in positions 3, 5, 7, 9, 11, 13, 15, 17, and 19 and a 3' terminal dTdT overhang (5'>3'). MYD88_11_S1297 sense strand includes TNA moieties in positions 13-14 and 16-19; MYD88_11_S889 sense strand comprising unmodified ribonucleotides. The MYD88_11_S1297 sense strand exhibits increased cell extract stability when compared to MYD88_11_S889.
Figure 4B:
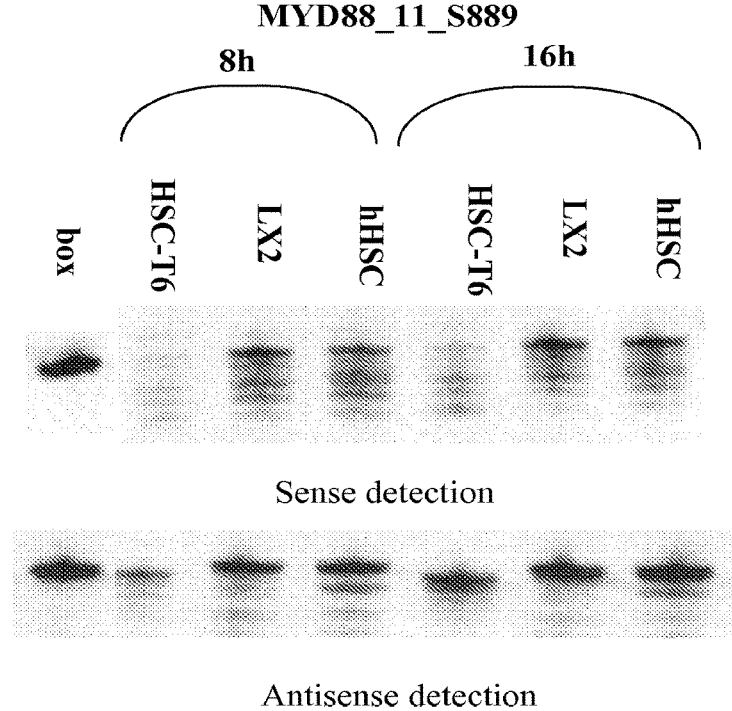
Figure 5A:
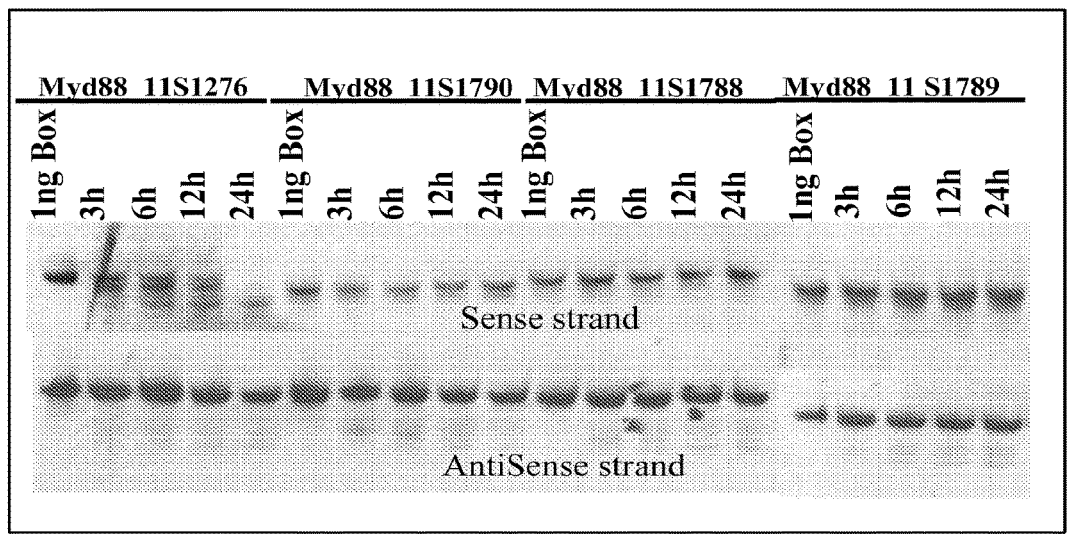
Figure 5B:
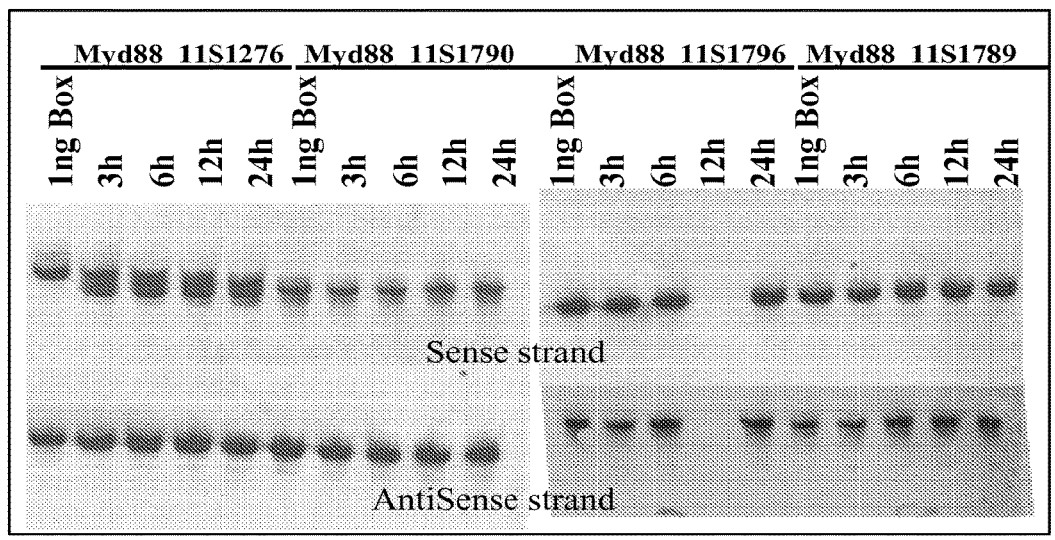
Figure 5C:
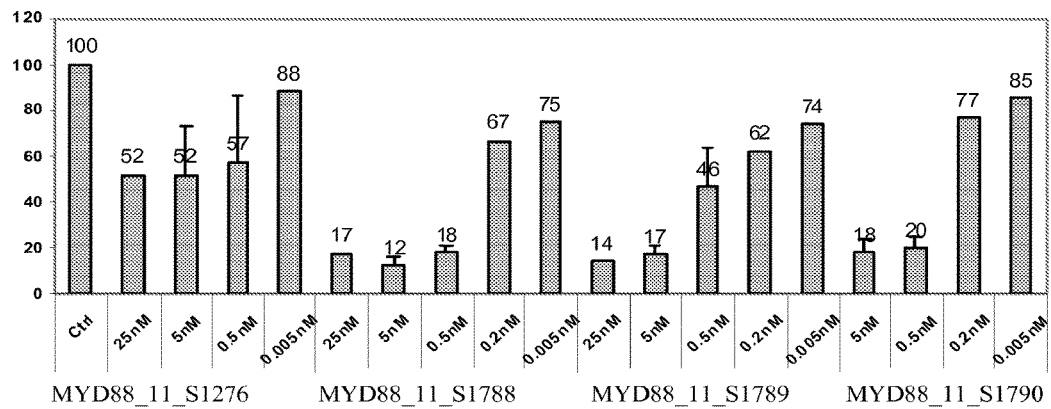
Figure 5D:
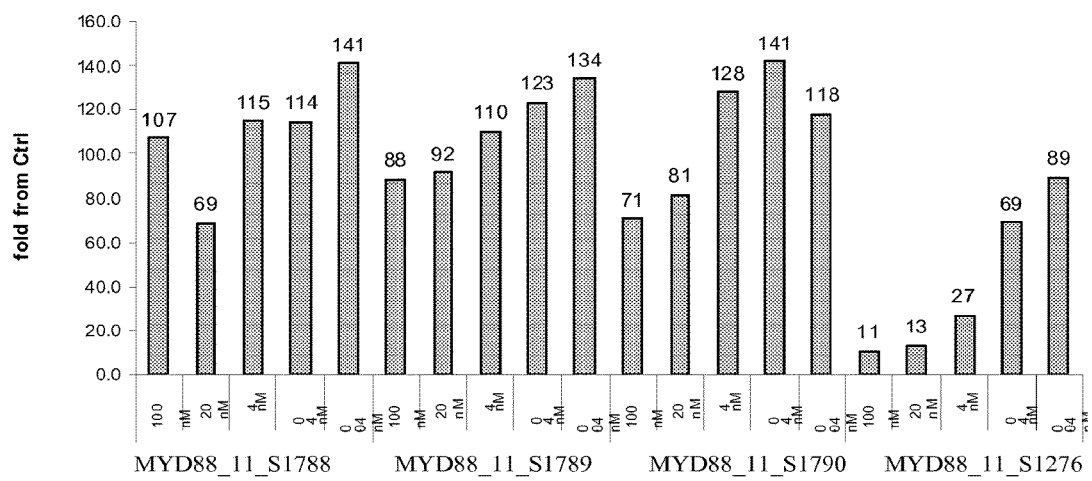
Figure 6A:
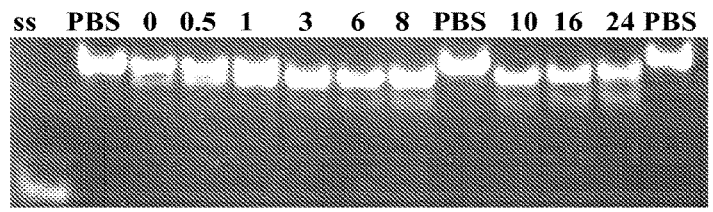
FIGS. 6A-6F show stability of TNA modified dsRNA compounds in human serum on an ethidium bromide stained gel.
Figure 6B:
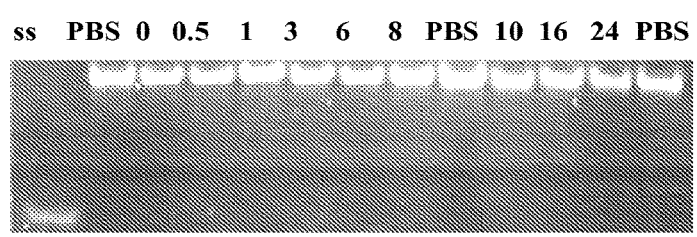
Figure 6C:
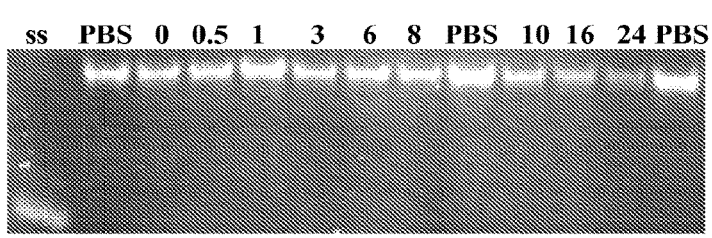
Figure 6D:
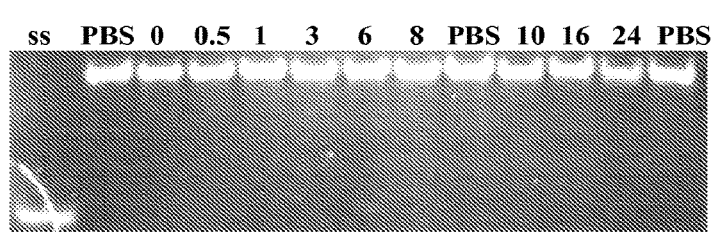
Figure 6E:
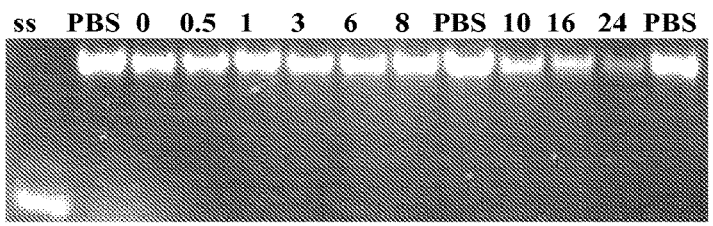
Figure 6F:
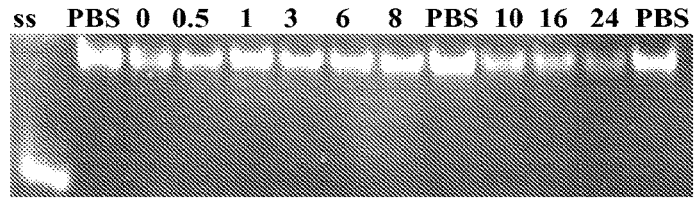

The compounds, methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

DETAILED DESCRIPTION OF THE INVENTION

The present invention relates generally to oligonucleotide compounds which down-regulate expression of various genes, particularly to small interfering RNAs (siRNA), specifically to modified dsRNA molecules and to the use of these modified dsRNA molecules in preparation of pharmaceutical compositions and in treatment of a subject suffering from various medical conditions. The double stranded nucleic acid molecules disclosed herein exhibit one or more of increased on-target activity, decreased off-target activity, increased nuclease stability (exonuclease and or endonuclease), and reduced immunomodulation when compared to an unmodified double stranded nucleic acid compound.

The compounds and compositions are able to knock down, attenuate, reduce or inhibit target gene expression and are useful in the treatment of subjects suffering from diseases or conditions and or symptoms associated with such diseases or conditions or at risk of contracting diseases or conditions in which gene expression has adverse consequences.

Accordingly, in certain aspects modified dsRNA molecules and pharmaceutical compositions comprising same useful in down regulating gene expression are provided. The target gene is a mammalian or non-mammalian target gene.

DEFINITIONS

It is to be noted that, as used herein, the singular forms "a", "an" and "the" include plural forms unless the content clearly dictates otherwise. Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein refers to a siRNA inhibitor. A "siRNA inhibitor" is a compound that is capable of reducing the expression of a gene or the activity of the product of such gene to an extent sufficient to achieve a desired biological or physiological effect. The term "siRNA inhibitor" as used herein refers to one or more of a siRNA, shRNA, siNA, synthetic shRNA; miRNA. Inhibition may also be referred to as down-regulation or, for RNAi, silencing.

A "compound" and a "molecule" are used interchangeably herein when referring to the dsRNA.

The term "inhibit" as used herein refers to reducing the expression of a gene or the activity of the product of such gene to an extent sufficient to achieve a desired biological or physiological effect. Inhibition is either complete or partial A "siNA inhibitor" "dsRNA inhibitor" "dsRNA molecule" is a compound which is capable of reducing the expression of a gene or the activity of the product of such gene to an extent sufficient to achieve a desired biological or physiological effect. The term "siNA inhibitor" as used herein refers to one or more of a siRNA, shRNA, synthetic shRNA; miRNA. Inhibition may also be referred to as down-regulation or, for RNAi, silencing. The dsRNA molecule includes a sense strand, also known as a passenger strand, which shares homology to a target RNA; and an antisense strand, also known as a guide strand, which is fully or partially complementary to the sense strand.

As used herein, the term "inhibition" of a target gene means inhibition of gene expression (transcription or translation) or polypeptide activity. The polynucleotide sequence of the target RNA sequence, refers to a mRNA target, a RNA target or any homologous sequences thereof preferably having at least 70% identity, more preferably 80% identity, even more preferably 90% or 95% identity to the target mRNA or RNA. Therefore, polynucleotide sequences, which have undergone mutations, alterations or modifications as described herein are encompassed in the present invention. The terms "mRNA polynucleotide sequence" and "mRNA" are used interchangeably.

"Gene product" as used herein, refers to a product of a gene such as an RNA transcript or a polypeptide. The terms "RNA transcript", "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this disclosure, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides, nucleotide analogues, modified nucleotide analogues, unconventional and abasic moieties and combinations thereof.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

"Nucleotide" is meant to encompass deoxyribonucleotides and ribonucleotides, which may be natural or synthetic and modified or unmodified. Nucleotides include known nucleotide analogues, which are synthetic, naturally occurring, and non-naturally occurring. Examples of such analogs include, without limitation, phosphorothioates, phosphoramidites, methyl phosphonates, chiral-methyl phosphonates, 2'-O-methyl ribonucleotides, and peptide-nucleic acids (PNAs). Modifications include changes to the sugar moiety, the base moiety and or the linkages between ribonucleotides in the oligoribonucleotide. As used herein, the term "ribonucleotide" encompasses natural and synthetic, unmodified and modified ribonucleotides and ribonucleotide analogues which are synthetic, naturally occurring, and non-naturally occurring. Modifications include changes to the sugar moiety, to the base moiety and/or to the linkages between ribonucleotides in the oligonucleotide.

The nucleotides are selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halouracil, 5-halocytosine, 6-azacytosine and 6-az thymine, pseudouracil, deoxypseudouracil, 4-thiouracil, ribo-2-thiouridine, ribo-4-thiouridine, 8-haloadenine, 8-aminoadenine, 8-thioladenine, 8-thiolalkyl adenines, 8-hydroxyl adenine and other 8-substituted adenines, 8-haloguanines, 8-aminoguanine, 8-thiolguanine, 8-thioalkylguanines 8-hydroxylguanine and other substituted guanines, other aza and deaza adenines, other aza and deaza guanines, 5-methylribouridine, 5-trifluoromethyl uracil, 5-methylribocytosine, and 5-trifluorocytosine. In some embodiments one or more nucleotides in an oligomer is substituted with inosine.

In some embodiments the siRNA compound further comprises at least one modified ribonucleotide selected from the group consisting of a ribonucleotide having a sugar modification, a base modification or an internucleotide linkage modification and may contain DNA, and modified nucleotides such as LNA (locked nucleic acid), ENA (ethylene-bridged nucleic acid), L-DNA or L-RNA, PNA (peptide nucleic acid), arabinoside, phosphonocarboxylate or phosphinocarboxylate nucleotide (PACE nucleotide), or nucleotides with a 6 carbon sugar.

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenosine 3' phosphonoacetate, deoxyribocytidine 3' phosphonoacetate, deoxyriboguanosine 3' phosphonoacetate, deoxyribothymidine 3' phosphonoacetate).

Bridged nucleic acids include LNA (2'-O, 4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

All analogs of, or modifications to, a nucleotide/oligonucleotide are employed with the present invention, provided that said analog or modification does not substantially adversely affect the properties, e.g. function, of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy (e.g. methoxy), alkyl, amino, fluoro, chloro, bromo, CN, CF, imidazole, carboxylate, thioate, C1 to C10 lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 0 586 520 B1 or EP 0 618 925 B1.

In one embodiment the modified siRNA compound comprises at least one ribonucleotide comprising a 2' modification on the sugar moiety ("2' sugar modification"). In certain embodiments the siRNA compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy) sugar modification.

In some embodiments the backbone of the oligonucleotides is modified and comprises phosphate-D-ribose entities but may also contain thiophosphate-D-ribose entities, triester, thioate, 2'-5' bridged backbone (also may be referred to as 2'5' nucleotide or 5'-2'), PACE and the like.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me riboU, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments the non-base pairing nucleotide analog is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have enhanced stability in vivo and in vitro. Other modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

"TNA" refers to (L)-alpha-threofuranosyl nucleotides. The TNA phosphoramidites are linked to adjacent TNA, deoxyribonucleotide or ribonucleotide by (3'→2') phosphodiester linkages. TNA comprise a four-carbon sugar (Schoning, et al Science 2000. 290:1347-51). In some embodiments, in addition to TNA the siRNA compound further comprises at least one modified ribonucleotide selected from the group consisting of a ribonucleotide having a sugar modification, a base modification or an internucleotide linkage modification and may contain DNA, a mirror nucleotide (L-DNA, L-RNA) and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), or nucleotides with a 6 carbon sugar.

In some embodiments the compounds of the present invention are synthesized with one or more inverted nucleotides, for example inverted thymidine or inverted adenosine (see, for example, Takei, et al., 2002, JBC 277(26):23800-06).

Other modifications include 3' terminal modifications also known as capping moieties. Such terminal modifications are selected from a nucleotide, a modified nucleotide, a lipid, a peptide, a sugar and inverted abasic moiety. Such modifications are incorporated, for example at the 3' terminus of the sense and/or antisense strands.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'O-Me nucleotide; and nucleotide analogs including 4',5'-methylene nucleotide; 1-(β-D-erythrofuranosyl)nucleotide; 4'-thionucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain preferred capping moieties are abasic ribose or abasic deoxyribose moieties; inverted abasic ribose or abasic deoxyribose moieties; C6-amino-Pi; a mirror nucleotide including L-DNA and L-RNA.

A "hydrocarbon moiety or derivative thereof" refers to straight chain or branched alkyl moieties and moieties per se or further comprising a functional group including alcohols, phosphodiester, phosphorothioate, phosphonoacetate and also includes amines, carboxylic acids, esters, amides aldehydes. "Hydrocarbon moiety" and "alkyl moiety" are used interchangeably.

"Terminal functional group" includes halogen, alcohol, amine, carboxylic, ester, amide, aldehyde, ketone, ether groups.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; an threose nucleic acid (TNA) moiety; bridged nucleic acids including locked nucleic acids (LNA) and ethylene bridged nucleic acids (ENA).

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouridine-3'-phosphate (mirror dU).

According to one aspect the present invention provides inhibitory modified dsRNA molecules comprising unmodified ribonucleotides, modified ribonucleotides and/or unconventional moieties. In some embodiments the modified siRNA compound comprises at least one modified nucleotide selected from the group consisting of a sugar modification, a base modification and an internucleotide linkage modification and may contain modified nucleotides such as LNA (locked nucleic acid) including ENA (ethylene-bridged nucleic acid; PNA (peptide nucleic acid); arabinoside; PACE (phosphonoacetate and derivatives thereof), or nucleotides with a six-carbon sugar or an unconventional moiety selected from an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond. In some embodiments a modified ribonucleotide is a 2'OMe sugar modified ribonucleotide. In some embodiments some or all of the pyrimidines in the antisense strand comprise 2'OMe sugar modified ribonucleotides. In some embodiments some or all of the purines in the antisense strand comprise 2'OMe sugar modified ribonucleotides. In preferred embodiments the antisense strand comprises 2'OMe sugar modified ribonucleotides in nuclease sensitive positions. In some embodiments the sense strand comprises 2'OMe sugar modified ribonucleotides in nuclease sensitive positions. In some embodiments the sense strand [(N')y in Structure A1 or $N^2$-(N')y] comprises one or more 2'OMe sugar modified ribonucleotides. In some embodiments the sense strand [(N')y in Structure A1 or $N^2$-(N')y] comprises one or more deoxyribonucleotide. In some embodiments the siRNA is blunt ended at the 3' terminus of the compound, i.e. the dsRNA or siRNA is blunt ended on the end defined by the 3'-terminus of the sense or passenger strand and the 5'-terminus of antisense or guide strand.

In other embodiments at least one of the two strands has a 3' overhang of at least one nucleotide at the 3'-terminus; the overhang comprises at least one deoxyribonucleotide. At least one of the strands optionally comprises an overhang of at least one nucleotide at the 3'-terminus. The overhang consists of from about 1 to about 5 nucleotides.

In various embodiments the overhangs are independently selected from a nucleotide, a non-nucleotide and a combination thereof. In certain embodiments, each overhang, if present, is independently selected from a ribonucleotide, deoxyribonucleotide, abasic deoxyribose moiety, abasic deoxyribose moiety, C3-amino-Pi, C4-amino-Pi, C5-amino-Pi, C6-amino-Pi, a mirror nucleotide.

In some embodiments each of Z and/or Z' independently includes a C2, C3, C4, C5 or C6 alkyl moiety, optionally a C3 [propane, —$(CH2)_3$-] moiety or a derivative thereof including propanol (C3-OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In a specific embodiment x=y=19 and Z comprises C3-C3. In some embodiments the C3-C3 overhang is covalently attached to the 3' terminus of (N)x or (N')y via a covalent linkage, for example a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH.

In various embodiments the alkyl moiety comprises an alkyl derivative including a C3 alkyl, C4 alkyl, C5 alkyl or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof.

The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate.

The structures of exemplary 3' terminal C3 non-nucleotide moieties are as follows:

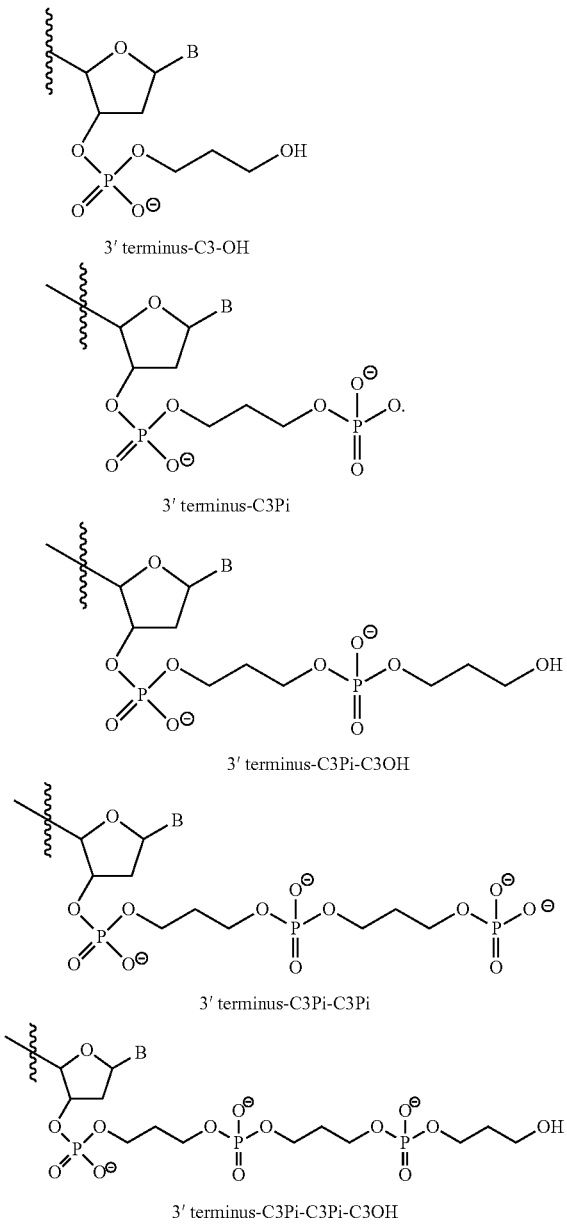

3' terminus-C3-OH

3' terminus-C3Pi

3' terminus-C3Pi-C3OH

3' terminus-C3Pi-C3Pi

3' terminus-C3Pi-C3Pi-C3OH

In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments, when the 3' terminal nucleotide comprises a 2'5' nucleotide the C3 moiety may be linked to the 2' position of the sugar via a phosphodiester linkage or other linkage.

In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)₃, (propyl phosphate)₂-propanol, (propyl phosphate)₂-propyl phosphorothioate. Any propane or propanol conjugated moiety can be included in Z or Z'.

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3Pi-rAb or C3Pi-dAb.

The length of the RNA duplex is from about 18 to about 40 ribonucleotides, or about, 18, 19, 20, 21, 22, 23, 24, 25, 26, 27, 28, 29, 30, 31, 32, 33, 34, 35, 36, 37, 38, 39, or 40, preferably 19 to 23 ribonucleotides. In some embodiments the length of each strand (oligomer) is independently selected from the group consisting of about 18 to about 40 bases, preferably 18 to 25 bases or 19-21 and more preferably 19 ribonucleotides.

In some embodiments, the complementarity between the antisense strand of the modified siRNA compound and the target nucleic acid is perfect. In other embodiments, the antisense strand of the modified siRNA compound and the target nucleic acid are substantially complementary, i.e. having one, two or up to three mismatches between said antisense strand and the target nucleic acid. In some embodiments the antisense strand is mismatched to the target mRNA at the 5' terminal nucleotide.

In certain embodiments the complementarity between the antisense strand and the sense strand of the modified siRNA compound of present invention is perfect. In some embodiments, the strands are substantially complementary, i.e. having one, two or up to three mismatches between said antisense strand and said sense strand. In some embodiments the antisense strand is fully complementary to the sense strand.

In some embodiments the modified dsRNA molecules disclosed herein exhibit enhanced activity, when compared to an siRNA compound wherein the antisense strand including the 5'-terminal nucleotide is fully complementary to a consecutive sequence in a target mRNA.

The siRNA structures of the present invention are beneficially applied to double stranded RNA useful in inhibiting or attenuating mammalian and non-mammalian gene expression.

dsRNA Oligonucleotides

In one aspect provided are double stranded nucleic acid molecules having structure (A1) set forth below:

(A1) 5' (N)x-Z 3' (antisense strand)
3' Z'-(N')y-z" 5' (sense strand)

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present independently includes 1-5 consecutive nucleotides or non-nucleotide moieties or a combination thereof covalently attached at the 3' terminus of the strand in which it is present;

wherein z" may be present or absent, but if present is a capping moiety covalently attached at the 5' terminus of (N')y;

wherein each of x and y is independently an integer between 18 and 25;

wherein the sequence of (N')y has complementarity to the sequence of (N)x and (N)x includes an antisense sequence to a target RNA; and wherein the double stranded nucleic acid comprises one or more of the following modifications
  a. a threose nucleic acid moiety, a 2'5' nucleotide or a mirror nucleotide in at least one of positions 5, 6, 7, 8, or 9 from the 5' terminus of the antisense strand (N)x;
  b. a threose nucleic acid moiety, a 2'5' nucleotide or a pseudoUridine in at least one of positions 9 or 10 from the 5' terminus of (N')y;
  c. 1, 2, 3, 4, 5, 6, 7, 8, 9 or 10 threose nucleic acid moieties or 2'5' nucleotides at the 3' terminal or penultimate positions of (N')y.

In some embodiments provided are double stranded nucleic acid molecules according to structure (A1) set forth below:

5' (N)x-Z 3' (antisense strand)
3' Z'-(N')y-z" 5' (sense strand)

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides or non-nucleotide moieties or a combination thereof covalently attached at the 3' terminus of the strand in which it is present;
wherein z" may be present or absent, but if present is a capping moiety covalently attached at the 5' terminus of (N')y;
wherein each of x and y is independently an integer between 18 and 25;
wherein the sequence of (N')y has complementarity to the sequence of (N)x and (N)x includes an antisense sequence to a target RNA; and
wherein a threose nucleic acid moiety, a 2'5' nucleotide or a mirror nucleotide is present in at least one of positions 5, 6, 7, 8, or 9 from the 5' terminus of (N)x.

In some embodiments provided are double stranded nucleic acid molecules according to structure (A1) set forth below:

5' (N)x-Z 3' (antisense strand)
3' Z'-(N')y-z" 5' (sense strand)

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides or non-nucleotide moieties or a combination thereof covalently attached at the 3' terminus of the strand in which it is present;
wherein z" may be present or absent, but if present is a capping moiety covalently attached at the 5' terminus of (N')y;
wherein each of x and y is independently an integer between 18 and 25;
wherein the sequence of (N')y has complementarity to the sequence of (N)x and (N)x includes an antisense sequence to a target RNA; and
wherein a threose nucleic acid moiety, a 2'5' nucleotide and a pseudoUridine is present in at least one of positions 9 or 10 from the 5' terminus of (N')y.

Further provided are double stranded nucleic acid molecules according to structure (A1) set forth below:

5' (N)x-Z 3' (antisense strand)
3' Z'-(N')y-z" 5' (sense strand)

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present independently includes 1-5 consecutive nucleotides or non-nucleotide moieties or a combination thereof covalently attached at the 3' terminus of the strand in which it is present;
wherein z" may be present or absent, but if present is a capping moiety covalently attached at the 5' terminus of (N')y;
wherein each of x and y is independently an integer between 18 and 25;
wherein the sequence of (N')y has complementarity to the sequence of (N)x and (N)x includes an antisense sequence to a target RNA; and
wherein 1, 2, 3, 4, 5, 6, 7, 8, 9, or 10 TNA moieties are present in positions at the 3' terminal or penultimate position positions of (N')y.

In some embodiments the double stranded molecule comprises a mismatch to the target mRNA according to structure A2:

5' $N^1$-(N)x-Z 3' (antisense strand)
3' Z'-$N^2$-(N')y-z" 5' (sense strand)

wherein each of $N^2$, N and N' is an unmodified or modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 24;
wherein the sequence of (N')y has complementarity to the sequence of (N)x and (N)x has complementarity to a consecutive sequence in a target RNA;
wherein $N^1$ is covalently bound to (N)x and is mismatched to the target RNA or is a complementary DNA moiety to the target RNA;
wherein $N^1$ is a moiety selected from the group consisting of natural or modified uridine, deoxyribouridine, ribothymidine, deoxyribothymidine, adenosine or deoxyadenosine;
wherein z" may be present or absent, but if present is a capping moiety covalently attached at the 5' terminus of $N^2$-(N')y; and
wherein each of Z and Z' is independently present or absent, but if present is independently 1-5 consecutive nucleotides, consecutive non-nucleotide moieties or a combination thereof covalently attached at the 3' terminus of the strand in which it is present; and
wherein a threose nucleic acid moiety, a 2'5' nucleotide or a mirror nucleotide is present in at least one of positions 5, 6, 7, 8, or 9 from the 5' terminus of (N)x.

In some embodiments the double stranded molecule comprises a mismatch to the target mRNA according to structure A2:

5' $N^1$-(N)x-Z 3' (antisense strand)
3' Z'-$N^2$-(N')y-z" 5' (sense strand)

wherein each of $N^2$, N and N' is an unmodified or modified ribonucleotide, or an unconventional moiety;
wherein each of (N)x and (N')y is an oligonucleotide in which each consecutive N or N' is joined to the adjacent N or N' by a covalent bond;

wherein each of x and y is independently an integer between 17 and 24;
wherein the sequence of (N')y has complementarity to the sequence of (N)x and (N)x has complementarity to a consecutive sequence in a target RNA;
wherein $N^1$ is covalently bound to (N)x and is mismatched to the target RNA or is a complementary DNA moiety to the target RNA;
wherein $N^1$ is a moiety selected from the group consisting of natural or modified uridine, deoxyribouridine, ribothymidine, deoxyribothymidine, adenosine or deoxyadenosine;
wherein z" may be present or absent, but if present is a capping moiety covalently attached at the 5' terminus of $N^2$-(N')y; and
wherein each of Z and Z' is independently present or absent, but if present is independently 1-5 consecutive nucleotides, consecutive non-nucleotide moieties or a combination thereof covalently attached at the 3' terminus of the strand in which it is present; and
wherein a threose nucleic acid moiety, a 2'5' nucleotide and a pseudoUridine is present in at least one of positions 9 or 10 from the 5' terminus of (N')y.

In some embodiments the double stranded molecule comprises a mismatch to the target mRNA according to structure A2:

5' $N^1$-(N)x-Z 3' (antisense strand)
3' Z'-$N^2$-(N')y-z" 5' (sense strand)

wherein each of $N^2$, N and N' is an unmodified or modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 24;
wherein the sequence of (N')y has complementarity to the sequence of (N)x and (N)x has complementarity to a consecutive sequence in a target RNA;
wherein N is covalently bound to (N)x and is mismatched to the target RNA or is a complementary DNA moiety to the target RNA;
wherein $N^1$ is a moiety selected from the group consisting of natural or modified uridine, deoxyribouridine, ribothymidine, deoxyribothymidine, adenosine or deoxyadenosine;
wherein z" may be present or absent, but if present is a capping moiety covalently attached at the 5' terminus of $N^2$-(N')y; and
wherein each of Z and Z' is independently present or absent, but if present is independently 1-5 consecutive nucleotides, consecutive non-nucleotide moieties or a combination thereof covalently attached at the 3' terminus of the strand in which it is present; and
wherein a 2'5' nucleotide is present in 4, 5, or 6 consecutive positions at the 3' terminal or penultimate position positions of (N')y.

In some embodiments of structures A1 or A2 the sequence of (N')y is fully complementary to the sequence of (N)x. In various embodiments of structure A1 and A2 sequence of $N^2$-(N')y is complementary to the sequence of N'-(N)x. In some embodiments (N)x comprises an antisense that is fully complementary to about 17 to about 24 consecutive nucleotides in a target RNA.

For structure A2, in some embodiments $N^1$ and $N^2$ form a Watson-Crick base pair. In some embodiments $N^1$ and $N^2$ form a non-Watson-Crick base pair. In some embodiments a base pair is formed between a ribonucleotide and a deoxyribonucleotide. In some embodiments x=y=18, x=y=19 or x=y=20. In preferred embodiments x=y=18. In some embodiments $N^1$ is covalently bound to (N)x and is mismatched to the target RNA. In various embodiments N' is covalently bound to (N)x and is a DNA moiety complementary to the target RNA.

In some embodiments $N^1$ is covalently bound to (N)x and is a DNA moiety complementary to the target RNA. In some embodiments $N^1$ is selected from adenosine, deoxyadenosine, deoxyuridine, ribothymidine or deoxythymidine, and wherein the nucleotide in the pairing nucleotide in the target RNA is adenosine. In preferred embodiments $N^1$ selected from adenosine, deoxyadenosine or deoxyuridine. In some embodiments $N^1$ is selected from adenosine, deoxyadenosine, uridine, deoxyuridine, ribothymidine or deoxythymidine and wherein the nucleotide in the pairing nucleotide in the target RNA is cytidine. In preferred embodiments $N^1$ is selected from adenosine, deoxyadenosine, uridine or deoxyuridine. In some embodiments $N^1$ is selected from adenosine, deoxyadenosine, uridine, deoxyuridine, ribothymidine or deoxythymidine and wherein the nucleotide in the pairing nucleotide in the target RNA is guanosine. In preferred embodiments N1 is selected from adenosine, deoxyadenosine, uridine or deoxyuridine.

In some embodiments $N^1$ is selected from deoxyadenosine, deoxyuridine, ribothymidine or deoxythymidine and wherein the nucleotide in the pairing nucleotide in the target RNA is uridine. In preferred embodiments $N^1$ selected from deoxyadenosine or deoxyuridine. In some embodiments $N^1$ and $N^2$ form a base pair between uridine or deoxyuridine, and adenosine or deoxyadenosine. In other embodiments $N^1$ and $N^2$ form a base pair between deoxyuridine and adenosine.

In some embodiments the double stranded nucleic acid molecule is a siRNA, siNA or a miRNA.

The following table, Table 1 provides examples of $N^1$ and corresponding $N^2$.

TABLE 1

| Target nucleotide | 5' terminal nucleotide of AS with full match to target | $N^1$ (5' terminal position of AS) | $N^2$ (3' terminal position of SEN) |
|---|---|---|---|
| A | U | rA, dA | rU, dU, rT, dT |
| A | U | dU, rT, dT | rA, dA |
| C | G | rA, dA | rU, dU, rT, dT |
| C | G | rU, dU, rT, dT | rA, dA |
| G | C | rA, dA | rU, dU, rT, dT |
| G | C | rU, dU, rT, dT | rA, dA |
| U | A | dA | rU, dU rT, dT |
| U | A | dU rT, dT | rA, dA |

In some embodiments of Structure A2, $N^1$ comprises uridine or adenosine. In certain embodiments $N^2$ comprises a 2'OMe sugar modified ribonucleotide. In some embodiments $N^1$ comprises 2'OMe sugar modified ribouridine and $N^2$ comprises adenosine or modified adenosine. In some embodiments $N^1$ comprises adenosine and $N^2$ comprises a ribouridine or modified ribouridine. In some embodiments Z and Z' are absent. In other embodiments one of Z or Z' is present.

In some embodiments each of N and N' is an unmodified ribonucleotide. In some embodiments at least one of N or N' comprises a chemically modified ribonucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' comprises a 2'OMe sugar-modified ribonucleotide.

In some embodiments the sequence of (N')y is fully complementary to the sequence of (N)x. In other embodiments the sequence of (N')y is substantially complementary to the sequence of (N)x.

Structures A1 and A2 are useful with any oligonucleotide pair (sense and antisense strands) to a mammalian or non-mammalian gene. In some embodiments the mammalian gene is a human gene.

In some embodiments a modified siRNA compound having structure A2 exhibits beneficial properties including enhanced activity (e.g. reduced IC50, increased knock down, reduced residual mRNA) when compared to a control compound, i.e. an siRNA compound wherein the antisense oligonucleotide is fully complementary (including 5' terminal nucleotide base paired e.g. A-U, U-A, C-G, G-C) to a nucleotide sequence in a target mRNA. In some embodiments the activity is enhanced by at least 5%, by at least 10%, by at least 20%, by at least 25% or more when compared to a control compound.

In another aspect the present invention provides a method of generating a double stranded RNA molecule consisting of a sense strand and an antisense strand comprising the steps of
a) selecting a consecutive 17 to 25 nucleotide sequence in a target RNA and synthesizing an antisense strand comprising complementarity to the consecutive 17 to 25 nucleotide sequence of the target mRNA wherein the 5' terminal nucleotide of the antisense strand is substituted with uridine, modified uridine, ribothymidine, deoxyribothymidine, adenosine, modified adenosine, deoxyadenosine or modified deoxyadenosine, with the proviso that a rG:rU wobble is not generated between the 5' terminal nucleotide of the antisense strand and the 3' terminal nucleotide of the target mRNA;
b) synthesizing a sense strand of 17 to 25 nucleotides having complementarity to the antisense strand, wherein the 3' terminal nucleotide of the sense strand forms a Watson Crick base pair with the 5' terminal nucleotide of the guide strand; and
c) annealing the antisense and sense strands; thereby generating a double stranded RNA molecule.

According to one embodiment provided is a method of generating a double stranded RNA molecule consisting of a sense strand and an antisense strand exhibiting enhanced RNAi activity when compared to an unmodified a double stranded RNA molecule comprising the steps of
a) selecting a consecutive 17 to 25 nucleotide sequence in a target mRNA and synthesizing a sense strand comprising the consecutive 17 to 25 nucleotide sequence of the target mRNA wherein the 3' terminal nucleotide is substituted with adenosine, modified adenosine, deoxyadenosine or modified deoxyadenosine;
b) synthesizing an antisense strand of 17 to 25 nucleotides having complementarity to the sense strand wherein the 5' terminal nucleotide comprises ribouridine, modified ribouridine, deoxyribouridine or modified deoxyribouridine and base pairs with the 3' terminal nucleotide of the passenger strand;
c) annealing the sense strand to the antisense strand; thereby generating a double stranded RNA molecule having enhanced RNAi activity.

In some embodiments the modified double stranded RNA molecule exhibits enhanced RNAi activity when compared to an unmodified siRNA duplex, i.e. a duplex having full match to the target mRNA.

According to another aspect, the present invention provides a method of generating a modified a double stranded RNA molecule consisting of a sense strand and antisense strand exhibiting enhanced RNAi activity when compared to an unmodified a double stranded RNA molecule comprising the steps of
a) selecting a consecutive 17 to 25 nucleotide sequence in a target mRNA and synthesizing a sense strand comprising the consecutive 17 to 25 nucleotide sequence of the target mRNA wherein the 3' terminal nucleotide is substituted with adenosine, modified adenosine, deoxyadenosine or modified deoxyadenosine;
b) synthesizing an antisense strand of 17 to 25 nucleotides having complementarity to the sense strand wherein the 5' terminal nucleotide comprises ribouridine, modified ribouridine, deoxyribouridine or modified deoxyribouridine and base pairs with the 3' terminal nucleotide of the sense strand;
c) annealing the sense strand to the antisense strand; thereby generating a double stranded RNA molecule having enhanced RNAi activity.

In some embodiments step a) includes selecting a consecutive 17 to 25 nucleotide, or 17, 18, 19, 20, 21, 22, 23, 24 or 25 nucleotide sequence in a target RNA in a target cell wherein the 3' terminal nucleotide is other than adenosine.

In some embodiments Z and Z' are absent. In other embodiments one of Z or Z' is present. In various embodiments Z and Z' are independently selected from a nucleotide, a non-nucleotide and a combination thereof. In certain embodiments, each of Z and Z', if present, is independently selected from a ribonucleotide, deoxyribonucleotide, abasic deoxyribose moiety, abasic deoxyribose moiety, C3-amino-Pi, C4-amino-Pi, C5-amino-Pi, C6-amino-Pi, a mirror nucleotide. In some embodiments Z is present. In other embodiments Z' is present. In additional embodiments both Z and Z' are present. In some embodiments Z and Z' are present and are identical. In further embodiments Z and Z' are present and are different. In some embodiments Z and Z' are independently 1, 2, 3, 4 or 5 non-nucleotide moieties or a combination of 2, 3, 4, or 5 non-nucleotide moieties and nucleotides. In some embodiments each of Z and or Z' comprises 2 non-nucleotide moieties covalently linked to the 3' terminus of the siRNA strand via a phosphodiester bond. In some embodiments Z and Z' are present and each one independently comprises one or more alkyl moieties and or derivative thereof. In some embodiments, $N^2$ comprises riboadenosine and $N^1$ comprises uridine (ribouridine).

A non-nucleotide moiety is selected from the group consisting of an abasic moiety, an inverted abasic moiety, an alkyl moiety or derivative thereof, and an inorganic phosphate. In some embodiments a non-nucleotide moiety is an alkyl moiety or derivative thereof. In some embodiments the alkyl moiety comprises a terminal functional group including alcohol, a terminal amine, a terminal phosphate or a terminal phosphorothioate moiety.

In some embodiments Z is present and comprises one or more non-nucleotide moieties selected from the group consisting of an abasic moiety, an inverted abasic moiety, hydrocarbon moiety or derivative thereof, and an inorganic phosphate. In some embodiments Z is present and comprises one or more alkyl moieties and or derivative thereof.

In additional embodiments Z' is present and comprises one or more non-nucleotide moieties selected from the group consisting of an abasic moiety, an inverted abasic moiety, a hydrocarbon moiety, and an inorganic phosphate. In some embodiments Z' is present and comprises one or more alkyl moieties and or derivative thereof.

In additional embodiments x=y=18 and either Z or Z' is present and independently comprises two non-nucleotide moieties, for example a C3Pi-C3Pi or C3Pi-C3OH.

In additional embodiments x=y=18 and Z and Z' are present and each independently comprises two non-nucleotide moieties, for example a C3Pi-C3Pi or C3Pi-C3OH.

In some embodiments each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb. Each moiety is covalently conjugated an adjacent moiety via a covalent bond, preferably a phospho-based bond. In some embodiments the phospho-based bond is a phosphorothioate, a phosphonoacetate or a phosphodiester bond.

In a specific embodiment of structure A1 x=y=19 and Z comprises C3Pi-C3OH or C3Pi-C3Pi. In a specific embodiment x=y=19 and Z' comprises C3Pi-C3OH or C3Pi-C3Pi. In some embodiments the C3-C3 overhang is covalently attached to the 3' terminus of (N)x or (N')y via covalent linkage, for example a phosphodiester linkage. In some embodiments the linkage between a first C3 and a second C3 is a phosphodiester linkage.

In a specific embodiment of structure A2 x=y=18 and Z comprises C3Pi-C3OH or C3Pi-C3Pi. In a specific embodiment x=y=18 and Z' comprises C3Pi-C3OH or C3Pi-C3Pi. In some embodiments the C3-C3 overhang is covalently attached to the 3' terminus of $N^1$-(N)x or $N^2$-(N')y via covalent linkage, for example a phosphodiester linkage. In some embodiments the linkage between a first C3 and a second C3 is a phosphodiester linkage.

In various embodiments the alkyl moiety is a C3 alkyl to C6 alkyl moiety comprising a terminal hydroxyl, a terminal amino, terminal phosphate group. In some embodiments the alkyl moiety is a C3 alkyl moiety. In some embodiments the C3 alkyl moiety comprises propanol, propylphosphate, propylphosphorothioate or a combination thereof.

The C3 alkyl moiety is covalently linked to the 3' terminus of (N')y and or the 3' terminus of (N)x via a phosphodiester bond. In some embodiments the alkyl moiety comprises propanol, propyl phosphate or propyl phosphorothioate.

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3-rAb or C3-dAb.

In preferred embodiments of structure A2 x=y=18, Z' is absent, Z is present and comprises two alkyl moieties covalently linked to each other via a phosphodiester bond, $N^2$ comprises riboadenosine and N' comprises uridine.

In some embodiments N and N' comprise an unmodified nucleotide. In some embodiments at least one of N or N' comprises a chemically modified ribonucleotide or an unconventional moiety. In some embodiments the unconventional moiety is selected from the group consisting of a mirror nucleotide, an abasic ribose moiety, an abasic deoxyribose moiety, a deoxyribonucleotide, a modified deoxyribonucleotide, a mirror nucleotide, a non-base pairing nucleotide analog, a bridged nucleic acid and a nucleotide joined to an adjacent nucleotide by a 2'-5' internucleotide phosphate bond. In some embodiments the unconventional moiety is a mirror nucleotide, preferably an L-DNA moiety.

In some embodiments at least one of N or N' is modified at one or more of the sugar, the base or linker. In certain embodiments at least one of N or N' comprises a 2'OMe sugar modified ribonucleotide.

In preferred embodiments the chemically modified ribonucleotides are positioned along the sense strand and or antisense strand modifications and effect a desired property upon the double stranded compound including increased on target activity and/or decreased off target activity and or increased stability to nucleases.

In some embodiments of the double stranded nucleic acid molecules of Structures A1 and A2, N in at least one of positions 5, 6, 7, 8, or 9 from the 5' terminus of (N)x or $N^1$-(N)x is selected from a threose nucleic acid (TNA) moiety, a 2'5' nucleotide, a mirror nucleotide or a combination thereof.

In some embodiments of Structure A1, x=19 and (N)x comprises a TNA moiety in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In some embodiments Structure A2 x=18 and $N^1$-(N)x of Structure A2 comprises a TNA moiety in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. $N^1$ is counted as position 1 of the antisense (guide) strand (5'>3').

In some embodiments of Structure A1 x=19 and (N)x comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In preferred embodiments (N)x comprises a 2'-5' nucleotide in position 5, in position 7, in position 8, in position 9, in positions 6-7, in positions 7-8, or in positions 8-9. In some embodiments of Structure A2 x=18 and $N^1$-(N)x comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In preferred embodiments $N^1$-(N)x comprises a 2'-5' nucleotide in position 5, in position 7, in position 8, in position 9, in positions 6-7, in positions 7-8, or in positions 8-9.

In some embodiments Structure A1 x=19 and (N)x comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9. In some embodiments (N)x of Structure A1 or $N^1$-(N)x of Structure A2 comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9 or in positions 5-9.

In some embodiments of the double stranded nucleic acid molecules, N' in at least one of positions 9 or 10 from the 5' terminus of (N')y in Structure A1 or $N^2$-(N')y in Structure A2 is selected from a threose nucleic acid (TNA) moiety, a 2'5' nucleotide, a mirror nucleotide or a combination thereof. Without wishing to be bound to theory, a double stranded nucleic acid molecule having a threose nucleic acid (TNA) moiety, a 2'5' nucleotide, or a pseudoUridine at one or both of positions 9 or 10 in the sense (passenger) strand confers increased on target activity and/or increased nuclease stability.

In some embodiments of Structure A1 (N')y comprises a threose nucleic acid (TNA) moiety in position 9, or in position 10 or in positions 9-10. In some embodiments of Structure A2 $N^2$-(N')y comprises a threose nucleic acid (TNA) moiety in position 9, or in position 10 or in positions 9-10.

In some embodiments of Structure A1 (N')y comprises a 2'5' nucleotide in position 9, or in position 10 or in positions 9-10. In some embodiments of Structure A2 $N^2$-(N')y comprises a 2'5' nucleotide in position 9, or in position 10 or in positions 9-10.

In some embodiments of Structure A1 (N')y comprises a mirror nucleotide in position 9, or in position 10 or in positions 9-10. In some embodiments of Structure A2 $N^2$-(N')y comprises a pseudoUridine in position 9, or in position 10 or in positions 9-10.

In some embodiments of the double stranded nucleic acid molecules, N' comprises 2'5' nucleotides at the 4 most, 5 most or 6 most 3' terminal positions of (N')y in Structure A1 or $N^2$-(N')y in Structure A2. Without wishing to be bound to theory, a double stranded nucleic acid molecule having multiple 2'5' nucleotides at the 3' terminus of the sense (passenger) strand confers increased nuclease stability to the duplex and or reduced off target effect of the sense (passenger) strand.

In some embodiments of Structure A1 (N')y comprises 2'5' nucleotides in the four 3'-most terminal positions. In some embodiments the x=y=19 and (N')y comprises 2'5' nucleotides in positions 16, 17, 18 and 19.

In some embodiments of Structure (A2) $N^2$-(N')y comprises 2'5' nucleotides in the four 3'-most terminal positions. In some embodiments the x=y=18 and $N^2$-(N')y comprises 2'5' nucleotides in positions 16, 17, 18 and 19.

In some embodiments of Structure A1 (N')y comprises 2'5' nucleotides in the five 3'-most terminal positions. In some embodiments the x=y=19 and (N')y comprises 2'5' nucleotides in positions 15, 16, 17, 18 and 19.

In some embodiments of Structure A2 $N^2$-(N')y comprises 2'5' nucleotides in the five 3'-most terminal positions. In some embodiments the x=y=18 and $N^2$-(N')y comprises 2'5' nucleotides in positions 15, 16, 17, 18 and 19.

In some embodiments of structure A1 (N')y comprises 2'5' nucleotides in the six 3'-most terminal positions. In some embodiments the x=y=19 and (N')y comprises 2'5' nucleotides in positions 14, 15, 16, 17, 18 and 19.

In some embodiments of structure A2 $N^2$-(N')y comprises 2'5' nucleotides in the six 3'-most terminal positions. In some embodiments the x=y=19 and $N^2$-(N')y comprises 2'5' nucleotides in positions 14, 15, 16, 17, 18 and 19.

In some embodiments the double stranded nucleic acid molecule is a siRNA, siNA or a miRNA.

The double stranded compounds may further comprise combinations of the aforementioned modifications, and 2'OMe sugar modified ribonucleotides including 2'OMe sugar modified pyrimidines and or purines in the sense strand and or antisense strand. In certain embodiments (N)x and (N')y are fully complementary. In other embodiments (N)x and (N')y are substantially complementary. In certain embodiments (N)x is fully complementary to a target sequence. In other embodiments (N)x is substantially complementary to a target sequence. According to certain preferred embodiments the present invention provides a modified siRNA compound comprising one or more modified nucleotide, wherein the modified nucleotide possesses a modification in the sugar moiety, in the base moiety or in the internucleotide linkage moiety.

In certain embodiments of the compound according to Structures A1 and A2 alternating ribonucleotides in each of $(N)_x$ and $(N')_y$ are 2'-OMe sugar modified ribonucleotides. In some embodiments in (N)x the nucleotides are unmodified or (N)x comprises alternating 2'OMe sugar modified ribonucleotides and unmodified ribonucleotides; and the ribonucleotide located at the middle position of $N^1$-(N)x being modified or unmodified preferably unmodified; wherein (N')y comprises unmodified ribonucleotides further comprising one modified nucleotide at a terminal or penultimate position.

In particular embodiments of Structure A1, x=y=19, $N^1$ comprises an unmodified ribonucleotide, (N)x comprises 2'OMe sugar modified ribonucleotides and the ribonucleotide located at the middle of $N^1$-(N)x is unmodified. In certain embodiments x=y=19; in (N)x the nucleotides alternate between modified ribonucleotides and unmodified ribonucleotides, each modified ribonucleotide is a 2'OMe sugar modified ribonucleotide and the ribonucleotide located at the middle position of $N^1$-(N)x being unmodified; $N^2$ is joined to the 3' terminus of (N')y by a 2'-5' phosphodiester bond and at least three nucleotides at the 3' terminus of (N')y are 2'-5' nucleotides (covalently linked by 2'5' phosphodiester bonds). In other preferred embodiments, x=y=19; in (N)x the nucleotides alternate between modified ribonucleotides and unmodified ribonucleotides, each modified ribonucleotide is a 2'-OMe sugar modified ribonucleotide and the ribonucleotide located at the middle of $N^1$-(N)x being unmodified; and five consecutive nucleotides at the 3' terminus of (N')y are 2'5' ribonucleotides (joined by four 2'-5' phosphodiester bonds). In some embodiments one or more of the 2'5' ribonucleotides comprise 3'-OMe sugar modification.

In certain preferred embodiments, x=y=19 and in (N')y the nucleotide in at least one position comprises a mirror nucleotide, a deoxyribonucleotide and a nucleotide joined to an adjacent nucleotide by a 2'-5' internucleotide bond.

In certain embodiments, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA in position 18. In some embodiments (N')y comprises 2'5' ribonucleotides in positions 15, 16, 17, 18, and 19 (5'>3'). In various embodiments (N)x further comprises a TNA, L-DNA or 2'5' ribonucleotide at one or more of positions 5, 6, 7, 8, or 9 (5'>3'). In other embodiments wherein x=y=20 the modifications for (N')y discussed above instead of being on positions 14, 15, 16, 17 are on positions 17, 18, 19, 20. For example, the modifications at one or both of positions 16 and 17 are on one or both of positions 18 or 19 for the 20-mer. All modifications in the 18-mer are similarly adjusted for the 20- and 22-mer.

In certain embodiments (N')y comprises an L-DNA in position 2 and 2'-5' internucleotide bonds in positions 15-19.

In some embodiments, neither strand of the modified dsRNA molecules disclosed herein is phosphorylated at the 3' and 5' termini. In other embodiments the sense and antisense strands are phosphorylated at the 3' termini. In yet another embodiment, the antisense strand is phosphorylated at the terminal 5' termini position using cleavable or non-cleavable phosphate groups. In yet another embodiment, either or both antisense and sense strands are phosphorylated at the 3' termini position using cleavable or non-cleavable phosphate groups.

Structure A1 is useful with any oligonucleotide pair (sense and antisense strands) to a mammalian or non-mammalian, i.e. microbial or viral gene. In some embodiments the mammalian gene is a human gene. Examples of oligonucleotide sequence pairs are provided in PCT Patent Publication Nos. WO 2006/023544, WO 2007/084684, WO 2008/050329, WO 2007/141796, WO 2009/044392, WO 2008/106102, WO 2008/152636, WO 2009/001359, WO/2009/090639 assigned to the assignee of the present invention and incorporated herein by reference in their entirety.

Unless otherwise indicated, in preferred embodiments of the structures discussed herein the covalent bond between each consecutive N and N' is a phosphodiester bond. Unless otherwise indicated, in preferred embodiments of the structures discussed herein the covalent bond between $N^1$ and (N)x and between $N^2$ and (N')y is a phosphodiester bond. In some embodiments at least one of the covalent bond is a phosphorothioate bond.

For all of the structures above, in some embodiments the oligonucleotide sequence of (N)x is fully complementary to the oligonucleotide sequence of (N')y. In other embodiments the antisense and sense strands are substantially complementary. In certain embodiments (N)x is fully complementary to a mammalian mRNA or microbial RNA or viral RNA. In other embodiments (N)x is substantially complementary to a mammalian mRNA or microbial RNA or viral RNA.

In some embodiments a modified siRNA compound having structure (A) exhibits beneficial properties including at least enhanced activity when compared to an siRNA compound wherein $N^1$ is complementary to a nucleotide in a target mRNA.

The present invention further provides a pharmaceutical composition comprising a compound disclosed herein, in an amount effective to inhibit mammalian or non-mammalian gene expression, and a pharmaceutically acceptable carrier, and use thereof for treatment of any one of the diseases and disorders disclosed herein. In some embodiments the mammalian gene is a human gene. In some embodiments the non-mammalian gene is involved in a mammalian disease, preferably human disease.

The present invention further relates to methods for treating or preventing the incidence or severity of any one of the diseases or conditions disclosed herein or for reducing the risk or severity of a disease or a condition disclosed herein in a subject in need thereof, wherein the disease or condition and/or a symptom or risk associated therewith is associated with expression of a mammalian or a non-mammalian gene the method comprising administering to a subject in need thereof a therapeutically effective amount of a compound disclosed herein. In a preferred embodiment the subject is a human subject. Provided herein are double stranded nucleic acid molecules for therapy.

siRNA Synthesis

Using public and proprietary algorithms the sense and antisense sequences of potential double stranded RNA molecules are generated.

The dsRNA molecules according to the above specifications are prepared essentially as described herein. The modified dsRNA compounds are synthesized by any of the methods that are well known in the art for synthesis of ribonucleic (or deoxyribonucleic) oligonucleotides. Synthesis is commonly performed in a commercially available synthesizer (available, inter alia, from Applied Biosystems). Oligonucleotide synthesis is described for example in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Ann Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, e.g. the procedures described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

In some embodiments the oligonucleotides of the present invention are synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the modified siRNA compounds of the present invention, two or more such sequences can be synthesized and linked together for use in the present invention.

In various embodiments some of the dsRNA molecules possess a terminal moiety covalently bound at the 5'-terminus of the antisense strand which is mismatched to a nucleotide in a target mRNA. In some embodiments of structure A2, $N^1$ (5' terminal nucleotide) in the antisense strand and/or $N^2$ (3' terminal nucleotide) of sense strand are substituted to generate the modified double stranded RNA compounds. In various embodiments the moiety at the 5'-terminus of the antisense strand is selected from the group consisting of ribouridine, deoxyribouridine, modified ribouridine, modified deoxyribouridine, pseudouracil, deoxypseudouracil, deoxyribothymidine, modified deoxyribothymidine, ribocytosine, modified ribocytosine, deoxyribocytosine, modified deoxyribocytosine, 5-methylribocytosine, modified 5-methylribocytosine, 5-methylribouridine, ribo-2-thiouridine, ribo-4-thiouridine, abasic ribose moiety and abasic deoxyribose moiety and the moiety at the 3'-terminus of the sense strand is selected from a ribonucleotide or a modified ribonucleotide or an unconventional moiety. The structures disclosed are beneficially applied to double stranded RNA useful in inhibiting or attenuating mammalian and non-mammalian gene expression.

Synthesis of TNAs

The following abbreviations and terms have the indicated meanings throughout:

Ac=acetyl
Bz=benzoyl
Chlorophos=chloro(2-cyanoethoxy)-(diisopropylamino) phosphine DCM=dichloromethyl
DMT=4,4'-dimethoxytrityl, viz.

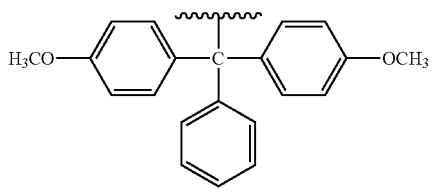 [SMILES: *C(c1ccccc1)(c1ccc(OC)cc1)c1ccc(OC)cc1]

DMT-Cl=chlorodimethoxytrityl=1-(chloro(4-methoxyphenyl)(phenyl)methyl)-4-methoxybenzene, viz.

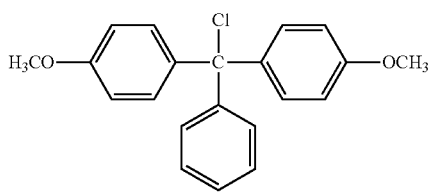 [SMILES: COc1ccc(C(Cl)(c2ccccc2)c2ccc(OC)cc2)cc1]

DIBAL-H=diisobutylaluminum hydride
DIPEA=N,N-diisopropylethyl amine
Tf=triflate=trifluoromethanesulfonate Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups".

The general synthetic schemes used are shown below.

SCHEME 1

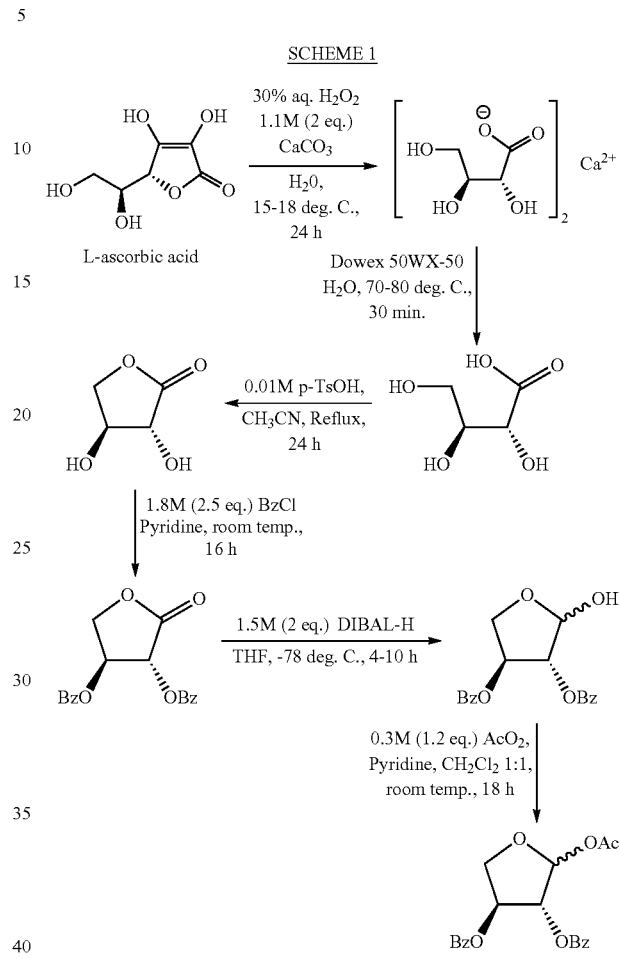

SCHEME 2

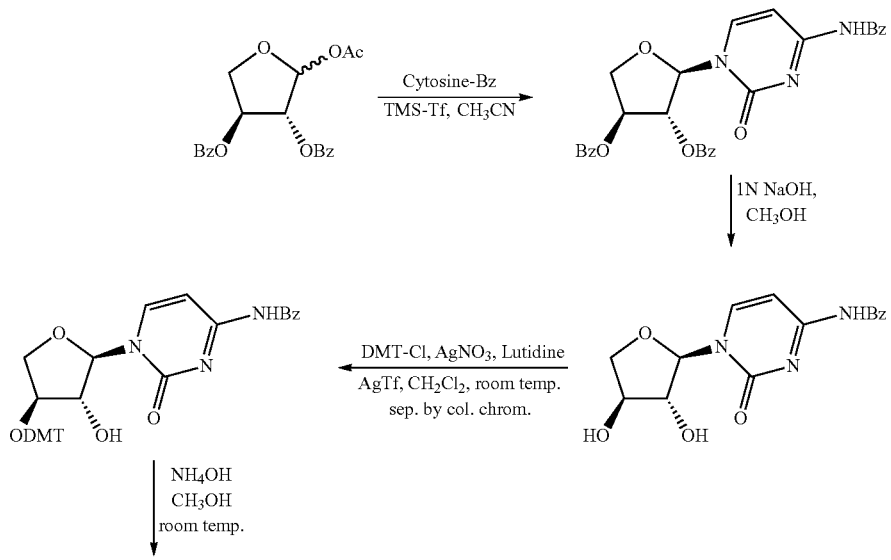

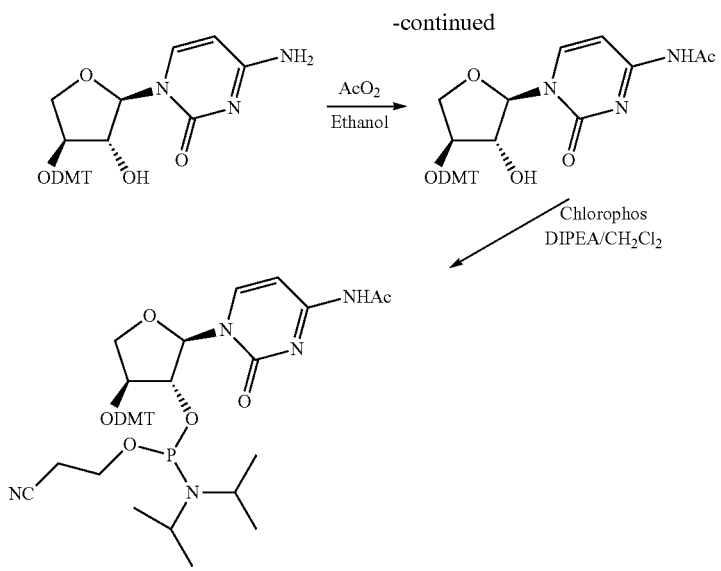

SCHEME 3

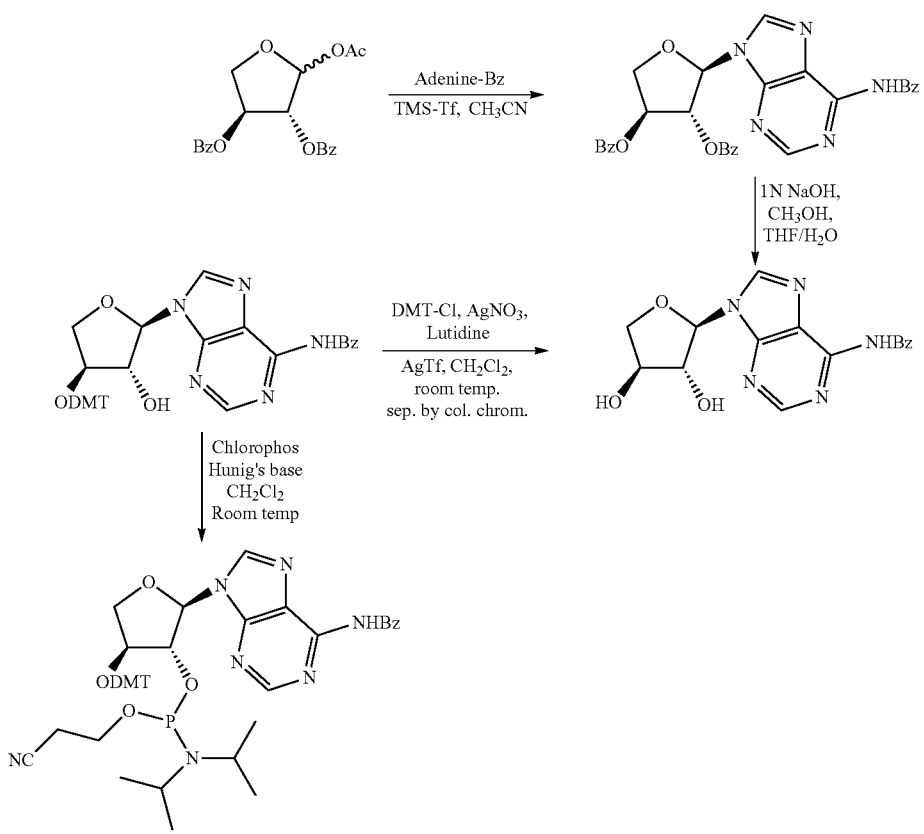

In one embodiment, provide are double-stranded nucleic acid (e.g. dsRNA, siRNA, siNA), which down-regulate the expression of mammalian or non-mammalian target genes. The double stranded molecules comprise at least one TNA on the sense strand and or the antisense strand. In some embodiments the sense strand comprises a nucleotide sequence derived from the target RNA sequence, and the antisense strand is complementary to the sense strand. In general, some deviation from the target mRNA sequence is tolerated without compromising the siRNA activity (see e.g. Czauderna et al., 2003, NAR 31(11), 2705-2716). A dsRNA of the invention inhibits gene expression on a post-transcriptional level with or without destroying the mRNA. Without being bound by theory, dsRNA may target the mRNA for specific cleavage and degradation and/or may inhibit translation from the targeted message.

In one aspect, provided are nucleic acid molecules (e.g., siNA molecules) in which a) the nucleic acid molecule includes a sense strand and an antisense strand; b) each strand of the is independently 15 to 49 nucleotides in length; (c) a 15 to 49 nucleotide sequence of the antisense strand is complementary to a sequence of a target RNA; d) at least one of the sense strand or antisense strand includes a TNA moiety; and e) 15 to 49 nucleotide sequence of the sense strand is complementary to the a sequence of the antisense strand and includes a 15 to 49 nucleotide sequence of a target RNA.

In some embodiments the antisense strand and the antisense strand are the same length. In some embodiments the antisense strand and the sense strand are 18-25 or 18-23 or 18-21 or 19-21 or 19 nucleotides in length.

In some embodiments the antisense strand includes a threose nucleic acid moiety in at least one of positions 5, 6, 7, 8, or 9 from the 5' terminus; and or the sense strand includes a threose nucleic acid moiety in at least one of positions 9 or 10 from the 5' terminus; and or the sense strand includes from 1 to 10 threose nucleic acid moieties at the 3' terminal or penultimate positions.

In some embodiments the antisense strand includes a threose nucleic acid moiety, in at least one of positions 5, 6, 7, 8, or 9 from the 5' terminus; and the sense strand includes a threose nucleic acid moiety, a 2'5' nucleotide or a pseudoU-ridine in at least one of positions 9 or 10 from the 5' terminus; and the sense strand includes from 1 to 10 threose nucleic acid moieties at the 3' terminal or penultimate positions.

In some embodiments the antisense strand includes a threose nucleic acid moiety, in at least one of positions 5, 6, 7, 8, or 9 from the 5' terminus; and the sense strand includes a threose nucleic acid moiety, a 2'5' nucleotide or a pseudoU-ridine in at least one of positions 9 or 10 from the 5' terminus; and the sense strand includes from 4 to 6 2'5' nucleotides at the 3' terminal or penultimate positions.

In some embodiments the antisense strand includes a threose nucleic acid moiety, a 2'5' nucleotide or a mirror nucleotide in at least one of positions 5, 6, 7, 8, or 9 from the 5' terminus; and the sense strand includes a threose nucleic acid moiety in at least one of positions 9 or 10 from the 5' terminus; and or the sense strand includes from 1 to 10 threose nucleic acid moieties or 4-6 2'5' nucleotides at the 3' terminal or penultimate positions.

Pharmaceutical Compositions

While it is possible for the compounds of the present invention to be administered as the raw chemical, it is preferable to present them as a pharmaceutical composition. Accordingly the present invention provides a pharmaceutical composition comprising one or more of the modified dsRNA molecules disclosed herein; and a pharmaceutically acceptable carrier. In some embodiments the pharmaceutical composition comprises two or more modified dsRNA molecules disclosed herein.

Further provided are pharmaceutical compositions comprising at least one nucleic acid molecule covalently or non-covalently bound to one or more molecule disclosed herein in an amount effective to inhibit a target gene expression; and a pharmaceutically acceptable carrier. The compound may be processed intracellularly by endogenous cellular complexes to produce one or more nucleic acid molecules disclosed herein.

Further provided are pharmaceutical compositions comprising a pharmaceutically acceptable carrier and one or more of the compounds disclosed herein in an amount effective to inhibit expression in a cell of a mammalian target gene, the compound comprising a sequence which is substantially complementary to the sequence of $(N)_x$.

In some embodiments, the modified dsRNA molecules disclosed herein are the main active component in a pharmaceutical composition. In other embodiments the modified dsRNA molecules disclosed herein are one of the active components of a pharmaceutical composition containing two or more therapeutic agents, said pharmaceutical composition further being comprised of one or more dsRNA molecules which target one or more target genes.

Further provided is a process of preparing a pharmaceutical composition, which comprises: providing one or more double stranded modified dsRNA molecules disclosed herein; and admixing said compound with a pharmaceutically acceptable carrier.

In a preferred embodiment, the modified dsRNA molecules disclosed herein used in the preparation of a pharmaceutical composition is admixed with a carrier in a pharmaceutically effective dose. In some embodiments the modified dsRNA molecules disclosed herein may be conjugated to a steroid or to a lipid or to another suitable molecule e.g. to cholesterol.

Also provided are kits, containers and formulations that include a nucleic acid molecule as provided herein for reducing expression of a target gene for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. In one embodiment, the container holds a nucleic acid molecule as disclosed herein. Kits may further include associated indications and/or directions; reagents and other compositions or tools used for such purpose can also be included.

The container can alternatively hold a composition comprising an active agent that is effective for treating, diagnosis, prognosing or prophylaxing a condition and can have a sterile access port (for example the container can be an intravenous solution bag or a vial having a stopper pierceable by a hypodermic injection needle). The active agents in the composition can be a single stranded or double stranded nucleic acid molecule as disclosed herein.

A kit may further include a second container that includes a pharmaceutically-acceptable buffer and may further include other materials desirable from a commercial and user standpoint, including other buffers, diluents, filters, stirrers, needles, syringes, and/or package inserts with indications and/or instructions for use.

The container holding the nucleic acid molecule may include a package that is labeled, and the label may bear a notice in the form prescribed by a governmental agency, for example the Food and Drug Administration, which notice is reflective of approval by the agency under Federal law, of the manufacture, use, or sale of the polynucleotide material therein for human administration.

A dsRNA molecule can be assembled from two separate polynucleotide strands, where one strand is the sense strand and the other is the antisense strand in which the antisense and sense strands are self-complementary (i.e. each strand includes nucleotide sequence that is complementary to nucleotide sequence in the other strand); such as where the antisense strand and sense strand form a duplex or double stranded structure having any length and structure as described herein for nucleic acid molecules as provided, for example wherein the double stranded region (duplex region)

is about 17 to about 40 (e.g., about 17, 18, 19, 20, 21, 22, 23, 24, 25, 26, 27, 28, 29, 30, 31, 32, 33, 34, 35, 36, 37, 38, 39, or 40 base pairs); the antisense strand includes nucleotide sequence that is complementary to nucleotide sequence in a target nucleic acid molecule or a portion thereof and the sense strand includes nucleotide sequence corresponding to the target nucleic acid sequence or a portion thereof (e.g., about 17 to about 40 or more nucleotides of the nucleic acid molecules herein are complementary to the target nucleic acid or a portion thereof).

In certain aspects and embodiments a double stranded nucleic acid molecule (e.g., a siNA molecule) provided herein may be a "RISC length" molecule or may be a Dicer substrate as described in more detail below.

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., NAR. 2004, 32(3):936-48; De Paula et al., RNA 2007, 13:431-56).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107,094, describe chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in *Drosophila* embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl modifications. Holen et al (NAR. 2003, 31(9): 2401-07) report that an siRNA having small numbers of 2'-O-methyl modified nucleosides gave good activity compared to wild type but that the activity decreased as the numbers of 2'-O-methyl modified nucleosides was increased. Chiu and Rana (RNA. 2003, 9:1034-48) describe that incorporation of 2'-O-methyl modified nucleosides in the sense or antisense strand (fully modified strands) severely reduced siRNA activity relative to unmodified siRNA. The placement of a 2'-O-methyl group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the disclosed herein offer an advantage in that they are stable and active and are useful in the preparation of pharmaceutical compositions for treatment of various diseases.

PCT Patent Publication Nos. WO 2008/104978, WO 2009/044392, WO 2011/066475 and WO 2011/084193 to the assignee of the present invention and hereby incorporated by reference in their entirety, disclose dsRNA structures.

PCT Publication No. WO 2008/050329 and U.S. Ser. No. 11/978,089 to the assignee of the present invention relate to inhibitors of pro-apoptotic genes, and are incorporated by reference in their entirety.

PCT Patent Publication Nos. WO 2004/111191 and WO 2005/001043 relate to methods for enhancing RNAi.

Provided herein is a method of down-regulating the expression of target gene by at least 20%, 30%, 40% or 50% as compared to a control, comprising contacting an mRNA transcript of the target gene with one or more of the compounds of the invention.

Additionally provided herein is a method of down-regulating the expression of target gene in a mammal by at least 20%, 30%, 40% or 50% as compared to a control, comprising administering one or more of the dsRNA molecules disclosed herein to the mammal. In a preferred embodiment the mammal is a human.

In various embodiments a double stranded nucleic acid molecule of Structure (A) is down-regulating the expression of a target gene, whereby the down-regulation of the expression of a target gene is selected from the group comprising down-regulation of gene function (which is examined, e.g. by an enzymatic assay or a binding assay with a known interactor of the native gene/polypeptide, inter alia), down-regulation of polypeptide product of the gene (which is examined, e.g. by Western blotting, ELISA or immunoprecipitation, inter alia) and down-regulation of mRNA expression of the gene (which is examined, e.g. by Northern blotting, quantitative RT-PCR, in-situ hybridization or microarray hybridization, inter cilia).

Dosages

The useful dosage to be administered and the particular mode of administration will vary depending upon such factors as the cell type, or for in vivo use, the age, weight and the particular subject and region thereof to be treated, the particular nucleic acid and delivery method used, the therapeutic or diagnostic use contemplated, and the form of the formulation, for example, naked, suspension, emulsion, micelle or liposome, as will be readily apparent to those skilled in the art. Typically, dosage is administered at lower levels and increased until the desired effect is achieved.

When lipids are used to deliver the nucleic acid, the amount of lipid compound that is administered can vary and generally depends upon the amount of nucleic acid being administered. For example, the weight ratio of lipid compound to nucleic acid is preferably from about 1:1 to about 30:1, with a weight ratio of about 5:1 to about 10:1 being more preferred.

A "therapeutically effective dose" for purposes herein is determined by considerations as are known in the art. The dose must be effective to achieve improvement including but not limited to improved survival rate or more rapid recovery, or improvement or alleviation of elimination of symptoms and other indicators as are selected as appropriate measures by those skilled in the art. The dsRNA disclosed herein can be administered in a single dose or in multiple doses.

A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

An appropriate dosage for a mammal may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 0.1 mg to about 500 mg of an active ingredient. Dosage units may be adjusted for local delivery, for example for intravitreal delivery of for transtympanic delivery.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the nucleic acid molecule disclosed herein may be administered once daily, qid, tid, bid, QD, or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of nucleic acids together contains a sufficient dose.

Delivery

The modified dsRNA compounds disclosed herein are administered as the compound per se (i.e. as naked siRNA) or as pharmaceutically acceptable salt and are administered alone or as an active ingredient in combination with one or more pharmaceutically acceptable carrier, solvent, diluent, excipient, adjuvant and vehicle. In some embodiments, the dsRNA molecules are delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

Pharmaceutically acceptable carriers, solvents, diluents, excipients, adjuvants and vehicles as well as implant carriers generally refer to inert, non-toxic solid or liquid fillers, diluents or encapsulating material not reacting with the active modified dsRNA compounds disclosed herein and they include liposomes and microspheres. For example, the dsRNA compounds disclosed herein may be formulated with polyethylenimine (PEI), with PEI derivatives, e.g. oleic and stearic acid modified derivatives of branched PET, with chitosan or with poly(lactic-co-glycolic acid) (PLGA). Formulating the compositions in e.g. liposomes, micro- or nano-spheres and nanoparticles, may enhance stability and benefit absorption.

Additionally, the compositions may include an artificial oxygen carrier, such as perfluorocarbons (PFCs) e.g. perfluorooctyl bromide (perflubron).

Examples of delivery systems useful in conjunction with the dsRNA molecules disclosed herein include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many such implants, delivery systems, and modules are well known to those skilled in the art. In one specific embodiment topical and transdermal formulations are selected.

Accordingly, in some embodiments the dsRNA molecules disclosed herein are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed (see, for example, Shen et al FEBS Let. 539: 111-114 (2003), Xia et al., Nat. Biotech. 20: 1006-1010 (2002), Reich et al., Mol. Vision 9: 210-216 (2003), Sorensen et al., J. Mol. Biol. 327: 761-766 (2003), Lewis et al., Nat. Gen. 32: 107-108 (2002) and Simeoni et al., NAR 31, 11: 2717-2724 (2003)). siRNA has recently been successfully used for inhibition of gene expression in primates; (for details see for example, Tolentino et al., Retina 2004. 24(1):132-138).

Additional formulations for improved delivery of the compounds disclosed herein can include non-formulated compounds, compounds covalently bound to cholesterol, and compounds bound to targeting antibodies (Song et al., Antibody mediated in vivo delivery of small interfering RNAs via cell-surface receptors, Nat Biotechnol. 2005. 23(6):709-17). Cholesterol-conjugated siRNAs (and other steroid and lipid conjugated siRNAs) can been used for delivery (see for example Soutschek et al Nature. 2004. 432:173-177; and Lorenz et al. Bioorg. Med. Chem. Lett. 2004. 14:4975-4977).

The naked siRNA or the pharmaceutical compositions comprising the chemically modified dsRNA disclosed herein are administered and dosed in accordance with good medical practice, taking into account the clinical condition of the individual patient, the disease to be treated, the site and method of administration, scheduling of administration, patient age, sex, body weight and other factors known to medical practitioners.

The modified dsRNA compounds disclosed herein can be administered by any of the conventional routes of administration. The modified dsRNA compounds are administered orally, subcutaneously or parenterally including intravenous, intraarterial, intramuscular, intraperitoneally, intraocular, ocular, otic, transtympanic and intranasal administration, intratracheal instillation and intratracheal inhalation, as well as infusion techniques. Implants of the compounds are also useful.

Liquid forms are prepared for invasive administration, e.g. injection or for topical or local or non-invasive administration. The term injection includes subcutaneous, transdermal, intravenous, intramuscular, intrathecal, intraocular, transtympanic and other parental routes of administration.

The liquid compositions include aqueous solutions, with and without organic co-solvents, aqueous or oil suspensions, emulsions with edible oils, as well as similar pharmaceutical vehicles. In a particular embodiment, the administration comprises intravenous administration.

In some embodiments the compounds disclosed herein are formulated for non-invasive administration. In some embodiments the compounds disclosed herein are formulated as eardrops for topical administration to the ear. In some embodiments the dsRNA molecules disclosed herein are formulated as eye drops for topical administration to the surface of the eye. Further information on administration of the dsRNA molecules disclosed herein can be found in Tolentino et al., Retina 2004. 24:132-138; and Reich et al., Molecular Vision, 2003. 9:210-216. In addition, in certain embodiments the compositions for use in the treatments of the present invention are formed as aerosols, for example for intranasal administration. In certain embodiments the compositions for use in the treatments of the present invention are formed as nasal drops, for example for intranasal instillation. In some embodiments the compositions are formulated as ear drops.

The therapeutic compositions disclosed herein are preferably administered into the lung by inhalation of an aerosol containing these compositions/compounds, or by intranasal or intratracheal instillation of said compositions. For further information on pulmonary delivery of pharmaceutical compositions see Weiss et al., Human Gene Therapy 1999. 10:2287-2293; Densmore et al., Molecular therapy 1999. 1:180-188; Gautam et al., Molecular Therapy 2001. 3:551-556; and Shahiwala & Misra, AAPS PharmSciTech 2004. 24; 6(3):E482-6. Additionally, respiratory formulations for siRNA are described in U.S. Patent Application Publication No. 2004/0063654. Respiratory formulations for siRNA are described in US Patent Application Publication No. 2004/0063654.

In certain embodiments, oral compositions (such as tablets, suspensions, solutions) may be effective for local delivery to the oral cavity such as oral composition suitable for mouthwash for the treatment of oral mucositis.

In a particular embodiment, the modified dsRNA compounds disclosed herein are formulated for intravenous administration for delivery to the kidney for the treatment of kidney disorders, e.g. acute renal failure (ARF), delayed graft function (DGF) and diabetic retinopathy. It is noted that the delivery of the modified dsRNA molecules to the target cells in the kidney proximal tubules is particularly effective in the treatment of ARF and DGF.

Delivery of compounds into the brain is accomplished by several methods such as, inter alia, neurosurgical implants, blood-brain barrier disruption, lipid mediated transport, carrier mediated influx or efflux, plasma protein-mediated transport, receptor-mediated transcytosis, absorptive-mediated transcytosis, neuropeptide transport at the blood-brain barrier, and genetically engineering "Trojan horses" for drug targeting. The above methods are performed, for example, as described in "*Brain Drug Targeting: the future of brain drug development*", W. M. Pardridge, Cambridge University Press, Cambridge, UK (2001).

In addition, in certain embodiments the compositions for use in the treatments disclosed herein are formed as aerosols, for example for intranasal administration.

Intranasal delivery for the treatment of CNS diseases has been attained with acetylcholinesterase inhibitors such as galantamine and various salts and derivatives of galantamine, for example as described in US Patent Application Publication No. 2006003989 and PCT Applications Publication Nos. WO 2004/002402 and WO 2005/102275. Intranasal delivery of nucleic acids for the treatment of CNS diseases, for example by intranasal instillation of nasal drops, has been described, for example, in PCT Application Publication No. WO 2007/107789.

Methods of Treatment

In one aspect provided herein is a method of treating a subject suffering from a disorder associated with target gene expression comprising administering to the subject a therapeutically effective amount of a modified dsRNA compound disclosed herein. In preferred embodiments the subject being treated is a warm-blooded animal and, in particular, mammal including human.

"Treating a subject" refers to administering to the subject a therapeutic substance effective to ameliorate symptoms associated with a disease, to lessen the severity or cure the disease, to slow down the progress of the disease, to prevent the disease from occurring or to postpone the onset of the disease. "Treatment" refers to both therapeutic treatment and prophylactic or preventative measures, wherein the object is to prevent a disorder, to delay the onset of the disorder or reduce the symptoms of a disorder. Those in need of treatment include those already experiencing the disease or condition, those prone to having the disease or condition, and those in which the disease or condition is to be prevented. The compounds disclosed herein are administered before, during or subsequent to the onset of the disease or condition.

A "therapeutically effective dose" refers to an amount of a pharmaceutical compound or composition which is effective to achieve an improvement in a subject or his physiological systems including, but not limited to, improved survival rate, more rapid recovery, improvement or elimination of symptoms, delayed onset of a disorder, slower progress of disease and other indicators as are selected as appropriate determining measures by those skilled in the art.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently. In various embodiments provided are methods and compositions useful in preventing or treating primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, in a subject in need thereof.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysprotcinemia, temporal arteritis, ischemic optic neuropathy (ION), anterior ischemic optic neuropathy (AION), optic neuritis (primary or secondary to autoimmune diseases), glaucoma, von Hippel Lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus crythematosus, arteriolitis with SS-A autoantibody, acute multifocal hemorrhagic vasculitis, vasculitis resulting from infection, vasculitis resulting from Behçet's disease, sarcoidosis, coagulopathies, neuropathies, nephropathies, microvascular diseases of the kidney, and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubcosis iritis; proliferative vitrco-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury. In various embodiments all these neovascular conditions are treated using the compounds and pharmaceutical compositions disclosed herein.

"Eye disease" refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases and retinal vein occlusion (RVO). In various embodiments, conditions disclosed herein, such as DR, which are regarded as either a microvascular disorder or an eye disease, or both, under the definitions presented herein, are treated according to the methods disclosed herein.

Fibrotic disorder includes fibrosis of the liver, lung, heart, kidney, bone marrow, eye, and uterine; systemic fibrosis and fibrosis resulting from injury or surgery. Fibrotic disorder includes liver fibrosis, hepatic damage, and liver cirrhosis; pulmonary fibrosis including lung fibrosis (including IPF idiopathic pulmonary fibrosis), any condition causing kidney fibrosis (e.g., CKD including ESRD), peritoneal fibrosis, fibrillogenesis, fibrotic diseases in other organs, abnormal scarring (keloids) associated with all possible types of skin injury accidental and jatrogenic (operations); scleroderma; cardiofibrosis, failure of glaucoma filtering operation; and intestinal adhesions.

More specifically, provided herein are methods and compositions useful in treating a subject suffering from or susceptible to adult respiratory distress syndrome (ARDS); Chronic obstructive pulmonary disease (COPD); acute lung injury (ALI); Emphysema; Diabetic Neuropathy, nephropathy and retinopathy; diabetic macular edema (DME) and other diabetic conditions; Glaucoma; age related macular degeneration (AMD); bone marrow transplantation (BMT) retinopathy; ischemic conditions; ocular ischemic syndrome (OIS); kidney disorders: acute renal failure (ARF), delayed graft function (DGF), transplant rejection; hearing disorders (including hearing loss); spinal cord injuries; oral mucositis; dry eye syndrome and pressure sores; neurological disorders arising from ischemic or hypoxic conditions, such as hypertension, hypertensive cerebral vascular disease, a constriction or obstruction of a blood vessel—as occurs in the case of a thrombus or embolus, angioma, blood dyscrasias, any form of compromised cardiac function including cardiac arrest or failure, systemic hypotension; stroke, disease, disorders and injury of the CNS, including, without being limited to, epilepsy, spinal cord injury, brain injury and neurodegenerative disorders, including, without being limited to Parkinson's disease, Amyotrophic Lateral Sclerosis (ALS, Lou Gehrig's Disease), Alzheimer's disease, Huntington's disease and any other disease-induced dementia (such as HIV-associated dementia for example); neurological disorders arising from exposure to toxic agents.

Provided herein are compounds, compositions and methods useful in the treatment of cancer. The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. Other examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

Additionally, provided is a method of down-regulating the expression of a target gene by at least 20%, 30%, 40% or 50% as compared to a control comprising contacting target mRNA with one or more of the modified dsRNA molecules disclosed herein. In various embodiments the modified dsRNA molecules down-regulates target gene whereby the down-regulation is selected from the group comprising down-regulation of gene function, down-regulation of polypeptide and down-regulation of mRNA expression.

Provide herein is a method of inhibiting the expression of the target gene by at least 20%, 30%, or 40%, preferably by 50%, 60% or 70%, more preferably by 75%, 80% or 90% as compared to a control comprising contacting an mRNA transcript of the target gene with one or more of the dsRNA compounds disclosed herein.

In one embodiment the modified dsRNA molecules disclosed herein inhibit the target gene polypeptide, whereby the inhibition is selected from the group comprising inhibition of function (which is examined by, for example, an enzymatic assay or a binding assay with a known interactor of the native gene/polypeptide, inter alia), inhibition of target protein (which is examined by, for example, Western blotting, ELISA or immuno-precipitation, inter alia) and inhibition of target mRNA expression (which is examined by, for example, Northern blotting, quantitative RT-PCR, in-situ hybridization or microarray hybridization, inter alia).

In additional embodiments provided is a method of treating a subject suffering from or susceptible to any disease or disorder accompanied by an elevated level of a mammalian or non-mammalian target gene, the method comprising administering to the subject a modified dsRNA molecule disclosed herein in a therapeutically effective dose thereby treating the subject.

Provided herein are double stranded nucleic acid molecules for use in therapy, in particular for use where down-regulation of expression of a mammalian or non-mammalian target gene is beneficial.

By "exposure to a toxic agent" is meant that the toxic agent is made available to, or comes into contact with, a mammal. A toxic agent can be toxic to the nervous system. Exposure to a toxic agent can occur by direct administration, e.g., by ingestion or administration of a food, medicinal, or therapeutic agent, e.g., a chemotherapeutic agent, by accidental contamination, or by environmental exposure, e g., aerial or aqueous exposure.

In other embodiments the chemically modified dsRNA compounds and methods disclosed herein are useful for treating or preventing the incidence or severity of other diseases and conditions in a subject. These diseases and conditions include, but are not limited to stroke and stroke-like situations (e.g. cerebral, renal, cardiac failure), neuronal cell death, brain injuries with or without reperfusion, spinal cord injury, chronic degenerative diseases e.g. neurodegenerative disease including, Alzheimer's disease, Parkinson's disease, Huntington's disease, multiple sclerosis, spinobulbar atrophy, prion disease and apoptosis resulting from traumatic brain injury (TBI). In an additional embodiment, the compounds and methods disclosed herein are directed to providing neuroprotection, and or cerebroprotection.

Without limitation a target gene is selected from the group consisting of p53 (TP53), TP53BP2, LRDD, CYBA, ATF3, CASP2 (Caspase 2), NOX3, HRK; C1QBP, BNIP3, MAPK8; Rac1, GSK3B, CD38, STEAP4, BMP2a; GJA1, TYROBP, CTGF, SPP1, RTN4R, ANXA2, RHOA, DUOX1, SLC5A1, SLC2A2, AKR1B1, SORD, SLC2A1, MME, NRF2, SRM, REDD2 (RTP801L), REDD1 (RTP801), NOX4, MYC, PLK1, ESPL1, HTRA2, KEAP1, p66, ZNHITI, LGALS3, CYBB (NOX2), NOX1, NOXO1, ADRB1, HI 95, ARF1, ASPP1, SOX9, FAS, FASLG, Human MLL, AF9, CTSD, CAPNS1, CD80, CD86, HES1, HES5, HEY1, HEY2, CDKN1B (p27), ID1, ID2, ID3, CDKN2A, Caspase 1, Caspase 3, Caspase 4, Caspase 5, Caspase 6, Caspase 7, Caspase 8, Caspase 9, Caspase 10, Caspase 12, Caspase 14, Apaf-1, Nod1, Nod2, Ipaf, DEF-CAP, RAIDD, RICK, Bcl10, ASC, TUCAN, ARC, CLARP, FADD, DEDD, DEDD2, Cryopirin, PYC1, Pyrin, TRADD, UNC5a, UNC5b, UNC5c, ZUD, p84N5, LRDD, CDK1, CDK2, CDK4, CDK5, CDK9, PITSLRE A, CHK2, LATS1, Prk, MAP4K1, MAP4K2, STK4, SLK, GSK3alpha, GSK3beta, MEKK1, MAP3K5 (Ask1), MAP3K7, MAP3K8, MAP3K9, MAP3K10, MAP3K11, MAP3K12, DRP-1, MKK6, p38, JNK3, DAPK1, DRAK1, DRAK2, IRAK, RIP, RIP3, RIPS, PKR, IRE1, MSK1, PKCalpha, PKCbeta, PKCdelta, PKCepsilon, PKCeta, PKCmu, PKCtheta, PKCzeta, CAMK2A, HIPK2, LKB1, BTK, c-Src, FYN, Lck, ABL2, ZAP70, TrkA, TrkC, MYLK, FGFR2, EphA2, AATYK, c-Met, RET, PRKAA2, PLA2G2A, SMPD1, SMPD2, SPP1, FAN, PLCG2, IP6K2, PTEN, SHIP, AIF, AMID, Cytochrome c, Smac, HtrA2, TSAP6, DAP-1, FEM-, DAP-3, Granzyme B, DIO-1, DAXX, CAD, CIDE-A, CIDE-B, Fsp27, Ape1, ERCC2, ERCC3, BAP31, Bit1, AES, Huntingtin, HIP1, hSir2, PHAP1, GADD45b, GADD34, RAD21, MSH6, ADAR, MBD4, WW45, ATM, mTOR, TIP49, diubiquitin/FAT10, FAF1, p193, Scythe/BAT3, Amida, IGFBP-3, TDAG51, MCG10, PACT, p52/RAP, ALG2, ALG3, presenelin-1, PSAP, AIP1/Alix, ES18, mda-7, p14ARF, ANTI, p33ING1, p33ING2, p53AIP1, p53DINP1, MGC35083, NRAGE, GRIM19, lipocalin 2, glycodelin A, NADE, Porimin, STAG1, DAB2, Galectin-7, Galectin-9, SPRC, FLJ21908, WWOX, XK, DKK-1, Fzd1, Fzd2, SARP2, axin 1, RGS3, DVL1, NFkB2, IkBalpha, NF-ATC1, NF-ATC2, NF-ATC4, zf3/ZNF319, Egr1, Egr2, Egr3, Sp1, TIEG, WT1, Zac1, Icaros, ZNF148, ZKVZNF443, ZNF274, WIG1, HIVEP1, HIVEP3, Fliz1, ZPR9, GATA3, TR3, PPARG, CSMF, RXRa, RARa, RARb, RARg, T3Ra, Erbeta, VDR, GR/GCCR, p53, p73alpha, p63(human [ta alpha, ta beta, ta gamma, da alpha, a beta, da gamma], 53BP2, ASPP1, E2F1, E2F2, E2F3, HIF1 alpha, TCF4, c-Myc, Max, Mad, MITF, Id2, Id3, Id4, c-Jun, c-Fos, ATF3, NF-IL6, CHOP, NRF1, c-Maf, Bach2, Msx2, Csx, Hoxa5, Ets-1, PU1/Spi1, Ets-2, ELK1, TEL1, c-Myb, TBX5, IRF1, IRF3, IRF4, IRF9, AP-2 lpha, FKHR, FOXO1A, FKHRL1, FOXO3a, AFX1, MLLT7, Tip60, BTG1, AUF1, HNRPD, TIA1, NDG1, PCBP4, MCG10, FXR2, TNFR2, LTbR, CD40, CD27, CD30, 4-1BB, TNFRSF19, XEDAR, Fn14, OPG, DcR3, FAS, TNFR1, WSL-1, p75NTR, DR4, DR5, DR6, EDAR, TNF lpha, FAS ligand, TRAIL, Lymphotoxin alpha, Lymphotoxin beta, 4-1BBL, RANKL, TL1, TWEAK, LIGHT, APRIL, IL-1-alpha, IL-1-beta, IL-18, FGF8, IL-2, IL-21, IL-5, IL-4, IL-6, LIF, IL-12, IL-7, IL-10, IL-19, IL-24, IFN alpha, IFN beta, IFN gamma, M-CSF, Prolactinm, TLR2, TLR3, TLR4, MyD88, TRIF, RIG-1, CD14, TCR alpha, CD3 gamma, CD8, CD4, CD7, CD19, CD28, CTLA4, SEMA3A, SEMA3B, HLA-A, HLA-B, HLA-L, HLA-Dmalpha, CD22, CD33, CALL, DCC, ICAM1, ICAM3, CD66a, PVR, CD47, CD2, Thy-1, SIRPa1, CD5, E-cadherin, ITGAM, ITGAV, CD18, ITGB3, CD9, IgE Fc R beta, CD82, CD81, PERP, CD24, CD69, KLRD1, galectin 1, B4GALT1, C1q alpha, C5R1, MIP1alpha, MIP1beta, RANTES, SDF1, XCL1, CCCKR5, OIAS/OAS1, INDO, MxA, IFI16, AIM2, iNOS, HB-EGF, HGF, MIF, TRAF3, TRAF4, TRAF6, PAR-4, IKKGamma, FIP2, TXBP151, FLASH, TRF1, IEX-1S, Dok1, BLNK, CIN85, Bif-1, HEFT, Vav1, RasGRP1, POSH, Rac1, RhoA, RhoB, RhoC, ALG4, SPP1, TRIP, SIVA, TRABID, TSC-22, BRCA1, BARD1, 53BP1, MDC1, Mdm4, Siah-1, Siah-2, RoRet, TRIM35, PML, RFWD1, DIPJ, Socs1, PARC, USP7, CYLD, TTR, SERPINH1 (HSP47). Other useful target genes are genes of microbial origin including viral, bacterial and *mycoplasma* genes.

Combination Therapy

The methods of treating the diseases disclosed herein include administering a modified double stranded nucleic acid molecule disclosed herein in conjunction or in combination with an additional inhibitor, a substance which improves the pharmacological properties of the modified siRNA compound, or an additional compound known to be effective in the treatment of a subject suffering from or susceptible to any of the hereinabove mentioned diseases and disorders.

In another embodiment, provided are pharmaceutical compositions comprising a combination of a therapeutic modified dsRNA compound disclosed herein together with at least one additional therapeutically active agent. By "in conjunction with" or "in combination with" is meant prior to, simultaneously or subsequent to. Accordingly, the individual components of such a combination are administered either sequentially or simultaneously from the same or separate pharmaceutical formulations.

Combination therapies comprising known treatments for treating microvascular disorders, eye disease and conditions (e.g. macular degeneration), hearing impairments (including hearing loss), respiratory disorders, kidney disorders, organ transplantation, neurodegenerative disorders (e.g. spinal cord injury), angiogenesis- and apoptosis-related conditions, in conjunction with the modified dsRNA compounds and therapies described herein are considered part of the current invention.

Accordingly, in another embodiment, an additional pharmaceutically effective compound is administered in conjunction with the pharmaceutical composition disclosed herein. In addition, the modified dsRNA compounds disclosed herein are used in the preparation of a medicament for use as adjunctive therapy with a second therapeutically active compound to treat such conditions. Appropriate doses of known second therapeutic agents for use in combination with a chemically modified dsRNA compound disclosed herein are readily appreciated by those skilled in the art.

In some embodiments the combinations referred to above are presented for use in the form of a single pharmaceutical formulation.

The administration of a pharmaceutical composition comprising any one of the pharmaceutically active dsRNA disclosed herein is carried out by any of the many known routes of administration, including intravenously, intra-arterially, subcutaneously, intraperitoneally or intra-cerebrally, as determined by a skilled practitioner. Using specialized formulations, it is possible to administer the compositions orally or via inhalation or via intranasal instillation. In some embodiments a compound of the present invention is formulated for topical administration, including as eardrops, eye drops, dermal formulation, transdermal formulation and the like.

By "in conjunction with" is meant that the additional pharmaceutically effective compound is administered prior to, at the same time as, or subsequent to administration of the compounds or the pharmaceutical compositions of the present invention. The individual components of such a combination referred to above, therefore, can be administered either sequentially or simultaneously from the same or separate pharmaceutical formulations. As is the case for the present modified siRNA compounds, a second therapeutic agent can be administered by any suitable route, for example, by oral, buccal, inhalation, sublingual, rectal, vaginal, transurethral, nasal, otic, ocular, topical, percutaneous (i.e., transdermal), or parenteral (including intravenous, intramuscular, subcutaneous, and intracoronary) administration.

In some embodiments, a modified dsRNA compound disclosed herein and the second therapeutic agent (dsRNA or other) are administered by the same route, either provided in a single composition as two or more different pharmaceutical compositions. However, in other embodiments, a different route of administration for the modified dsRNA compound disclosed herein and the second therapeutic agent is either possible or preferred. Persons skilled in the art are aware of the best modes of administration for each therapeutic agent, either alone or in combination.

In various embodiments, the modified dsRNA compounds disclosed herein are the main active component in a pharmaceutical composition.

In another aspects, provided are pharmaceutical compositions comprising two or more dsRNA molecules for the treatment of a disease and for any of the diseases and conditions mentioned herein. In some embodiments the two or more dsRNA molecules or formulations comprising said molecules are admixed in the pharmaceutical composition in amounts that generate equal or otherwise beneficial activity. In certain embodiments the two or more siRNA molecules are covalently or non-covalently bound, or joined together by a nucleic acid linker of a length ranging from 2-100, preferably 2-50 or 2-30 nucleotides.

In some embodiments the pharmaceutical compositions of the invention further comprise one or more additional dsRNA molecule, which targets one or more additional gene. In some embodiments, simultaneous inhibition of said additional gene(s) provides an additive or synergistic effect for treatment of the diseases disclosed herein.

The treatment regimen according to the invention is carried out, in terms of administration mode, timing of the administration, and dosage, so that the functional recovery of the patient from the adverse consequences of the conditions disclosed herein is improved or so as to postpone the onset of a disorder. The treatment regimen according to the invention is carried out, in terms of administration mode, timing of the administration, and dosage, so that the functional recovery of the patient from the adverse consequences of the conditions disclosed herein is improved or so as to postpone the onset of a disorder. The amount of active ingredient that can be combined with a carrier to produce a single dosage form varies depending upon the host treated and the particular mode of administration. Dosage unit forms generally contain between from about 0.1 mg to about 500 mg of an active ingredient. Dosage units may be adjusted for local delivery, for example for intravitreal delivery of for transtympanic delivery.

RNA Interference and siNA Molecules

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is often referred to as post-transcriptional gene silencing (PTGS) or RNA silencing. The process of post-transcriptional gene silencing is thought to be an evolutionarily-conserved cellular defense mechanism used to prevent the expression of foreign genes (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

The presence of long dsRNAs in cells stimulates the activity of a ribonuclease III enzyme referred to as "dicer" (Bass, 2000, Cell, 101, 235; Zamore et al., 2000, Cell, 101, 25-33; Hammond et al., 2000, Nature, 404, 293). Dicer is involved in the processing of the dsRNA into short dsRNA pieces known as siNA or siRNA (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and include about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in *C. elegans*. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Hammond et al., 2000, Nature, 404, 293, describe RNAi in *Drosophila* cells transfected with dsRNA. Elbashir et al., 2001, Nature, 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877 and Tuschl et al., International PCT Publication No. WO 01/75164) has revealed certain requirements for siRNA length, structure, chemical composition, and sequence that are essential to mediate efficient RNAi activity.

Nucleic acid molecules (for example having structural features as disclosed herein) may inhibit or down regulate gene expression or viral replication by mediating RNA interference "RNAi" or gene silencing in a sequence-specific manner; see e.g., Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

The invention has been described in an illustrative manner, and it is to be understood that the terminology used is intended to be in the nature of words of description rather than of limitation.

Modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Example 1. Generation of Sense Strand and Antisense Strand Sequences for dsRNAs to Target Genes and Production of the Modified dsRNA Compounds Using proprietary algorithms and the known sequence of a target gene, 18 and 19-mer sequences for potential dsR- NAs were generated. The antisense strand sequences that were generated using this method are fully or substantially complementary to a section of target mRNA sequence. In some embodiments the antisense sequence is fully complementary to a section of the corresponding mRNA sequence. For generating some of the modified dsRNA compounds disclosed herein, the nucleotide at the 5' terminal position of the antisense strand (N)x (position 1; N¹) was substituted to generate a double stranded nucleic acid molecule of embodiments of structure A2. In other examples, the nucleotide at the 5' terminal position of the antisense strand (N)x and the nucleotide at the 3' terminal position of the sense strand (N')y were substituted to generate the double stranded nucleic acid molecule of embodiments of Structure A2.

In general, the double stranded nucleic acid molecules having specific sequences that are selected for in vitro testing are specific for human and a second species such as rat, mouse non-human primate or rabbit genes.

The exemplary compounds target Rac1 (*Homo sapiens* ras-related C3 botulinum toxin substrate 1 (rho family, small GTP binding protein Rac1) (RAC1), transcript variant Rac1, mRNA) gi|156071503|ref|NM_006908.4|SEQ ID NO:1; or MYD88 variant 1 (*Homo sapiens* myeloid differentiation primary response gene (88) (MYD88), mRNA) gi|289546502|ref|NM_001172567.1|SEQ ID NO:2; or Rat tumor protein p53 gi|189083685|ref|NM_030989.3|SEQ ID NO:3 Polynucleotide sequences of target RNA sequences of mammalian and non-mammalian target genes are available, for example, on the NCBI web site [http://www.ncbi.nlm.nih.gov/].

Example 2. In Vitro Testing of Modified dsRNA Molecules

```
Sequence of Rac1_2 sense strand and antisense
strand (5' > 3'):
                                       (SEQ ID NO: 4)
GAGUCCUGCAUCAUUUGAA sense strand (SEQ ID NO: 5)
UUCAAAUGAUGCAGGACUC antisense strand Sequence of Myd88_11 sense strand and antisense
strand (5' > 3'):
                                       (SEQ ID NO: 6)
GAAUGUGACUUCCAGACCA sense strand (SEQ ID NO: 7)
UGGUCUGGAAGUCACAUUC antisense strand Sequence of p53_17 sense strand and antisense
strand (5' > 3'):
                                       (SEQ ID NO: 8)
GAAGAAAAUUUCCGCAAAA sense strand (SEQ ID NO: 9)
UUUUGCGGAAAUUUUCUUC antisense strand Sequence of STRUC_2 sense strand and antisense
strand (5' > 3'):
                                       (SEQ ID NO: 10)
AGGGCGUCAUCCAACACAA sense strand (SEQ ID NO: 11)
UUGUGUUGGAUGACGCCCU antisense strand
```

The double stranded compounds tested are shown herein in Tables A, B, C and D according to target gene. Sense strand and antisense strand description provide the positional information of modified nucleotides.

Synthesis of Chimeric Oligonucleotides Including 2'5' Ribonucleotides, RNA and TNA Moieties.

TNA phosphoramidites were synthesized using the method disclosed herein. The synthesis of dsRNA comprising RNA and TNA phosphoramidites was carried out using established solid phase synthesis methods, with some modifications to optimize the coupling yields (Schoning et al, 2002. Helvetica Chimica ACTA 85:4111-4153).

Tables A-D provide sense strands and antisense strands useful in generating dsRNA molecules. Table E provides the legend for the sense strands and antisense strands. In the tables below 2'5' refers to a ribonucleotide providing a 2'5' linkage to the adjacent nucleotide; TNA refers to a threose nucleic acid moiety providing a 3'2' linkage to an adjacent nucleotide; L-DNA refers to a mirror nucleotide.

TABLE A

Synthesized sense strand and antisense strand for generating dsRNA molecules targeting RAC1
(SEQ ID NOS 12-105, respectively, in order of columns):

| Name | Sense strand 5->3 code | AntiSense strand 5->3 code | Unconventional moieties sense (5' > 3') | Unconventional moieties antisense (5' > 3') |
|---|---|---|---|---|
| RAC1_2_S1392 | rG;rA;rG;rU;rC;rC;rU; rG;rC;rA;rU;rC;rA; rU;rU;rU;rG;rA;rA$ (SEQ ID NO: 12) | rU;mU;rC;rA;rA;rA;rU;rG; rA;rU;rG;rC;rA;rG;rG; rA;rC;rU;rC$ (SEQ ID NO: 59) | | |
| RAC1_2_S1393 | rG;rA;rG;rU;rC;rC;rU; rG;rC;rA;rU;rC;rA; rU;rU;rU;rG;rA;rA$ (SEQ ID NO: 13) | rU;rU;rC;rA;rA2p;rA;rU; rG;rA;rU;rG;rC;rA;rG;rG; rA;rC;rU;rC$ (SEQ ID NO: 60) | | 2'5' 5 |
| RAC1_2_S1394 | rG;rA;rG;rU;rC;rC;rU; rG;rC;rA;rU;rC;rA;rU; rU;rU;rG;rA;rA$ (SEQ ID NO: 14) | rU;rU;rC;rA;rA2p;rA2p; rU;rG;rA;rU;rG;rC;rA;rG; rG;rA;rC;rU;rC$ (SEQ ID NO: 61) | | 2'5' 5, 6 |
| RAC1_2_S1395 | rG;rA;rG;rU;rC;rC;rU; rG;rC;rA;rU;rC;rA;rU; rU;rU;rG;rA;rA$ (SEQ ID NO: 15) | rU;rU;rC;rA;rA;rA2p;rU;rG; rA;rU;rG;rC;rA;rG;rG;rA; rC;rU;rC$ (SEQ ID NO: 62) | | 2'5' 6 |
| RAC1_2_S1396 | rG;rA;rG;rU;rC;rC;rU; rG;rC;rA;rU;rC;rA;rU; rU;rU;rG;rA;rA$ (SEQ ID NO: 16) | rU;rU;rC;rA;rA;rA2p;rU2p; rG;rA;rU;rG;rC;rA;rG;rG; rA;rC;rU;rC$ (SEQ ID NO: 63) | | 2'5' 6, 7 |

TABLE A-continued

Synthesized sense strand and antisense strand for generating dsRNA molecules targeting RAC1
(SEQ ID NOS 12-105, respectively, in order of columns):

| Name | Sense strand 5->3 code | AntiSense strand 5->3 code | Unconventional moieties sense (5' > 3') | Unconventional moieties antisense (5' > 3') |
|---|---|---|---|---|
| RAC1_2_S1397 | rG;rA;rG;rU;rC;rC;rU;rG;rC;rA;rU;rC;rA;rU;rU;rU;rG;rA;rA$ (SEQ ID NO: 17) | rU;rU;rC;rA;rA;rA;rU2p;rG;rA;rU;rG;rC;rA;rG;rG;rA;rC;rU;rC$ (SEQ ID NO: 64) | | 2'5' 7 |
| RAC1_2_S1398 | rG;rA;rG;rU;rC;rC;rU;rG;rC;rA;rU;rC;rA;rU;rU;rU;rG;rA;rA$ (SEQ ID NO: 18) | rU;rU;rC;rA;rA;rA;rU2p;rG2p;rA;rU;rG;rC;rA;rG;rG;rA;rC;rU;rC$ (SEQ ID NO: 65) | | 2'5' 7, 8 |
| RAC1_2_S1399 | rG;rA;rG;rU;rC;rC;rU;rG;rC;rA;rU;rC;rA;rU;rU;rU;rG;rA;rA$ (SEQ ID NO: 19) | rU;rU;rC;rA;rA;rA;rU;rG2p;rA;rU;rG;rC;rA;rG;rG;rA;rC;rU;rC$ (SEQ ID NO: 66) | | 2'5' 8 |
| RAC1_2_S1400 | rG;rA;rG;rU;rC;rC;rU;rG;rC;rA;rU;rC;rA;rU;rU;rU;rG;rA;rA$ (SEQ ID NO: 20) | rU;rU;rC;rA;rA;LdA;rU;rG;rA;rU;rG;rC;rA;rG;rG;rA;rC;rU;rC$ (SEQ ID NO: 67) | | L-DNA 6 |
| RAC1_2_S1401 | rG;rA;rG;rU;rC;rC;rU;rG;rC;rA;rU;rC;rA;rU;rU;rU;rG;rA;rA$ (SEQ ID NO: 21) | rU;rU;rC;rA;rA;rA;LdT;rG;rA;rU;rG;rC;rA;rG;rG;rA;rC;rU;rC$ (SEQ ID NO: 68) | | L-DNA 7 |
| RAC1_2_S1402 | rG;rA;rG;rU;rC;rC;rU;rG;rC;rA;rU;rC;rA;rU;rU;rU;rG;rA;rA$ (SEQ ID NO: 22) | rU;rU;rC;rA;rA;rA;rU;LdG;rA;rU;rG;rC;rA;rG;rG;rA;rC;rU;rC$ (SEQ ID NO: 69) | | L-DNA 8 |
| RAC1_2_S1403 | rG;rA;rG;rU;rC;rC;rU;rG;rC;rA;rU;rC;rA;rU;rU;rU;rG;rA;rA$ (SEQ ID NO: 23) | rU;rU;rC;rA;rA;tnaA;rU;rG;rA;rU;rG;rC;rA;rG;rG;rA;rC;rU;rC$ (SEQ ID NO: 70) | | TNA 6 |
| RAC1_2_S1404 | rG;rA;rG;rU;rC;rC;rU;rG;rC;rA;rU;rC;rA;rU;rU;rU;rG;rA;rA$ (SEQ ID NO: 24) | mU;rU;mC;rA;rA2p;rA;mU;rG;mA;rU;mG;rC;mA;rG;mG;rA;mC;rU;mC$ (SEQ ID NO: 71) | | 2'5' 5 |
| RAC1_2_S1405 | rG;rA;rG;rU;rC;rC;rU;rG;rC;rA;rU;rC;rA;rU;rU;rU;rG;rA;rA$ (SEQ ID NO: 25) | mU;rU;mC;rA;rA2p;rA2p;mU;rG;mA;rU;mG;rC;mA;rG;mG;rA;mC;rU;mC$ (SEQ ID NO: 72) | | 2'5' 5-6 |
| RAC1_2_S1406 | rG;rA;rG;rU;rC;rC;rU;rG;rC;rA;rU;rC;rA;rU;rU;rU;rG;rA;rA$ (SEQ ID NO: 26) | mU;rU;mC;rA;rA;rA2p;mU;rG;mA;rU;mG;rC;mA;rG;mG;rA;mC;rU;mC$ (SEQ ID NO: 73) | | 2'5' 6 |
| RAC1_2_S1407 | rG;rA;rG;rU;rC;rC;rU;rG;rC;rA;rU;rC;rA;rU;rU;rU;rG;rA;rA$ (SEQ ID NO: 27) | mU;rU;mC;rA;rA;rA2p;rU2p;rG;mA;rU;mG;rC;mA;rG;mG;rA;mC;rU;mC$ (SEQ ID NO: 74) | | 2'5' 6-7 |
| RAC1_2_S1408 | rG;rA;rG;rU;rC;rC;rU;rG;rC;rA;rU;rC;rA;rU;rU;rU;rG;rA;rA$ (SEQ ID NO: 28) | mU;rU;mC;rA;mA;rA;rU2p;rG;mA;rU;mG;rC;mA;rG;mG;rA;mC;rU;mC$ (SEQ ID NO: 75) | | 2'5' 7 |
| RAC1_2_S1409 | rG;rA;rG;rU;rC;rC;rU;rG;rC;rA;rU;rC;rA;rU;rU;rU;rG;rA;rA$ (SEQ ID NO: 29) | mU;rU;mC;rA;mA;rA;rU2p;rG2p;mA;rU;mG;rC;mA;rG;mG;rA;mC;rU;mC$ (SEQ ID NO: 76) | | 2'5' 7-8 |
| RAC1_2_S1410 | rG;rA;rG;rU;rC;rC;rU;rG;rC;rA;rU;rC;rA;rU;rU;rU;rG;rA;rA$ (SEQ ID NO: 30) | mU;rU;mC;rA;mA;rA;mU;rG2p;mA;rU;mG;rC;mA;rG;mG;rA;mC;rU;mC$ (SEQ ID NO: 77) | | 2'5' 8 |
| RAC1_2_S1411 | rG;rA;rG;rU;rC;rC;rU;rG;rC;rA;rU;rC;rA;rU;rU;rU;rG;rA;rA$ (SEQ ID NO: 31) | mU;rU;mC;rA;mA;LdA;mU;rG;mA;rU;mG;rC;mA;rG;mG;rA;mC;rU;mC$ (SEQ ID NO: 78) | | L-DNA 6 |
| RAC1_2_S1412 | rG;rA;rG;rU;rC;rC;rU;rG;rC;rA;rU;rC;rA;rU;rU;rU;rG;rA;rA$ (SEQ ID NO: 32) | mU;rU;mC;rA;mA;rA;LdT;rG;mA;rU;mG;rC;mA;rG;mG;rA;mC;rU;mC$ (SEQ ID NO: 79) | | L-DNA 7 |
| RAC1_2_S1413 | rG;rA;rG;rU;rC;rC;rU;rG;rC;rA;rU;rC;rA;rU;rU;rU;rG;rA;rA$ (SEQ ID NO: 33) | mU;rU;mC;rA;mA;rA;mU;LdG;mA;rU;mG;rC;mA;rG;mG;rA;mC;rU;mC$ (SEQ ID NO: 80) | | L-DNA 8 |
| RAC1_2_S1653 | rG;rA;rG;rU;rC;rC;rU;rG;rC;rA;rU;rC;rA;dT;dT;dT;dG;dA;dA$ (SEQ ID NO: 34) | mU;rU;mC;rA;rA2p;rA;mU;rG;mA;rU;mG;rC;mA;rG;mG;rAmC;rU;mC$ (SEQ ID NO: 81) | DNA 14-19 | 2'5' 5 |

TABLE A-continued

Synthesized sense strand and antisense strand for generating dsRNA molecules targeting RAC1
(SEQ ID NOS 12-105, respectively, in order of columns):

| Name | Sense strand 5->3 code | AntiSense strand 5->3 code | Unconventional moieties sense (5' > 3') | Unconventional moieties antisense (5' > 3') |
|---|---|---|---|---|
| RAC1_2_S1654 | rG;rA;rG;rU;rC;rC;rU; rG;rC;rA;rU;rC;rA;dT; dT;dT;dG;dA;dA$ (SEQ ID NO: 35) | mU;rU;mC;rA;rA2p;rA2p; mU;rG;mA;rU;mG;rC;mA; rG;mG;rA;mC;rU;mC$ (SEQ ID NO: 82) | DNA 14-19 | 2'5' 5, 6 |
| RAC1_2_S1655 | rG;rA;rG;rU;rC;rC;rU; rG;rC;rA;rU;rC;rA;dT; dT;dT;dG;dA;dA$ (SEQ ID NO: 36) | mU;rU;mC;rA;rA;rA2p;mU; rG;mA;rU;mG;rC;mA;rG; mG;rA;mC;rU;mC$ (SEQ ID NO: 83) | DNA 14-19 | 2'5' 6 |
| RAC1_2_S1656 | rG;rA;rG;rU;rC;rC;rU; rG;rC;rA;rU;rC;rA;dT; dT;dT;dG;dA;dA$ (SEQ ID NO: 37) | mU;rU;mC;rA;rA;rA2p;rU2p; rG;mA;rU;mG;rC;mA; rG;mG;rA;mC;rU;mC$ (SEQ ID NO: 84) | DNA 14-19 | 2'5' 6-7 |
| RAC1_2_S1657 | rG;rA;rG;rU;rC;rC;rU; rG;rC;rA;rU;rC;rA;dT; dT;d;dG;dA;dA$ (SEQ ID NO: 38) | mU;rU;mC;rA;mA;rA;rU2p; rG;mA;rU;mG;rC;mA; rG;mG;rA;mC;rU;mC$ (SEQ ID NO: 85) | DNA 14-19 | 2'5' 7 |
| RAC1_2_S1658 | rG;rA;rG;rU;rC;rC;rU; rG;rC;rA;rU;rC;rA;dT; dT;dT;dG;dA;dA$ (SEQ ID NO: 39) | mU;rU;mC;rA;mA;rA;rU2p; rG2p;mA;rU;mG;rC;mA; rG;mG;rA;mC;rU;mC$ (SEQ ID NO: 86) | DNA 14-19 | 2'5' 7-8 |
| RAC1_2_S1659 | rG;rA;rG;rU;rC;rC;rU; rG;rC;rA;rU;rC;rA;dT; dT;dT;dG;dA;dA$ (SEQ ID NO: 40) | mU;rU;mC;rA;mA;rA;mU; rG2p;mA;rU;mG;rC;mA; rG;G;rA;mC;rU;mC$ (SEQ ID NO: 87) | DNA 14-19 | 2'5' 8 |
| RAC1_2_S1660 | rG;rA;rG;rU;rC;rC;rU; rG;rC;rA;rU;rC;rA;dT; dT;dT;dG;dA;dA$ (SEQ ID NO: 41) | mU;rU;mC;rA;mA;LdA; mU;rG;mA;rU;mG;rC;mA; rG;mG;rA;mC;rU;mC$ (SEQ ID NO: 88) | DNA 14-19 | L-DNA 6 |
| RAC1_2_S1661 | rG;rA;rG;rU;rC;rC;rU; rG;rC;rA;rU;rC;rA;dT; dT;dT;dG;dA;dA$ (SEQ ID NO: 42) | mU;rU;mC;rA;mA;rA;LdT; rG;mA;rU;mG;rC;mA;rG; mG;rA;mC;rU;mC$ (SEQ ID NO: 89) | DNA 14-19 | L-DNA 7 |
| RAC1_2_S1662 | rG;rA;rG;rU;rC;rC;rU; rG;rC;rA;rU;rC;rA;dT; dT;dT;dG;dA;dA$ (SEQ ID NO: 43) | mU;rU;mC;rA;mA;rA;mU; LdG;mA;rU;mG;rC;mA; rG;mG;rA;mC;rU;mC$ (SEQ ID NO: 90) | DNA 14-19 | L-DNA 8 |
| RAC1_2_S710 | rG;rA;rG;rU;rC;rC;rU; rG;rC;rA;rU;rC;rA;rU; rU;rU;rG;rA;rA$ (SEQ ID NO: 44) | rU;rU;rC;rA;rA;rA;rU;rG; rA;rU;rG;rC;rA;rG;rG;rA; rC;rU;rC$ (SEQ ID NO: 91) | | |
| RAC1_2_S73 | rG;mA;rG;mU;rC;mC; rU;mG;rC;mA;rU;mC; rA;mU;rU;mU;rG;mA;rA$ (SEQ ID NO: 45) | mU;rU;mC;rA;mA;rA;mU; rG;mA;rU;mG;rC;mA;rG; mG;rA;mC;rU;mC$ (SEQ ID NO: 92) | | |
| RAC1_2_S781 | rG;rA;rG;rU;rC;rC;rU; rG;rC;rA;rU;rC;rA;rU; rU;rU;rG;rA;rA$ (SEQ ID NO: 46) | mU;rU;mC;rA;mA;rA;mU; rG;mA;rU;mG;rC;mA;rG; mG;rA;mC;rU;mC$ (SEQ ID NO: 93) | | |
| RAC1_2_S792 | rG;rA;rG;rU;rC;rC;rU; rG;rC;rA;rU;rC;rA;dT; dT;dT;dG;dA;dA$ (SEQ ID NO: 47) | mU;rU;mC;rA;mA;rA;mU; rG;mA;rU;mG;rC;mA;rG; mG;rA;mC;rU;mC$ (SEQ ID NO: 94) | DNA: 14-19 | |
| RAC1_2_S985 | rG;mA;rG;mU;rC;mC;rU; mG;rC;mA;rU;mC;rA; mU;rU;mU;rG;mA;rA$ (SEQ ID NO: 48) | mU;rU;mC;rA;mA;rA;mU; rG;tnaA;rU;mG;rC;mA; rG;mG;rA;mC;rU;mC$ (SEQ ID NO: 95) | | TNA 9 |
| RAC1_2_S988 | rG;mA;rG;mU;rC;mC;rU; mG;rC;mA;rU;mC;rA; mU;rU;mU;rG;mA;rA$ (SEQ ID NO: 49) | mU;rU;tnaC;tnaA;rA;tnaA; rU;rG;tnaA;rU;rG;tnaC;tnaA; rG;G;tnaA;tnaC;rU;tnaC$ (SEQ ID NO: 96) | | TNA 3, 4, 6, 9, 12, 13,16, 17, 19 |
| RAC1_2_S987 | rG;tnaA;rG;rU;tnaC;tnaC;rU; rG;rC;tnaA;rU;tnaC;tnaA; rU;rU;rU;rG;tnaA;tnaA$ (SEQ ID NO: 50) | mU;rU;mC;rA;mA;rA;mU; rG;mA;rU;mG;rC;mA;rG; mG;rA;mC;rU;mC$ (SEQ ID NO: 97) | TNA 2, 5, 6, 10, 12, 13, 18,19 | |
| RAC1_2_S1 | rG;rA;rG;rU;rC;rC;rU;rG; rC;rA;rU;rC;rA;rU;rU; rU;rG2p;rA2p;rA$ (SEQ ID NO: 51) | mU;rU;mC;rA;mA;rA;mU; rG;mA;rU;mG;rC;mA;rG; mG;rA;mC;rU;mC$ (SEQ ID NO: 98) | 2'5' 17, 18 | |
| RAC1_2_S1118 | rG;rA;rG;rU2p;rC2p;rC2p;rU2p; rG;rC2p;rA;rU2p;rC2p;rA;rU2p; rU2p;rU2p;rG;rA;rA$ (SEQ ID NO: 52) | mU;rU;mC;rA;mA;rA;mU; rG;mA;rU;mG;rC;mA;rG; mG;rA;mC;rU;mC$ (SEQ ID NO: 99) | 2'5' 4-7, 9, 11-12, 14-16 | |

TABLE A-continued

Synthesized sense strand and antisense strand for generating dsRNA molecules targeting RAC1
(SEQ ID NOS 12-105, respectively, in order of columns):

| Name | Sense strand 5->3 code | AntiSense strand 5->3 code | Unconventional moieties sense (5' > 3') | Unconventional moieties antisense (5' > 3') |
|---|---|---|---|---|
| RAC1_2_S1119 | rG;rA;rG;rU2p;rC2p;rC2p;rU2p; rG;rC;rA;rU2p;rC2p;rA; rU2p;rU2p;rU2p;rG;rA;rA$ (SEQ ID NO: 53) | mU;rU;mC;rA;mA;rA;mU; rG;mA;rU;mG;rC;mA;rG; mG;rA;mC;rU;mC$ (SEQ ID NO: 100) | 2'5' 4-7, 11-12, 14-16 | |
| RAC1_2_S1120 | rG;rA2p;rG;rU2p;rC;rC2p;rU; rG2p;rC;rA2p;rU;rC2p;rA; rU2p;rU;rU2p;rG;rA2p;rA$ (SEQ ID NO: 54) | mU;rU;mC;rA;mA;rA;mU; rG;mA;rU;mG;rC;mA;rG; mG;rA;mC;rU;mC$ (SEQ ID NO: 101) | 2'5' 2, 4, 6, 8, 10, 12, 14, 16, 18 | |
| RAC1_2_S1121 | rG;rA;rG;rU;rC;rC;rU;rG;rC; rA;rU;rC;rA;rU2p;rU2p; rU2p;rG2p;rA2p;rA$ (SEQ ID NO: 55) | mU;rU;mC;rA;mA;rA;mU; rG;mA;rU;mG;rC;mA;rG; mG;rA;mC;rU;mC$ (SEQ ID NO: 102) | 2'5' 14-18 | |
| RAC1_2_S1122 | rG;rA;rG;rU;rC;rC;rU;rG; rC;rA;rU;rC;rA;rU;rU; rU2p;rG2p;rA2p;rA$ (SEQ ID NO: 56) | mU;rU;mC;rA;mA;rA;mU; rG;mA;rU;mG;rC;mA;rG; mG;rA;mC;rU;mC$ (SEQ ID NO: 103) | 2'5' 16-18 | |
| RAC1_2_S1123 | rG2p;rA2p;rG2p;rU2p;rC2p; rC2p;rU2p;rG2 p;rC2p;rA2p; rU2p;rC2p;rA2p;rU2p;rU2p; rU2p;rG2p;rA2p;rA$ (SEQ ID NO: 57) | mU;rU;mC;rA;mA;rA;mU; rG;mA;rU;mG;rC;mA;rG; mG;rA;mC;rU;mC$ (SEQ ID NO: 104) | 2'5' 1-18 | |
| RAC1_2_S781 | rG;rA;rG;rU;rC;rC;rU; rG;rC;rA;rU;rC;rA;rU; rU;rU;rG;rA;rA$ (SEQ ID NO: 58) | mU;rU;mC;rA;mA;rA;mU; rG;mA;rU;mG;rC;mA;rG; mG;rA;mC;rU;mC$ (SEQ ID NO: 105) | | |

TABLE B1

Synthesized sense strand and antisense strand for generating dsRNA molecules tested targeting MYD88
(SEQ ID NOS 106-181, respectively, in order of columns)

| Name | Sense strand 5->3 | Antisense strand 5->3 | Unconventional moieties sense (5' > 3') | Unconventional moieties antisense (5' > 3') |
|---|---|---|---|---|
| MYD88_11_S1106 | zidB;rG;rA;rA;rU;rG;rU;rG; rA;rC;rU;rU;rC;rC;rA2p; rG2p;rA2p;rC2p;rC2p;rA$ (SEQ ID NO: 106) | mU;rG;rG;dT;mC;dT;mG;rG; mA;rA;mG;dT;mC;rA;mC;rA; mU;dT;mC;zdT;zdT$ (SEQ ID NO: 144) | 5' inverted abasic 2'5': 14-18 | [DNA: 4, 6, 12, 18 3' dTdT |
| MYD88_11_S1107 | zidB;rG;rA;rA;rU;rG;rU;rG; rA;rC;rU;rU;rC;rC;rA2p; rG2p;rA2p;rC2p;rC2p;rA$ (SEQ ID NO: 107) | mU;rG;rG;mU;mC;mU;rG;rG; mA;rA;rG;mU;mC;rA;mC;rA; mU;mU;mC;zdT;zdT$ (SEQ ID NO: 145) | 5' inverted abasic 2'5': 14-18 | 3' dTdT |
| MYD88_11_S1108 | zidB;rG;rA;rA;rU;rG;rU;rG; rA;rC;rU;rU;rC;rC;rA; rG2p;rA2p;rC2p;rC2p;rA$ (SEQ ID NO: 108) | mU;rG;rG;dT;mC;dT;mG;rG; mA;rA;mG;dT;mC;rA;mC;rA; mU;dT;mC;zdT;zdT$ (SEQ ID NO: 146) | 5' inverted abasic 2'5': 14-18 | IDNA: 4, 6, 12, 18 3' dTdT |
| MYD88_11_S1109 | zidB;rG;rA;rA;rU;rG;rU;rG; rA;rC;rU;rU;rC;rC;rA; rG2p;rA2p;rC2p;rC2p;rA$ (SEQ ID NO: 109) | mU;rG;rG;mU;mC;mU;rG;rG; mA;rA;rG;mU;mC;rA;mC;rA; mU;mU;mC;zdT;zdT$ (SEQ ID NO: 147) | 5' inverted abasic 2'5': 14-18 | 3' dTdT |
| MYD88_11_S1110 | zidB;rG;rA;rA;rU;rG;rU;rG; rA;rC;rU;rU;rC;rC;rA; rG;rA2p;rC2p;rC2p;rA$ (SEQ ID NO: 110) | mU;rG;rG;dT;mC;dT;mG;rG; mA;rA;mG;dT;mC;rA;mC;rA; mU;dT;mC;zdT;zdT$ (SEQ ID NO: 148) | 5' inverted abasic 2'5': 16-18 | IDNA: 4, 6, 12, 18 3' dTdT |
| MYD88_11_S1111 | zidB;rG;rA;rA;rU;rG;rU;rG; rA;rC;rU;rU;rC;rC;rA; rG;rA2p;rC2p;rC2p;rA$ (SEQ ID NO: 111) | mU;rG;rG;mU;mC;mU;rG;rG; mA;rA;rG;mU;mC;rA;mC;rA; mU;mU;mC;zdT;zdT$ (SEQ ID NO: 149) | 5' inverted abasic 2'5': 16-18 | t3' dTdT |
| MYD88_11_S1112 | zidB;rG;rA;rA;rU2p;rG;rU2p; rG;rA;rC2p;rU2p;rU2p;rC2p; rC2p;rA;rG;rA;rC2p;rC2p;rA$ (SEQ ID NO: 112) | mU;rG;rG;dT;mC;dT;mG;rG; mA;rA;mG;dT;mC;rA;mC;rA; mU;dT;mC;zdT;zdT$ (SEQ ID NO: 150) | 5' inverted abasic 2'5': 4, 6, 9-13, 17-18 | [DNA: 4, 6, 12, 18 3' dTdT |
| MYD88_11_S1113 | zidB;rG;rA;rA;rU2p;rG;rU2p; rG;rA;rC2p;rU2p;rU2p;rC2p; rC2p;rA;rG;rA;rC2p;rC2p;rA$ (SEQ ID NO: 113) | mU;rG;rG;mU;mC;mU;rG;rG; mA;rA;rG;mU;mC;rA;mC;rA; mU;mU;mC;zdT;zdT$ (SEQ ID NO: 151) | 5' inverted abasic 2'5': 4, 6, 9-13, 17-18 | B' dTdT |

TABLE B1-continued

Synthesized sense strand and antisense strand for generating dsRNA molecules tested targeting MYD88
(SEQ ID NOS 106-181, respectively, in order of columns)

| Name | Sense strand 5->3 | Antisense strand 5->3 | Unconventional moieties sense (5' > 3') | Unconventional moieties antisense (5' > 3') |
|---|---|---|---|---|
| MYD88_11_S1114 | zidB;rG;rA2p;rA;rU2p;rG;rU2p; rG;rA2p;rC;rU2p;rU;rC2p;rC; rA2p;rG;rA2p;rC;rC2p;rA$ (SEQ ID NO: 114) | mU;rG;rG;dT;mC;dT;mG;rG; mA;rA;mG;dT;mC;rA;mC;rA; mU;dT;mC;zdT;zdT$ (SEQ ID NO: 152) | 5' inverted abasic 2'5': 2, 4, 6, 8, 10, 12, 14, 16, 18 | [DNA: 4, 6, 12, 18 3' dTdT |
| MYD88_11_S1115 | zidB;rG;rA2p;rA;rU2p;rG;rU2p; rG;rA2p;rC;rU2p;rU;rC2p;rC; rA2p;rG;rA2p;rC;rC2p;rA$ (SEQ ID NO: 115) | mU;rG;rG;mU;mC;mU;rG;rG; mA;rA;rG;mU;mC;rA;mC;rA; mU;mU;mC;zdT;zdT$ (SEQ ID NO: 153) | 5' inverted abasic 2'5': 2, 4, 6, 8, 10, 12, 14, 16, 18 | B' dTdT |
| MYD88_11_S1116 | zidB;rG;rA;rA;dT;rG;dT; rG;rA;dC;dT;dT;dC;dC; rA;rG;rA;dC;dC;rA$ (SEQ ID NO: 116) | mU;rG;rG;dT;mC;dT;mG;rG; mA;rA;mG;dT;mC;rA;mC;rA; mU;dT;mC;zdT;zdT$ (SEQ ID NO: 154) | 5' inverted abasic DNA: 4, 6, 9-13, 17, 18 | [DNA: 4, 6, 12, 18 B' dTdT |
| MYD88_11_S1117 | zidB;rG;rA;rA;dT;rG;dT; rG;rA;dC;dT;dT;dC;dC; rA;rG;rA;dC;dC;rA$ (SEQ ID NO: 117) | mU;rG;rG;mU;mC;mU;rG;rG; mA;rA;rG;mU;mC;rA;mC;rA; mU;mU;mC;zdT;zdT$ (SEQ ID NO: 155) | 5' inverted abasic DNA: 4, 6, 9-13, 17, 18 | B' dTdT |
| MYD88_11_S1159 | zidB;rG;rA;rA;rU;rG;rU;rG; rA;rC;rU;rU;rC;rC;rA; rG2p;rA2p;rC2p;rC2p;rA$ (SEQ ID NO: 118) | mU;rG;rG;mU;mC;mU;rG;rG; mA;rA;rG;mU;mC;rA;mC;rA; mU;mU;mC;zc3p;zc3p$ (SEQ ID NO: 156) | 5 ' inverted abasic 2'5': 15-18 | 3' dTdT |
| MYD88_11_S1260 | rG;rA;rA;rU;rG;rU;rG;rA; rC;rU;rU;rC;rC;rA;rG2p; rA2p;rC2p;rC2p;rA$ (SEQ ID NO: 119) | rU;mG;rG;mU;rC;mU;rG; mG;rA;rA;mG;rU;mC;rA; mC;rA;mU;rU;mC$ (SEQ ID NO: 157) | 2'5': 15-18 | B' dTdT |
| MYD88_11_S1262 | rG;rA;rA;rU;rG;rU;rG;rA; rC;rU;rU;rC;rC;rA;rG2p; rA2p;rC2p;rC2p;rA$ (SEQ ID NO: 120) | mU;rG;rG;mU;mC;mU;rG;rG; mA;rA;rG;mU;mC;rA;mC;rA; mU;mU;mC;zc3p;zc3p$ (SEQ ID NO: 158) | 2'5': 15-18 | B 'C3Pi-C3Pi |
| MYD88_11_S1264 | rG;rA;rA;rU;rG;rU;rG;rA; rC;rU;rU;rC;rC;rA;rG2p; rA2p;rC2p;rC2p;rA2p (SEQ ID NO: 121) | rU;mG;rG;mU;rC;mU;rG; mG;rA;rA;mG;rU;mC;rA; mC;rA;mU;rU;mC$ (SEQ ID NO: 159) | 2'5': 15-19 | |
| MYD88_11_S1266 | rG;rA;rA;rU;rG;rU;rG;rA; rC;rU;rU;rC;rC;rA;rG2p; rA2p;rC2p;rC2p;rA2p (SEQ ID NO: 122) | mU;rG;rG;mU;mC;mU;rG;rG; mA;rA;rG;mU;mC;rA;mC;rA; mU;mU;mC;zc3p;zc3p$ (SEQ ID NO: 160) | 2'5': 15-19 | B 'C3Pi-C3Pi |
| MYD88_11_S1268 | zc3p;rG;rA;rA;rU;rG;rU;rG; rA;rC;rU;rU;rC;rC;rA; rG2p;rA2p;rC2p;rC2p;rA2p (SEQ ID NO: 123) | rU;mG;rG;mU;rC;mU;rG; mG;rA;rA;mG;rU;mC;rA; mC;rA;mU;rU;mC$ (SEQ ID NO: 161) | 5' C3Pi 2'5': 15-19 | |
| MYD88_11_S1270 | zc3p;rG;rA;rA;rU;rG;rU;rG; rA;rC;rU;rU;rC;rC;rA; rG2p;rA2p;rC2p;rC2p;rA2p (SEQ ID NO: 124) | mU;rG;rG;mU;mC;mU;rG;rG; mA;rA;rG;mU;mC;rA;mC;rA; mU;mU;mC;zc3p;zc3p$ (SEQ ID NO: 162) | 5' C3Pi 2'5': 15-19 | B 'C3Pi-C3Pi |
| MYD88_11_S1272 | zc6Np;rG;rA;rA;rU;rG;rU; rG;rA;rC;rU;rU;rC;rC;rA; rG2p;rA2p;rC2p;rC2p;rA2p (SEQ ID NO: 125) | rU;mG;rG;mU;rC;mU;rG; mG;rA;rA;mG;rU;mC;rA; mC;rA;mU;rU;mC$ (SEQ ID NO: 163) | 5' aminoC6 2'5': 15-19 | |
| MYD88_11_S1274 | zc6Np;rG;rA;rA;rU;rG;rU; rG;rA;rC;rU;rU;rC;rC;rA; rG2p;rA2p;rC2p;rC2p;rA2p (SEQ ID NO: 126) | mU;rG;rG;mU;mC;mU;rG;rG; mA;rA;rG;mU;mC;rA;mC;rA; mU;mU;mC;zc3p;zc3p$ (SEQ ID NO: 164) | 5' aminoC6 2'5': 15-19 | 3'C3Pi-C3Pi |
| MYD88_11_S1276 | rG;rA;rA;rU;rG;rU;rG; rA;rC;rU;rU;rC;rC;rA; rG;rA;rC;rC;rA$ (SEQ ID NO: 127) | mU;rG;rG;mU;mC;mU;rG;rG; mA;rA;rG;mU;mC;rA;mC;rA; mU;mU;mC;zc3p;zc3p$ (SEQ ID NO: 165) | | B 'C3Pi-C3Pi |
| MYD88_11_S505 | rG;rA;rA;rU;rG;rU;rG; rA;rC;rU;rU;rC;rC;rA; rG;rA;rC;LdC;rA$ (SEQ ID NO: 128) | rU;mG;rG;mU;rC;mU;rG; mG;rA;rA;mG;rU;mC;rA; mC;rA;mU;rU;mC$ (SEQ ID NO: 166) | L-DNA: 18 | |
| MYD88_11_S782 | rG;rA;rA;rU;rG;rU;rG; rA;rC;rU;rU;rC;rC;rA; rG;rA;rC;rC;rA$ (SEQ ID NO: 129) | rU;mG;rG;mU;rC;mU;rG; mG;rA;rA;mG;rU;mC;rA; mC;rA;mU;rU;mC$ (SEQ ID NO: 167) | | |
| MYD88_11_S1325 | rG;rA;rA;rU;rG;rU;rG;rA; rC;rU;rU;rC;rC;rA;rG2p; rA2p;rC2p;rC2p;rA$ (SEQ ID NO: 130) | mU;rG;rG;mU;mC;mU;rG;rG; mA;rA;rG;mU;mC;rA;mC;rA; mU;mU;mC;zc3p;zc3p (SEQ ID NO: 168) | 2'5': 15-18 | 3'C3Pi-C3Pi |

TABLE B1-continued

Synthesized sense strand and antisense strand for generating dsRNA molecules tested targeting MYD88
(SEQ ID NOS 106-181, respectively, in order of columns)

| Name | Sense strand 5->3 | Antisense strand 5->3 | Unconventional moieties sense (5' > 3') | Unconventional moieties antisense (5' > 3') |
|---|---|---|---|---|
| MYD88_11_S1326 | rG;rA;rA;rU;rG;rU;rG;rA; rC;rU;rU;rC;rC;rA;rG2p; rA2p;rC2p;rC2p;rA2p (SEQ ID NO: 131) | mU;rG;rG;mU;mC;mU;rG;rG; mA;rA;rG;mU;mC;rA;mC;rA; mU;mU;mC;zc3p;zc3p (SEQ ID NO: 169) | 2'5': 15-18 | B'C3Pi-C3Pi |
| MYD88_11_S1327 | zc3p;rG;rA;rU;rG;rU;rG; rA;rC;rU;rU;rC;rC;rA; rG2p;rA2p;rC2p;rC2p;rA2p (SEQ ID NO: 132) | mU;rG;rG;mU;mC;mU;rG;rG; mA;rA;rG;mU;mC;rA;mC;rA; mU;mU;mC;zc3p;zc3p (SEQ ID NO: 170) | 5' C3Pi 2'5': 15-19 | 3'C3Pi-C3Pi |
| MYD88_11_S1328 | zc6Np;rG;rA;rA;rU;rG;rU; rG;rA;rC;rU;rU;rC;rC;rA; rG2p;rA2p;rC2p;rC2p;rA2p (SEQ ID NO: 133) | mU;rG;rG;mU;mC;mU;rG;rG; mA;rA;rG;mU;mC;rA;mC;rA; mU;mU;mC;zc3p;zc3p (SEQ ID NO: 171) | | B 'C3Pi-C3Pi |
| MYD88_11_S1329 | zidB;rG;rA;rA;rU;rG;rU; rG;rA;rC;rU;rU;rC;rC;rA; rG2p;rA2p;rC2p;rC2p;rA$ (SEQ ID NO: 134) | mU;rG;rG;mU;mC;mU;rG;rG; mA;rA;rG;mU;mC;rA;mC;rA; mU;mU;mC;zc3p;zc3p (SEQ ID NO: 172) | | 3'C3Pi-C3Pi |
| MYD88_11_S1291 | rG;rA;rA;rU;rG;rU;rG;rA; rC;rU;rU;rC;rC;tnaA;rG; tnaA;tnaC;tnaC;tnaA$ (SEQ ID NO: 135) | rU;mG;rG;mU;rC;mU;rG; mG;rA;rA;mG;rU;mC;rA; mC;rA;mU;rU;mC$ (SEQ ID NO: 173) | TNA 14, 16-19 | |
| MYD88_11_S1292 | rG;rA;rA;rU;rG;rU;rG;rA; rC;rU;rU;rC;tnaC;tnaA; rG;tnaA;tnaC;tnaC;tnaA$ (SEQ ID NO: 136) | rU;mG;rG;mU;rC;mU;rG; mG;rA;rA;mG;rU;mC;rA; mC;rA;mU;rU;mC$ (SEQ ID NO: 174) | TNA 13, 14, 16-19 | |
| MYD88_11_S1293 | rG;rA;rA;rU;rG;rU;rG;rA; rC;rU;rU;tnaC;tnaC;tnaA; rG;tnaA;tnaC;tnaC;tnaA$ (SEQ ID NO: 137) | rU;mG;rG;mU;rC;mU; rG;mG;rA;rA;mG;rU; mC;rA;mC;rA;mU;rU; mC$ (SEQ ID NO: 175) | TNA 12-14, 16-19 | |
| MYD88_11_S1297 | rG;rA;rA;rU;rG;rU;rG;rA; rC;rU;rU;rC;tnaC;tnaA; rG;tnaA;tnaC;tnaC;tnaA$ (SEQ ID NO: 138) | mU;rG;mG;rU;mC;rU;mG;rG; mA;rA;mG;rU;mC;rA;mC;rA; mU;rU;mC;zdT;zdT$ (SEQ ID NO: 176) | tna 13, 14, 16-19 | 3' dTdT |
| MYD88_11_S889 | rG;rA;rA;rU;rG;rU;rG; rA;rC;rU;rU;rC;rC;rA; rG;rA;rC;rC;rA$ (SEQ ID NO: 139) | mU;rG;mG;rU;mC;rU;mG;rG; mA;rA;mG;rU;mC;rA;mC;rA; mU;rU;mC;zdT;zdT$ (SEQ ID NO: 177) | | B' dTdT |
| MYD88_11_S782 | rG;rA;rA;rU;rG;rU;rG; rA;rC;rU;rU;rC;rC;rA; rG;rA;rC;rC;rA$ (SEQ ID NO: 140) | rU;mG;rG;mU;rC;mU;rG; mG;rA;rA;mG;rU;mC;rA; mC;rA;mU;rU;mC$ (SEQ ID NO: 178) | | |
| MYD88_11_S1788 | rG;rA;rA;rU;rG;rU;rG;rA; rC;rU;rU;rC;rC;tnaA; rG;tnaA;tnaC;tnaC;tnaA$ (SEQ ID NO: 141) | mU;rG;rG;mU;mC;mU;rG;rG; mA;rA;rG;mU;mC;rA;mC;rA; mU;mU;mC;zc3p;zc3p$ (SEQ ID NO: 179) | TNA 14, 16, 17, 18, 19 | L3 'C3Pi-C3Pi |
| MYD88_11_S1789 | rG;rA;rA;rU;rG;rU;rG;rA; rC;rU;rU;rC;tnaC;tnaA; rG;tnaA;tnaC;tnaC;tnaA$ (SEQ ID NO: 142) | mU;rG;rG;mU;mC;mU;rG;rG; mA;rA;rG;mU;mC;rA;mC;rA; mU;mU;mC;zc3p;zc3p$ (SEQ ID NO: 180) | TNA 13, 14, 16, 17, 18, 19 | 3'C3Pi-C3Pi |
| MYD88_11_S1790 | rG;rA;rA;rU;rG;rU;rG;rA; rC;rU;rU;tnaC;tnaC;tnaA; rG;tnaA;tnaC;tnaC;tnaA$ (SEQ ID NO: 143) | mU;rG;rG;mU;mC;mU;rG;rG; mA;rA;rG;mU;mC;rA;mC;rA; mU;mU;mC;zc3p;zc3p$ (SEQ ID NO: 181) | TNA 12, 13, 14, 16, 17, 18, 19 | B 'C3Pi-C3Pi |

TABLE C1

Synthesized sense strand and antisense strand for generating dsRNA molecules
targeting p53 and comprising TNA in sense strand 09-mer strand).
(SEQ ID NOS 182-189, respectively, in order of columns)

| Name | Sense 5->3 | AntiSense 5->3 | TNA sense (positions 5' > 3') | TNA Antisense (positions 5' > 3') |
|---|---|---|---|---|
| P53_17_S981 | rG;rA;rA;rG;rA;rA;rA;rU; rU;rU;rC;rC;rG;tnaC;tnaA; tnaA;tnaA;tnaA$ (SEQ ID NO: 182) | mU;rU;mU;rU;mG;rC;mG; rG;mA;rA;mA;rU;mU; rU;mU;rC;mU;rU;mC$ (SEQ ID NO: 186) | 15-19 | — |

TABLE C1-continued

Synthesized sense strand and antisense strand for generating dsRNA molecules targeting p53 and comprising TNA in sense strand 09-mer strand).
(SEQ ID NOS 182-189, respectively, in order of columns)

| Name | Sense 5->3 | AntiSense 5->3 | TNA sense (positions 5' > 3') | TNA Antisense (positions 5' > 3') |
|---|---|---|---|---|
| P53_17_S982 | rG;rA;rA;rG;rA;rA;rA;rA;rU; rU;rU;rC;tnaC;rG;tnaC;tnaA; tnaA;tnaA;tnaA$ (SEQ ID NO: 183) | mU;rU;mU;rU;mG;rC;mG; rG;mA;rA;mA;rU;mU; rU;mU;rC;mU;rU;mC$ (SEQ ID NO: 187) | 13, 15-19 | — |
| P53_17_S998 | rG;rA;rA;rG;rA;rA;rA;rA;rU; mU;rU;rC;rC;rG;rC;rA;rA;rA; rA$ (SEQ ID NO: 184) | mU;rU;mU;rU;mG;rC;mG; rG;mA;rA;mA;rU;mU; rU;mU;rC;mU;rU;mC$ (SEQ ID NO: 188) | — | — |
| P53_17_S980 | rG;tnaA;rA;rG;rA;tnaA;rA; tnaA;rU;mU;rU;tnaC;tnaC; rG;rC;tnaA;rA;tnaA;rA$ (SEQ ID NO: 185) | mU;rU;mU;rU;mG;rC;mG; rG;mA;rA;mA;rU;mU; rU;mU;rC;mU;rU;mC$ (SEQ ID NO: 189) | 2, 5, 6, 10, 12, 13, 16 18, 19 | — |

TABLE C2

Synthesized sense strand and antisense strand for generating dsRNA molecules targeting p53 and comprising pseudoUridine (psiU) in positions 9 and 10 of sense strand 19-mer strand).
(SEQ ID NOS 190-205, respectively, in order of columns)

| Name | Sense | Antisense | tpsiU sense tpositions (5' > 3') | tpsiU antisense positions (5' > 3') |
|---|---|---|---|---|
| P53_17_S1172 | rG;rA;rA;rG;rA;rA;rA;rA; psiU;psiU;rU;rC;rC;rG;rC; rA;rA;rA;rA (SEQ ID NO: 190) | rU;rU;rU;rU;rG;rC;rG;rG; rA;rA;rA;rU;rU;rU;rU;rC; rU;rU;rC (SEQ ID NO: 198) | 9-10 | |
| P53_17_S1173 | rG;rA;rA;rG;rA;rA;rA;rA; psiU;psiU;psiU;rC;rC;rG; rC;rA;rA;rA;rA (SEQ ID NO: 191) | rU;rU;rU;rU;rG;rC;rG;rG; rA;rA;rA;rU;rU;rU;rU;rC; rU;rU;rC (SEQ ID NO: 199) | 9-11 | |
| P53_17_S1175 | rG;rA;rA;rG;rA;rA;rA;rA; psiU;psiU;rU;rC;rC;rG;rC; rA;rA;rA;rA (SEQ ID NO: 192) | rU;rU;rU;rU;rG;rC;rG;rG; rA;rA;rA;rU;rU;rU;rU;rC; psiU;psiU;rC (SEQ ID NO: 200) | 9-10 | 17-18 |
| P53_17_S1176 | rG;rA;rA;rG;rA;rA;rA;rA; psiU;psiU;psiU;rC;rC;rG; rC;rA;rA;rA;rA (SEQ ID NO: 193) | rU;rU;rU;rU;rG;rC;rG;rG; rA;rA;rA;rU;rU;rU;rU;rC; psiU;psiU;rC (SEQ ID NO: 201) | 9-11 | 17-18 |
| P53_17_S1178 | rG;rA;rA;rG;rA;rA;rA;rA; psiU;psiU;rU;rC;rC;rG;rC; rA;rA;rA;rA (SEQ ID NO: 194) | psiU;psiU;psiU;rU;rG;rC; rG;rG;rA;rA;rU;rU;rU; rU;rC;psiU;psiU;rC (SEQ ID NO: 202) | 9-10 | 1-3, 17-18 |
| P53_17_S1179 | rG;rA;rA;rG;rA;rA;rA;rA; psiU;psiU;psiU;rC;rC;rG; rC;rA;rA;rA;rA (SEQ ID NO: 195) | psiU;psiU;psiU;rU;rG;rC; rG;rG;rA;rA;rU;rU;rU; rU;rC;psiU;psiU;rC (SEQ ID NO: 203) | 9-11 | 1-3, 17-18 |
| P53_17_S1181 | rG;rA;rA;rG;rA;rA;rA;rA; psiU;psiU;rU;rC;rC;rG;rC; rA;rA;rA;rA (SEQ ID NO: 196) | psiU;psiU;psiU;rU;rG;rC; rG;rG;rA;rA;rU;rU;rU; rU;rC;rU;rU;rC (SEQ ID NO: 204) | 9-10 | 1-3 |
| P53_17_S1182 | rG;rA;rA;rG;rA;rA;rA;rA; psiU;psiU;psiU;rC;rC;rG; rC;rA;rA;rA;rA (SEQ ID NO: 197) | psiU;psiU;psiU;rU;rG;rC; rG;rG;rA;rA;rU;rU;rU; rU;rC;rU;rU;rC (SEQ ID NO: 205) | 9-11 | 1-3 |

TABLE D

Synthesized sense strands and antisense strands for generating dsRNA molecules targeting artificial polynucleotide sequence (STRUC) with multiple rA and rC at 3' terminus of sense strand
(SEQ ID NOS 206-231, respectively, in order of columns)

| Name | Sense 5->3 r rC tn | AntiSense 5->3 mUr | unconventional sense (positions 5' > 3') | unconventional Antisense (positions 5' > 3') |
|---|---|---|---|---|
| STRUC_2_S1302 | rA;rG;rG;rG;rC;rG;rU;rC; rA;rU;rC;rC;rA;rA;tnaC; tnaA;tnaC;tnaA;tnaA$ (SEQ ID NO: 206) | mU;rU;mG;rU;mG;rU;mU; rG;mG;rA;mU;rG;mA;rC;mG; rC;mC;rC;mU;zdT;zdT$ (SEQ ID NO: 219) | TNA 15-19 | 3' dTdT |

TABLE D-continued

Synthesized sense strands and antisense strands for generating dsRNA molecules targeting artificial polynucleotide sequence (STRUC) with multiple rA and rC at 3' terminus of sense strand
(SEQ ID NOS 206-231, respectively, in order of columns)

| Name | Sense 5->3<br>r rC tn | AntiSense 5->3<br>mUr | unconventional sense (positions 5' > 3') | unconventional Antisense (positions 5' > 3') |
|---|---|---|---|---|
| STRUC_2_S1303 | rA;rG;rG;rG;rC;rG;rU;rC;<br>rA;rU;rC;rC;rA;tnaA;tnaC;<br>tnaA;tnaC;tnaA;tnaA$<br>(SEQ ID NO: 207) | mU;rU;mG;rU;mG;rU;mU;<br>rG;mG;rA;mU;rG;mA;rC;mG;<br>rC;mC;rC;mU;zdT;zdT$<br>(SEQ ID NO: 220) | TNA 14-19 | G' dTdT |
| STRUC_2_S1304 | rA;rG;rG;rG;rC;rG;rU;rC;<br>rA;rU;rC;rC;tnaA;tnaA;<br>tnaC;tnaA;tnaC;tnaA;tnaA$<br>(SEQ ID NO: 208) | mU;rU;mG;rU;mG;rU;mU;<br>rG;mG;rA;mU;rG;mA;rC;mG;<br>rC;mC;rC;mU;zd T;zdT$<br>(SEQ ID NO: 221) | TNA 13-19 | G' dTdT |
| STRUC_2_S1305 | rA;rG;rG;rG;rC;rG;rU;rC;<br>rA;rU;rC;tnaC;tnaA;tnaA;<br>tnaC;tnaA;tnaC;tnaA;tnaA$<br>(SEQ ID NO: 209) | mU;rU;mG;rU;mG;rU;mU;<br>rG;mG;rA;mU;rG;mA;rC;<br>mG;rC;mC;rC;mU;zdT;zdT$<br>(SEQ ID NO: 222) | TNA 12-19 | G' dTdT |
| STRUC_2_S1306 | rA;rG;rG;rG;rC;rG;rU;rC;<br>rA;rU;tnaC;tnaC;tnaA;tnaA;<br>tnaC;tnaA;tnaC;tnaA;tnaA$<br>(SEQ ID NO: 210) | mU;rU;mG;rU;mG;rU;mU;<br>rG;mG;rA;mU;rG;mA;rC;<br>mG;rC;mC;rC;mU;zdT;zdT$<br>(SEQ ID NO: 223) | TNA 11-19 | G' dTdT |
| STRUC_2_S216 | rA;mG;mG;rC;mG;rU;<br>mC;rA;mU;rC;mC;rA;mA;<br>rC;mA;rC;mA;rA;zdT;zdT$<br>(SEQ ID NO: 211) | mU;rU;mG;rU;mG;rU;mU;<br>rG;mG;rA;mU;rG;mA;rC;<br>mG;rC;mC;rC;mU;zdT;zdT$<br>(SEQ ID NO: 224) | 3' dTdT | G' dTdT |
| STRUC_2_S1259 | rA;rG;rG;rG;rC;rG;rU;rC;<br>rA;rU;rC;rC;rA;rA;rC2p;<br>rA2p;rC2p;rA2p;rA$<br>(SEQ ID NO: 212) | mU;rU;mG;rU;mG;rU;mU;<br>rG;mG;rA;mU;rG;mA;rC;<br>mG;rC;mC;rC;mU;zdT;zdT$<br>(SEQ ID NO: 225) | 2'5' 15-18 | G' dTdT |
| STRUC_2_S1322 | rA;mG;mG;rC;mG;rU;<br>mC;rA;mU;rC;mC;rA;mA;<br>rC;mA;rC;mA;rA;zdT;zdT$<br>(SEQ ID NO: 213) | dT;mU;rG;mU;rG;mU;mU;<br>rG;mG;rA;mU;rG;rA;dC;<br>rG;mC;mC;mC;mU;zdT;zdT$<br>(SEQ ID NO: 226) | 3' dTdT | ONA: 1<br>G' dTdT |
| STRUC_2_S1315 | rA;rG;rG;rG;rC;rG;rU;rC;<br>rA;rU;rC;rC;rA;rA;tnaC;<br>tnaA;tnaC;tnaA;tnaA$<br>(SEQ ID NO: 214) | dT;mU;rG;mU;rG;mU;mU;<br>rG;mG;rA;mU;rG;rA;dC;<br>rG;mC;mC;mC;mU;zdT;zdT$<br>(SEQ ID NO: 227) | TNA 15-19 | ONA: 1<br>G' dTdT |
| STRUC_2_S1316 | rA;rG;rG;rG;rC;rG;rU;rC;<br>rA;rU;rC;rC;rA;tnaA;tnaC;<br>tnaA;tnaC;tnaA;tnaA$<br>(SEQ ID NO: 215) | dT;mU;rG;mU;rG;mU;mU;<br>rG;mG;rA;mU;rG;rA;dC;<br>rG;mC;mC;mC;mU;zdT;zdT$<br>(SEQ ID NO: 228) | TNA 14-19 | ONA: 1<br>G' dTdT |
| STRUC_2_S1317 | rA;rG;rG;rG;rC;rG;rU;rC;<br>rA;rU;rC;rC;tnaA;tnaA;<br>tnaC;tnaA;tnaC;tnaA;tnaA$<br>(SEQ ID NO: 216) | dT;mU;rG;mU;rG;mU;mU;<br>rG;mG;rA;mU;rG;rA;dC;<br>rG;mC;mC;mC;mU;zdT;zdT$<br>(SEQ ID NO: 229) | TNA 13-19 | DNA: 1<br>G' dTdT |
| STRUC_2_S1318 | rA;rG;rG;rG;rC;rG;rU;rC;<br>rA;rU;rC;tnaC;tnaA;tnaA;<br>tnaC;tnaA;tnaC;tnaA;tnaA$<br>(SEQ ID NO: 217) | dT;mU;rG;mU;rG;mU;mU;<br>rG;mG;rA;mU;rG;rA;dC;<br>rG;mC;mC;mC;mU;zdT;zdT$<br>(SEQ ID NO: 230) | TNA 12-19 | ONA: 1<br>G' dTdT |
| STRUC_2_S1319 | rA;rG;rG;rG;rC;rG;rU;rC;<br>rA;rU;tnaC;tnaC;tnaA;tnaA;<br>tnaC;tnaA;tnaC;tnaA;tnaA$<br>(SEQ ID NO: 218) | dT;mU;rG;mU;rG;mU;mU;<br>rG;mG;rA;mU;rG;rA;dC;<br>rG;mC;mC;mC;mU;zdT;zdT$<br>(SEQ ID NO: 231) | TNA 11-19 | DNA: 1<br>G' dTdT |

TABLE E

Legend of the unmodified and modified modified nucleotides/unconventional moieties as used in the Tables herein.

| Code | Description |
|---|---|
| rA | riboadenosine-3'-phosphate; 3'-adenylic acid |
| rC | ribocytidine-3'-phosphate; 3'-cytidylic acid |
| rG | riboguanosine-3'-phosphate; 3'-guanylic acid |
| rU | ribouridine-3'-phosphate; 3'-uridylic acid |
| mA | 2'-O-methyladenosine-3'-phosphate; 2'-O-methyl-3'-adenylic acid |
| mC | 2'-O-methylcytidine-3'-phosphate; 2'-O-methyl-3'-cytidylic acid |
| mG | 2'-O-methylguanosine-3'-phosphate; 2'-O-methyl-3'-guanylic acid |
| mU | 2'-O-methyluridine-3'-phosphate; 2'-O-methyl-3'-uridylic acid |
| dA | deoxyriboadenosine-3'-phosphate; 2'-deoxyribo-3'-adenylic acid |
| dC | deoxyribocytidine-3'-phosphate; 2'-deoxyribo-3'-cytidylic acid |
| dG | deoxyriboguanosine-3'-phosphate; 2'-deoxyribo-3'-guanylic acid |
| dT | thymidine-3'-phosphate; 3'-thymidylic acid |
| rA2p | riboadenosine-2'-phosphate; 2'-adenylic acid (2'5' A) |
| rC2p | ribocytidine-2'-phosphate; 2'-cytidylic acid (2'5' C) |
| rG2p | riboguanosine-2'-phosphate; 2'-guanylic acid (2'5' G) |
| rU2p | ribouridine-2'-phosphate; 2'-uridylic acid (2'5'U) |
| LdA | L-deoxyriboadenosine-3'-phosphate (mirror image dA) |
| LdC | L-deoxyribocytidine-3'-phosphate (mirror image dC) |
| LdG | L-deoxyriboguanosine-3'-phosphate (mirror image dG) |
| LdT | L-deoxyribothymidine-3'-phosphate (mirror image dT) |
| dB | abasic deoxyribose-3'-phosphate; 1,2-dideoxy-D-ribofuranose-3'-phosphate; 1,4-anhydro-2-deoxy-D-ribitol-3-phosphate |
| zidB | Inverted abasic deoxyribose-5'-phosphate; At 5' = 5'-5' idAb; At 3' = 3'-3' idAb |

TABLE E-continued

Legend of the unmodified and modified
modified nucleotides/unconventional moieties
as used in the Tables herein.

| Code | Description |
|---|---|
| z | Prefix to indicate moiety covalently attached to 3' terminus or 5' terminus |
| zdT; zdT | 3' dTdT overhang |
| tnaA | a-L-threofuranosyl adenine |
| tnaC | a-L-threofuranosyl cytosine |
| tnaG | a-L-threofuranosyl guanine |
| tnaU | a-L-threofuranosyl uracil |
| psiU | pseudouridne |
| p | 5' phosphate |
| s | 5' phosphorothioate |
| C3 | C3 non-nucleotide overhang |
| $ | lacking a 3' linker (used together with above nucleotides at the 3' end of the sequence) |

In Vitro Testing of the dsRNA Molecules for the Target Genes

Knock down activity of the dsRNA disclosed herein are tested for example in cell lines endogenously expressing the target gene or in cells transfected with an expression vector comprising the target gene or a portion thereof.

Low-Throughput-Screen (LTS) for testing on target activity of double stranded RNA compounds.

About $2 \times 10^5$ human or rat cells endogenously expressing the target gene, were inoculated in 1.5 mL growth medium in order to reach 30-50% confluence after 24 hours. Cells were transfected with Lipofectamine2000® reagent to a final concentration of 0.01-5 nM per transfected cells. Cells were incubated at 37±1° C., 5% CO2 for 48 hours. siRNA transfected cells were harvested and RNA was isolated using EZ-RNA kit [Biological Industries (#20-410-100)].

Reverse transcription was performed as follows: Synthesis of cDNA was performed and target gene mRNA levels were determined by Real Time qPCR and normalized to those of the Cyclophilin A (CYNA, PPIA) mRNA for each sample. siRNA activity was determined based on the ratio of the target gene mRNA quantity in siRNA-treated samples versus non-transfected control samples.

IC50 Values are Determined as Follows:

About $1-2 \times 10^5$ human or rat cells endogenously expressing the target gene, are inoculated in 1.5 nit growth medium in order to reach 30-50% confluence. Cells are transfected with double stranded RNA molecules with Lipofectamine2000 reagent to reach final transfection concentrations ranging between 0.0029-100 nM. As negative control cells are treated with Lipofectamine™ 2000 reagent or with Synthetic randomized-sequence, non-targeting siRNA at final concentrations of 20-100 nM. Cy3-labeled siRNA transfected cells were used as positive control for transfection efficiency.

Cells are incubated at 37±1° C., 5% CO2 for 48 hours. siRNA transfected cells were harvested and RNA was isolated using EZ-RNA kit [Biological Industries (#20-410-100) Reverse transcription: Synthesis of cDNA is performed and target gene mRNA levels are determined by Real Time qPCR and normalized to those of the Cyclophilin A (CYNA, PPIA) mRNA for each sample.

The 1050 value of the tested RNAi activity is determined by constructing a dose-response curve using the activity results obtained with the various final siRNA concentrations. The dose response curve is constructed by plotting the relative amount of residual target mRNA versus the logarithm of transfected siRNA concentration. The curve is calculated by fitting the best sigmoid curve to the measured data.

The percent of inhibition of gene expression using specific siRNAs was determined using qPCR analysis of target gene in cells expressing the endogenous gene.

Serum Stability Assay

The modified compounds disclosed herein are tested for duplex stability in human serum or human tissue extract, as follows:

siRNA molecules at final concentration of 7 uM are incubated at 370 C in 100% human serum (Sigma Cat# H4522). (siRNA stock 100 uM diluted in human serum 1:14.29 or human tissue extract from various tissue types.). Five ul (5 ul) are added to 15 ul 1.5×TBE-loading buffer at different time points (for example 0, 30 min, 1 h, 3 h, 6 h, 8 h, 10 h, 16 h and 24 h). Samples are immediately frozen in liquid nitrogen and are kept at −20° C.

Each sample is loaded onto a non-denaturing 20% acrylamide gel, prepared according to methods known in the art. The oligos are visualized with ethidium bromide under UV light.

Exonuclease Stability Assay

To study the stabilization effect of 3' non-nucleotide moieties on a nucleic acid molecule the sense strand, the antisense strand and the annealed siRNA duplex are incubated in cytosolic extracts prepared from different cell types.

Extract: HCT116 cytosolic extract (12 mg/ml).

Extract buffer: 25 mM Hepes pH-7.3 at 37° C.; 8 mM MgCl; 150 mM NaCl with 1 mM DTT was added fresh immediately before use.

Method: 3.5 ml of test siRNA (100 mM), were mixed with 46.5 ml contain 120 mg of HCT116 cytosolic extract. The 46.5 ml consists of 12 ml of HCT116 extract, and 34.5 ml of the extract buffer supplemented with DTT and protease inhibitors cocktail/100 (Calbiochem, setIII-539134). The final concentration of the siRNA in the incubation tube is 7 mM. The sample was incubated at 37° C., and at the indicated time point 5 ml were moved to fresh tube, mixed with 15 ml of 1×TBE-50% Glycerol loading buffer, and snap frozen in Liquid N2. The final concentration of the siRNA in the loading buffer is 1.75 mM (21 ng siRNA/ml). For Analyses by native PAGE and EtBr staining 50 ng are loaded per lane. For Northern analyses 1 ng of tested siRNA was loaded per lane.

Innate Immune Response to dsRNA Molecules:

Fresh human blood (at RT) was mixed at 1:1 ratio with sterile 0.9% NaCl at RT, and gently loaded (1:2 ratio) on Ficoll (Lymphoprep, Axis-Shield cat#1114547). Samples were centrifuged at RT (22OC, 800 g) in a swinging centrifuge for 30 minutes, washed with RPMI1640 medium and centrifuged (RT, 250 g) for 10 minutes. Cells were counted and seeded at final concentration of $1.5 \times 10^6$ cell/ml in growth medium (RPMI1640+10% FBS+2 mN L-glutamine+1% Pen-Strep) and incubated for 1 hours at 37OC before dsRNA treatment. Cells were then treated with the test dsRNAs at different concentrations using the Lipofectamine™ 2000 reagent (Invitrogen) according manufacturer's instructions and incubated at 37° C. in a 5% $CO_2$ incubator for 24 hours.

As a positive control for IFN response, cells were treated with either poly(I:C), a synthetic analog of double strand RNA (dsRNA) which is a TLR3 ligand (InvivoGen Cat# tlrl-pic) at final concentrations of 0.25-5.0 µg/mL or to Thiazolaquinolone (CL075), a TLR 7/8 ligand (InvivoGen Cat# tlrl-c75) at final concentrations of 0.075-2 µg/mL. Cell treated with Lipofectamine® 2000 reagent were used as negative (reference) control for IFN response.

At about 24 hours following incubation, cells were collected and supernatant was transferred to new tubes. Samples were frozen immediately in liquid nitrogen and secretion of IL-6 and TNF-α cytokines was tested using IL-6, DuoSet ELISA kit (R&D System DY2060), and TNF-α, DuoSet ELISA kit (R&D System DY210), according to manufacturer's instructions. RNA was extracted from the cell pellets and mRNA levels of human genes IFIT1 (interferon-induced protein with tetratricopeptide repeats 1) and MX1 (myxovirus (influenza virus) resistance 1, interferon-inducible protein p78) were measured by qPCR. Measured mRNA quantities were normalized to the mRNA quantity of the reference gene peptidylprolyl isomerase A (cyclophilin A; CycloA). Induction of IFN-signaling was evaluated by comparing the quantity of mRNA from IFIT1 and MX1 genes from treated cells, relative to their quantities non-treated cells. The qPCR results are those that passed QC standards, i.e. the value of the standard curve slope was in the interval [−4, −3], R2 >0.99, no primer dimers. Results that did not pass the QC requirements were disqualified from analysis.

On-Target and Off-Target Testing of Double Stranded RNA Molecules

The purpose of this study was to assess the on-target activity and potential off-target activity of control (unmodified) and test (chemically modified) double stranded nucleic acid molecules (Bramsen 2010 NAR. 38(17):5761-73)

The two strands of a siRNA molecule have sequences with configurations that are sense and antisense with respect to the target gene mRNA. Within a cell, the antisense strand of siRNA, known as the guide strand (GS) is loaded into the RNA-induced silencing complex (RISC) and serves to guide the RNAi machinery to complementary sequences in target mRNA. The sense strand, known as the passenger strand (PS), is destroyed. When exact complementarity exists between the GS and the target mRNA the latter is cleaved by the RNaseH-like slicer activity of RISC.

In some cases a siRNA molecule may down-regulate unintended genes whose transcripts possess complementarity to the GS seed region (nucleotides in positions 2-8 [5'>3']) in the 3'-UTR. Without wishing to be bound to theory, this off-target effect may be mediated by a mechanism similar to that of target silencing by microRNAs (miRNAs). Another type of off-target activity of siRNA may occur due to loading of the sense strand (PS) into RISC. The unintended off-target effects of synthetic siRNAs can be reduced or abrogated by chemical modification of the initial siRNA sequence in the siRNA duplex. The test molecules were designed accordingly.

Test molecules were assessed for both on-target activity (activity to target mRNA) and off-target activity (activity to mRNA other than target mRNA) in the "guide-seed-sequence-and-passenger-strand-based activity assay" using the psiCHECK™ (Promega) plasmid constructs. The activity of test and control molecules was tested against either a full target sequence (nucleotide sequence fully complementary to the whole 19-base sequence of either the GS or PS of test molecule) or the seed-target sequence (sequence complementary to nucleotides 1-8 [5'>3'] of either the GS or PS of test molecule).

The test molecules were at least as active against the GS full target site than was the non-modified control siRNA. Test molecules were inactive towards the PS full target site, whereas the control non-modified siRNA demonstrated activity towards the same site. Both siRNAs were inactive against the GS seed-target sequence and the PS seed-target sequence sites.

Guide strand (GS) refers to the antisense strand of a double stranded RNA that is able to enter the RISC complex and guide silencing of the target RNA.

Passenger strand (PS) refers to the sense strand of a double stranded RNA.

Seed sequence refers to nucleotides 2-8 (5'>3') of the GS and relevant for the off-target recognition.

CM (complete match) refers to a synthetic DNA fragment with nucleotide sequence fully complementary to the guide strand of the double stranded RNA molecule. This DNA fragment is cloned in 3'UTR of a reporter gene and serves as a target for RNA silencing. (Castanotto & Rossi (2009). Nature, 22:426-33)

SM (seed match) refers to a synthetic DNA fragment with nucleotide sequence with full complementarity to the nucleotides 1-8 (5'>3') of the guide strand of the test molecule siRNA (1st nucleotide+seed). This DNA fragment is cloned in 3'UTR of a reporter gene and serves as a target for the seed-based "off-target" silencing.

The psiCHECK™ system enables evaluation of the GS (antisense) and the PS (sense strand) to elicit targeted and off-targeted effects, by monitoring the changes in expression levels of their target sequences. Four psiCHECK™-2-based (Promega) constructs were prepared for the evaluation of target activity and potential off-target activity of each test molecule GS and PS strands. In each of the constructs one copy or three copies of either the full target or the seed-target sequence, of test molecule PS or GS, was cloned into the multiple cloning site located downstream of the Renilla luciferase translational stop codon in the 3'-UTR region. The resulting vectors were termed:

1—GS-CM (guide strand, complete-match) vector containing one copy or three copies of the full target sequence (nucleotide sequence fully complementary to the whole 19-base sequence of the GS of the test molecule);

2—PS-CM (passenger strand, complete-match) vector containing one copy or three copies of the full target sequence (nucleotide sequence fully complementary to the whole 19-base sequence of the PS of the test molecule);

3—GS-SM (guide strand, seed-match) vector containing one copy or three copies of the seed region target sequence (sequence complementary to nucleotides 1-8 of the GS of the test molecule);

4—PS-SM (passenger strand, seed-match) vector containing one copy or three copies of the seed region target sequence (sequence complementary to nucleotides 1-8 of the PS of the test molecule).

The target sequences, with or without nucleotide substitutions in position 19 (position 1 of AS) were cloned downstream to the coding region of the Renilla luciferase reporter gene. The RNAi or seed-mediated activity of a test molecule toward any of these sequences results either in cleavage and subsequent degradation of the fusion mRNA (GS) or in translational inhibition (PS). In both cases protein expression is attenuated.

Cloning of Test Molecule GS and PS Seed and Full Target Sites

A single copy of the relevant target cloned in the 3'UTR of the reporter mRNA, Renilla Luciferase in the psi-CHECK™-2 (Promega) vector. There are multiple cloning sites in the vector. Typical cloning sites that were used are XhoI and NotI. Vector was prepared for cloning using standard molecular biology techniques. Each strand of CM and SM was chemically synthesized and annealed by heating to 100° C. and cooled to room temperature. Ligation was carried out for 3 hours using standard molecular biology techniques. Ligated plasmids were transformed into E. coli DH5a cells.

Resulting colonies were screened for presence of plasmid constructs by colony-PCR using relevant primers. Each of the plasmids (vectors) was purified from one positive colony and its sequence was verified.

Transfection of Vectors into Human HeLa Cells.

About 1.3-2×10$^6$ human HeLa cells (ATCC, Cat#CCL-2) were inoculated per 10 cm dish. Cells were then incubated in 37±1° C., 5% $CO_2$ for 24 hours. Growth medium was replaced one day post inoculation by 8 mL fresh growth medium prepared. Each cell-containing plate was transfected with one of the vectors, using Lipofectamine™ 2000 reagent (Invitrogen) as follows:

In an Eppendorf tube, 15 μL Lipofectamine™ 2000 reagent was diluted in 1000 μL DMEM medium and incubated for 5 minutes at room temperature (RT). In a second Eppendorf tube, a vector was diluted to reach a final concentration of 15 μg in 1000 μL DMEM medium. The diluted Lipofectamine™ 2000 reagent was mixed gently with the diluted DNA vector sample and incubated for 20-40 minutes at RT. Following incubation, DNA/Lipofectamine™ 2000 was added (to reach a 2000 μL final volume) to the cells. The plates were gently rocked. Plates were incubated for 5 hours at 37±1° C. and 5% $CO_2$. Following a 5-hour incubation, cells were re-plated in a 96-well plate at final concentration of 5×10$^3$ cells per well in 80 μL growth medium. 16 hours later, cells were transfected with test or control molecules using Lipofectamine™ 2000. Duplicate transfections of each siRNA concentration were performed, as described below:

Lipofectamine™ 2000 was prepared in excess to suffice for 170 wells: 85 μL of Lipofectamine™ 2000 were mixed with 3400 μL (3.4 mL) of DMEM medium and incubated for 5 minutes at RT.

Preparation of Test and Control Molecule Working Solutions:

working solutions at various concentrations was prepared by diluting a 10 μM stock solution. This dilution series was prepared for the generation of final transfection concentrations ranging between 0.0095 nM and 100 nM in 100 μL DMEM transfection medium (0.0095, 0.019, 0.039, 0.07, 0.15, 0.31, 0.625, 1.25, 2.5, 5.0, 20.0, 100.0).

100 μL aliquots of the diluted Lipofectamine 2000 were mixed gently with 100 μL of each of the diluted test molecule or control molecule working solutions (above) and mixtures were incubated for 20-40 minutes at RT. Following incubation, 20 μL of the siRNA/Lipofectamine™ 2000 mixture were added on top of the cells (pre-incubated with 80 μL of cell-culture medium above). The plates were gently rocked. Cells were incubated for 48 hours at 37±1° C. and 5% $CO_2$.

Determination of Renilla Luciferase Activity in Transfected Cells

The psiCHECK™-2 vector enables monitoring of changes in expression of a target sequence fused to the Renilla luciferase reporter gene. The test/control molecule target sequence is cloned into the 3'-untranslated region (3'-UTR) of Renilla luciferase. Measuring the decrease in Renilla luciferase activity thus provides a convenient way of monitoring activity. In addition, the psiCHECK™-2 vector contains a second reporter gene, Firefly luciferase, transcribed under a different promoter, which allows for normalization of Renilla luciferase expression.

48 Hours following test or control molecule, transfection Renilla and FireFly Luciferase activities were measured in each of the siRNA transfected samples, using Dual-Luciferase® Assay kit (Promega) according to manufacturer procedure:

Medium was completely removed from cells and cells were then lysed by the addition of 40 μL/well 1× Luciferase lysis solution. Plates were then frozen (−80° C.) and thawed at RT. Cell lysates were suspended by pipetting several times and aliquots of 12.5 μL of each sample were transferred to a separate 96-well plate. 50 μL Luciferase substrate (LARII) was added to each extract and Firefly Luciferase activity was measured by Absorbance, Fluorescence and Luminescence Reader (Perkin Elmer, Victor™ 1240). 50 μL of Stop&Glo Reagent was added to each of the samples and Renilla Luciferase activity was measured immediately. Renilla Luciferase activity value was divided by Firefly Luciferase activity value for each sample (normalization) Renilla luciferase activity is finally expressed as the percentage of the normalized activity value in tested sample relative to the normalized value obtained in cells transfected with the corresponding psiCHECK™-2 plasmid in the absence of test or control molecules.

IC50 Calculation

The IC50 values of test and control molecule activity against the GS_CM site were determined by constructing a dose-response curve using the activity results obtained with the various final siRNA concentrations. The dose response curve was constructed by plotting the relative normalized values of Renilla luciferase activity versus the logarithm of transfected siRNA concentration. The curve was calculated by fitting the best sigmoid curve to the measured data. The methods for the sigmoid fit is called 3-point curve fit.

$$Y = Bot + \frac{100 - Bot}{1 + 10^{(LogIC50 - X) \times HillSlope}}$$

Where:
Y is the residual caspase 2 mRNA response,
X is the logarithm of transfected siRNA concentration,
Bot is the Y value at the bottom plateau,
Log IC50 is the X value when Y is halfway between bottom and top plateaus and HillSlope is the steepness of the curve.

Results

For the evaluation of the potential off-target activity of each strand of a double stranded RNA molecule strands, the "guide-seed-sequence-and-passenger-strand-based activity assay" was employed using the psiCHECK (Promega) plasmid constructs. The measurement of Renilla activity provides a convenient way of monitoring double stranded RNA activity.

Measurement of Target Renilla Luciferase Protein Activity

The activity of both test and control molecules against the four target sequences (GS-CM, guide strand complete match; GS-SM, guide strand seed match; PS-CM, passenger strand complete match; and PS-SM, passenger strand seed match) was assessed at the protein level by measuring the relative activity of the Renilla luciferase reporter protein in cells transfected with various concentrations of molecule. Each assay is repeated three times. The IC50 value of test molecule activity against the GS-CM target site is determined by construction of concentration-response plots.

Both test and control molecules were active against the target GS-CM site in a dose response. Results are presented as % Luciferase activity from Ctrl (control), i.e. the lower the value the higher the activity of the double stranded compound in effecting knock-down of the target sequence.

Tables F-L below provide on target and off-target activity for some of the molecules tested. Results are shown as % residual target remaining when cells treated with dsRNA at listed concentration.

TABLE F

On-target activity and off-target activity of dsRNA molecules comprising 2'5' in antisense strand, positions, 5, 6, 7, and/or 8 (Rac1_2 dsRNA)

| | | | | siRNA structure | | | | |
|---|---|---|---|---|---|---|---|---|
| | | | 2'-5', | | 2'-5', | | 2'-5', | |
| | unmodified | 2'-5', 5 | 5&6 | 2'-5', 6 | 6&7 | 2'-5', 7 | 7&8 | 2'-5', 8 |
| | | | | name | | | | |
| siRNA Conc. | _S710 | _S1393 | _S1394 | _S1395 | _S1396 | _S1397 | _S1398 | _S1399 |
| Antisense on target (target plasmid contain RAC1_2 full sense sequence) | | | | | | | | |
| 20 nM | 5 | 4 | 2 | 1 | 3 | 0 | 10 | 10 |
| 5 nM | 13 | 32 | 9 | 6 | 12 | 1 | 20 | 33 |
| 0.5 nM | 47 | 53 | 48 | 38 | 40 | 20 | 71 | 79 |
| 0.05 nM | 73 | 87 | 86 | 73 | 77 | 52 | 113 | 93 |
| Antisense miRNA off-target (target plasmid contain RAC1_2 sense sequence position 2-8+) | | | | | | | | |
| 200 nM | 14 | 40 | 12 | 14 | 58 | 42 | 72 | 24 |
| 100 nM | 25 | 52 | 20 | 13 | 62 | 72 | 111 | 38 |
| 20 nM | 48 | 71 | 38 | 35 | 80 | 65 | 93 | 46 |
| 5 nM | | | | | 79 | 85 | 97 | 98 |
| 4 nM | 75 | 86 | 60 | 53 | | | 106 | 88 |
| 2.5 nM | | | | | 89 | 69 | 88 | 97 |
| 1.25 nM | | | | | 108 | 100 | 91 | 78 |
| 0.6 nM | | | | | 114 | 74 | 103 | 94 |
| 0.3 nM | | | | | 76 | 73 | 109 | 78 |
| 0.16 nM | | | | | 100 | 61 | 83 | 74 |
| 0.05 nM | | | | | 73 | 63 | 87 | 84 |

TABLE G1

On-target activity and off-target activity of dsRNA molecules comprising 2'5' in antisense strand, positions, 5, 6, 7, and/or 8.

Antisense on target (target plasmid contain RAC1_2 full sense sequence)

| | | | | siRNA structure | | | | |
|---|---|---|---|---|---|---|---|---|
| | | | 2'-5', | | 2'-5', | | 2'-5', | |
| | unmodified | 2'-5', 5 | 5&6 | 2'-5', 6 | 6&7 | 2'-5', 7 | 7&8 | 2'-5', 8 |
| siRNA Conc. | _S792 | _S1653 | _S1654 | _S1655 | _S1656 | _S1657 | _S1658 | _S1659 |
| 20 nM | 11 | 6 | 2 | 12 | 3 | 13 | 24 | 7 |
| 5 nM | 31 | 37 | 30 | 19 | | 53 | 56 | 61 |
| 0.5 nM | 49 | 81 | 43 | 48 | 47 | 40 | 79 | 85 |
| 0.05 nM | 72 | 96 | 63 | 52 | 65 | 53 | 87 | 87 |

Antisense miRNA off-target (target plasmid contain RAC1_2 sense sequence position 2-8)

| | | | | siRNA structure | | | | |
|---|---|---|---|---|---|---|---|---|
| | No off target | | 2'-5', | | 2'-5', | | 2'-5', | |
| | mod. | 2'-5', 5 | 5&6 | 2'-5', 6 | 6&7 | 2'-5', 7 | 7&8 | 2'-5', 8 |
| siRNA Conc. | _S792 | _S1653 | _S1654 | _S1655 | _S1656 | _S1657 | _S1658 | _S1659 |
| 200 nM | 13 | 92 | 29 | 19 | 49 | 60 | 90 | 19 |
| 100 nM | 36 | 84 | 51 | 36 | 68 | 72 | 86 | 61 |
| 20 nM | 62 | 70 | 100 | 76 | 73 | 76 | 91 | 84 |
| 4 nM | 63 | 105 | 115 | 79 | 68 | 59 | 92 | 90 |

TABLE G2

On-target activity and off-target activity of dsRNA molecules comprising L-DNA, TNA, positions, 5, 6, 7 and/or 8 or 2'OMe in antisense strand in position 2 (Rac1_2 dsRNA).
Antisense miRNA off-target
(target plasmid contain RAC1_2 sense sequence position 2-8+)

| | siRNA structure | | | | | |
|---|---|---|---|---|---|---|
| | unmodified. | L-DNA, 6 | L-DNA, 7 | L-DNA, 8 | TNA, 6 | 2'OMe, 2 |
| | | | name | | | |
| siRNA Conc. | _S710 | _S1400 | _S1401 | _S1402 | _S1403 | _S1404 |
| 20 nM | 5 | 6 | 10 | 6 | 5 | 29 |
| 5 nM | 13 | 21 | 33 | 38 | 23 | 69 |
| 0.5 nM | 47 | 54 | 61 | 60 | 64 | 109 |
| 0.05 nM | 73 | 83 | 66 | 79 | 90 | 117 |
| 200 nM | 14 | 52 | 51 | 25 | 31 | 64 |
| 100 nM | 25 | 58 | 50 | 29 | 36 | 88 |
| 20 nM | 48 | 105 | 87 | 57 | 86 | 98 |
| 5 nM | | 119 | 97 | | | |
| 4 nM | 75 | 95 | 80 | 70 | 91 | 100 |
| 2.5 nM | | 107 | 94 | | | |
| 1.25 nM | | 113 | 84 | | | |
| 0.6 nM | | 101 | 108 | | | |
| 0.3 nM | | 93 | 98 | | | |
| 0.16 nM | | 113 | 86 | | | |
| 0.05 nM | | 78 | 71 | | | |

Tables H1 and H2: On-Target and Off-Target Activity of dsRNA Molecules Comprising L-DNA, in Positions, 5, 6, 7, and/or 8 (Rac1_2 dsRNA).

H1. Antisense on target activity (target plasmid contain RAC1_2 full sense sequence)

| | siRNA structure | | | |
|---|---|---|---|---|
| | unmodified | L-DNA, 6 | L-DNA, 7 | L-DNA 8 |
| siRNA Conc. | _S792 | _S1660 | _S1661 | _S1662 |
| 20 nM | 11 | 34 | 9 | 4 |
| 5 nM | 31 | 71 | 50 | 47 |
| 0.5 nM | 49 | 74 | 88 | 79 |
| 0.05 nM | 72 | 115 | 69 | 72 |

H2. Antisense miRNA off-target (target plasmid contain RAC1_2 sense seed sequence position 2-8)

| | siRNA structure | | | |
|---|---|---|---|---|
| | No off target mod. | L-DNA, 6 | L-DNA, 7 | L-DNA, 8 |
| siRNA Conc. | _S792 | _S1660 | _S1661 | _S1662 |
| 200 nM | 13 | 90 | 19 | 58 |
| 100 nM | 36 | 86 | 61 | 65 |
| 20 nM | 62 | 91 | 84 | 79 |
| 4 nM | 63 | 92 | 90 | 76 |

Table J1 and J2: On-Target Activity and Off-Target Activity of dsRNA Molecules Comprising TNA in Position 9 of Sense Strand (Rac1_2 dsRNA).

TABLE J1

Antisense on target (target plasmid contain RAC1_2 full sense sequence)

| | siRNA structure | |
|---|---|---|
| siRNA Conc. | _S73 | _S985 (9, TNA) |
| 500 nM | 16 | 16 |
| 400 nM | 19 | 19 |
| 200 nM | 22 | 21 |
| 100 nM | 24 | 23 |

TABLE J2

Antisense miRNA off-target (target plasmid contain RAC1_2 sense sequence position 2-8+)

| | siRNA structure | |
|---|---|---|
| siRNA Conc. | S73 | S985 (9, TNA) |
| 500 nM | 78 | |
| 400 nM | 76 | |
| 200 nM | 72 | 39 |
| 100 nM | 65 | 37 |

Tables K1 and K2: Activity and or Plasma Stability Data for dsRNA Molecules Comprising 2'5' Ribonucleotides at the 3' Terminal or Penultimate Position of the Sense Strand (MYD88_11 dsRNA)

TABLE K1

| Name | Concentration | Activity % residual | Plasma stability (hrs) |
|---|---|---|---|
| MYD88_11_S1106 | 20 nM | 53 | 6 |
|  | 5 nM | 40 |  |
| MYD88_11_S1107 | 20 nM | 49 | 10 |
|  | 5 nM | 35 |  |
| MYD88_11_S1108 | 20 nM | 38 | 24 |
|  | 5 nM | 37 |  |
| MYD88_11_S1109 | 20 nM | 27 | 8 |
|  | 5 nM | 26 |  |
| MYD88_11_S1110 | 20 nM | 51 | 3 |
|  | 5 nM | 55 |  |
| MYD88_11_S1111 | 20 nM | 36 | 3 |
|  | 5 nM | 62 |  |
| MYD88_11_S1112 | 20 nM | 56 | 3 |
|  | 5 nM | 32 |  |
| MYD88_11_S1113 | 20 nM | 73 | 3 |
|  | 5 nM | 85 |  |
| MYD88_11_S1114 | 20 nM | 52 | 0 |
|  | 5 nM | 34 |  |
| MYD88_11_S1115 | 20 nM | 37 | 0.5 |
|  | 5 nM | 41 |  |

TABLE K2

| Name | Concentration (nM) | Activity (on target) | Plasma stability | Stability of sense strand vs antisense strand (as viewed by hybridization of individual strands) |
|---|---|---|---|---|
| MYD88_11_S505 | 20 | 7 | 3 |  |
|  | 5 | 8 |  |  |
| MYD88_11_S782 | 20 | 15 | 3 |  |
|  | 5 | 13 |  |  |
| MYD88_11_S1260 | 20 | 10 | 3 | Sense is stable while the AS is cleaved |
|  | 5 | 7 |  |  |
| MYD88_11_S1264 | 20 | 8 | 3 | Sense is stable while the AS is cleaved |
|  | 5 | 7 |  |  |
| MYD88_11_S1268 | 20 | 8 | 3 | Sense is stable while the As is cleaved |
|  | 5 | 7 |  |  |
| MYD88_11_S1272 | 20 | 8 | 3 | Sense is stable while the As is cleaved |
|  | 5 | 5 |  |  |
| MYD88_11_S1276 | 20 |  | 3 | Sense and AA are unstable |
|  | 5 |  |  |  |
| MYD88_11_S1301 | 20 | 7 |  |  |
|  | 5 | 7 |  |  |
| MYD88_11_S1262 | 20 |  | 24 | Sense looks unstable while AS stable |
|  | 5 |  |  |  |
| MYD88_11_S1266 | 20 |  | 24 | Both strands are stable |
|  | 5 |  |  |  |
| MYD88_11_S1270 | 20 |  | 24 | Both strands are stable |
|  | 5 |  |  |  |
| MYD88_11_S1274 | 20 |  | 24 | Both strands are stable |
|  | 5 |  |  |  |
| MYD88_11_S1325 | 20 | 5 | 24 |  |
|  | 5 | 9 |  |  |
| MYD88_11_S1326 | 20 | 3 | 24 |  |
|  | 5 | 3 |  |  |
| MYD88_11_S1327 | 20 | 11 | 24 |  |
|  | 5 | 5 |  |  |
| MYD88_11_S1328 | 20 | 6 | 24 |  |
|  | 5 | 14 |  |  |
| MYD88_11_S1329 | 20 | 10 | 24 |  |
|  | 5 | 8 |  |  |

Consecutive 2'-5' nucleotides at 3' end does not hamper activity and may even improve activity when a 3' Pi is present (i.e. _S1264). Plasma stability is improved with 4 or 5 or 6 consecutive 2'5' ribonucleotides positioned at the 3' terminal or 3' penultimate position.

Tables L1 and L2 provide knock down activity (% residual mRNA) data for double stranded molecules comprising TNA residues in the sense strand or antisense strand.

TABLE L1

| Name | TNA sense (positions 5' > 3') | TNA Antisense (positions 5' > 3') | 80 nM | 40 nM | 20 nM | 10 nM | 5 nM | 2.5 nM | 1.25 nM | 0.62 nM | 0.31 nM |
|---|---|---|---|---|---|---|---|---|---|---|---|
| P53_17_S981 | 15-19 | — | 24 | 22 | 45 | 55 | 62 | 61 | 100 | 100 | 100 |
| P53_17_S982 | 13, 15-19 | — | 26 | 14 | 28 | 59 | 58 | 80 | 91 | 79 | 100 |
| P53_17_S998 |  | — |  |  |  |  |  |  |  |  |  |
| P53_17_S980 | 2, 5, 6, 10, 12, 13, 16 18, 19 | — |  |  | 69 |  | 70 |  | 100 (1 nM) |  |  |
| MYD88_11_S1291 | 14, 16-19 | — |  |  | 11 |  | 15 |  | 24 (1 nM) |  |  |
| MYD88_11_S1292 | 13, 14, 16-19 | — |  |  | 10 |  | 12 |  | 31 (1 nM) |  |  |
| MYD88_11_S1293 | 12-14, 16-19 | — |  |  | 13 |  | 18 |  | 27 (1 nM) |  |  |
| MYD88_11_S1297 | 13, 14, 16-19 | — |  |  |  |  |  |  |  |  |  |
| MYD88_11_S889 | — | — |  |  |  |  |  |  |  |  |  |
| MYD88_11_S782 | — | — |  |  | 34 |  | 45 |  | 62 (1 nM) |  |  |
| RAC1_2_S988 (two assays) | — | 3, 4, 6, 9, 12, 13, 16, 17, 19 |  |  | 60 |  | 68 |  | 61 (1 nM) | 61 (0.5 nM) | 66 (0.05 nM) |
|  |  |  |  |  |  |  | 33 |  |  |  |  |
| RAC1_2_S987 | 2, 5, 6, 10, 12, 13, 18, 19 | — |  |  | 6 |  | 11 |  | 29 (1 nM) |  |  |
| RAC1_2_S1403 | — | 6 |  |  |  |  |  |  |  |  |  |

TABLE L1-continued

| Name | TNA sense (positions 5' > 3') | TNA Antisense (positions 5' > 3') | 80 nM | 40 nM | 20 nM | 10 nM | 5 nM | 2.5 nM | 1.25 nM | 0.62 nM | 0.31 nM |
|---|---|---|---|---|---|---|---|---|---|---|---|
| RAC1_2_S985 | — | 9 | | | | | | | | | |
| STRUC_2_S1302 | 15-19 | — | | | 2 | | 3 | | | 32 (0.5 nM) | |
| STRUC_2_S1303 | 14-19 | — | | | 2 | | 5 | | 21 (1 nM) | 35 (0.5 nM) | |
| STRUC_2_S1304 | 13-19 | — | | | 3 | | 3 | | 13 (1 nM) | 16 (0.5 nM) | |
| STRUC_2_S1305 | 12-19 | — | | | 2 | | 4 | | 14 (1 nM) | 11 (0.5 nM) | |
| STRUC_2_S1306 | 11-19 | — | | | 4 | | 5 | | 40 (1 nM) | 56 (0.5 nM) | |
| STRUC_2_S216 | — | — | | | 25 | | 12 | | 2 (1 nM) | 2 (0.5 nM) | |
| STRUC_2_S1259 | — | — | | | | | | | | | |
| STRUC_2_S1322 | — | — | | | | | | | | | |
| STRUC_2_S1315 | 15-19 | — | | | | | | | | | |
| STRUC_2_S1316 | 14-19 | — | | | | | | | | | |
| STRUC_2_S1317 | 13-19 | — | | | | | | | | | |
| STRUC_2_S1318 | 12-19 | — | | | | | | | | | |
| STRUC_2_S1319 | 11-19 | — | | | | | | | | | |

TABLE L2

| Name | TNA sense (positions 5' > 3') | TNA Antisense | 25 nM | 5 nM | 0.5 nM | 0.2 nM | 0.005 nM |
|---|---|---|---|---|---|---|---|
| MYD88_11_S1276 | — | | 52 | 52 | 57 | | 88 |
| MYD88_11_S1788 | 14, 16, 17, 18, 19 | | 17 | 12 | 18 | 67 | 75 |
| MYD88_11_S1789 | 13, 14, 16, 17, 18, 19 | | 14 | 17 | 46 | 62 | 74 |
| MYD88_11_S1790 | 12, 13, 14, 16, 17, 18, 19 | | | 18 | 20 | 77 | 85 |

Example 3. Synthesis of Compound of Formula

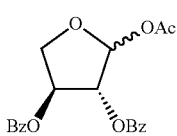

An attempt to follow the procedure described in Schöning et al., Helv. Chim. Acta 85:4111-4153 (2002) at pp. 4114-5 was made to obtain the title compound.

Example 4. Synthesis of Compound of Formula

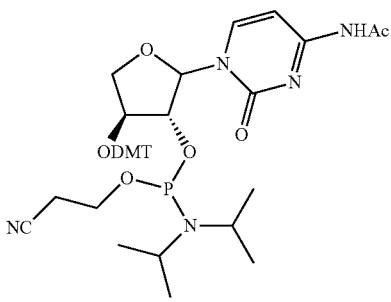

First Step: Synthesis of Compound of Formula

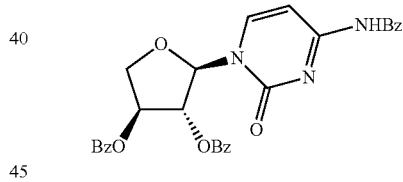

Second Step: Synthesis of Compound of Formula

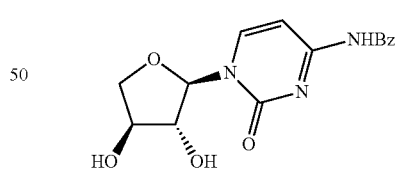

Third Step: Synthesis of Compound of Formula

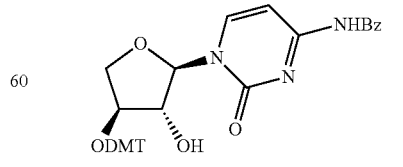

The unwanted regioisomer in which the DMT ether was at the 3- rather than the 4-position was separated from the desired regioisomer by column chromatography.

Fourth Step: Synthesis of Compound of Formula

Fifth Step: Synthesis of Compound of Formula

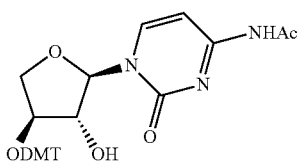

Sixth Step: Synthesis of Compound of Formula

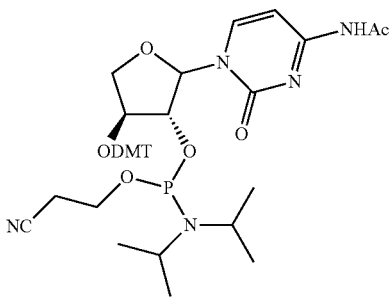

Example 5. Synthesis of Compound of Formula

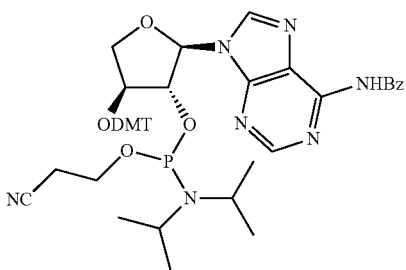

First Step: Synthesis of Compound of Formula

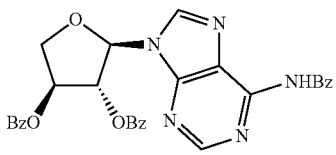

Second Step: Synthesis of Compound of Formula

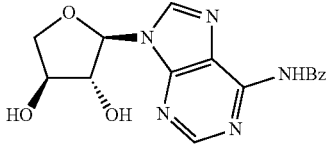

Third Step: Synthesis of a Compound of Formula

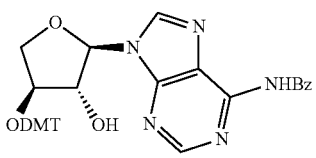

Fourth Step: Synthesis of Compound of Formula

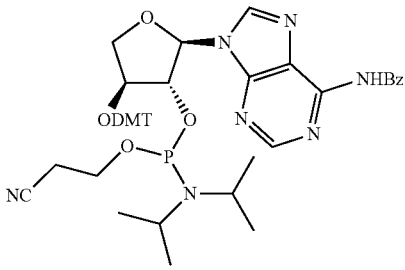

Example 6. Synthesis of dsRNA Molecules Using RNA and TNA Phosphoramidites

TNA phosphoramidites were synthesized as described herein. The synthesis of chimeric oligonucleotides including RNA and TNA phosphoramidites was carried out using established solid phase synthesis methods, with some modifications to optimize the coupling yields (Schoning et al, 2002. Helvetica Chimica ACTA 85:4111-4153).

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Using proprietary algorithms and the known sequence of a target gene, 18 and 19-mer sequences of many potential siRNAs were generated. The antisense strand sequences that were generated using this method are fully or substantially complementary to a section of target mRNA sequence. In some embodiments the antisense sequence is fully complementary to a section of the corresponding mRNA sequence. For generating some of the modified dsRNA molecules of the invention, the nucleotide at the 5' terminal position of the antisense strand (N)x (position 1; $N^1$) was substituted to generate a double stranded nucleic acid molecule of embodiments of structure A2. In other examples, the nucleotide at the 5' terminal position of the antisense strand (N)x and the nucleotide at the 3' terminal position of the sense strand (N')y were substituted to generate the double stranded nucleic acid molecule of embodiments of structure A2.

In general, the double stranded molecules having specific sequences that are selected for in vitro testing are specific for human and a second species such as rat, mouse or rabbit genes.

The exemplary compounds disclosed herein target rat TP53 human Rac1 or human MYD88 (*Homo sapiens* myeloid differentiation primary response gene (88) (MYD88), mRNA) gi|289546502|ref|NM_001172567.1| (SEQ ID NO:2) disclosed supra in Example 1. dsRNA compounds that target an artificial sequence comprising multiple A and C nucleotides were used and are known as STRUC2.

Example 7. Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine) Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

The compounds disclosed herein are tested for efficacy in treating ischemia reperfusion injury in an animal model of ischemia-reperfusion-induced ARF.

Example 8. Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleol, and heels are especially susceptible; other sites may be involved depending on the patient's situation.

The molecules disclosed herein are tested for efficacy in treating pressure sores, ulcers and similar wounds in, inter alia, the mouse model as described in Reid et al., J Surg. Res. 116:172-180, 2004 or in the rabbit model as described by Mustoe et al, JCI, 1991. 87(2):694-703; Ahn and Mustoe, Ann P1 Surg, 1991. 24(1):17-23.

Example 9. Model Systems of Chronic Obstructive Pulmonary Disease (COPD)

Chronic obstructive pulmonary disease (COPD) is characterized mainly by emphysema, which is permanent destruction of peripheral air spaces, distal to terminal bronchioles. Emphysema is also characterized by accumulation of inflammatory cells such as macrophages and neutrophils in bronchioles and alveolar structures. Emphysema and chronic bronchitis may occur as part of COPD or independently.

The molecules disclosed herein are tested for efficacy in treating COPD/emphysema/chronic bronchitis in, inter alia, animal models such as those disclosed as follows: Starcher and Williams, 1989. Lab. Animals, 23:234-240; Peng, et al., 2004.; Am J Respir Crit Care Med, 169:1245-1251; Jeyaseelan et al., 2004. Infect. Immunol, 72: 7247-56. Additional models are described in PCT patent publication WO 2006/023544 assigned to the assignee of the present application, which is hereby incorporated herein by reference.

Example 10. Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

dsRNA is injected into the spinal cord following spinal cord contusion and in uninjured rats. Sagittal cryosections are produced and immunostaining using four different groups of antibodies is performed to determine whether uptake has occurred in neurons, astroglia, oligdendroglia and/or macrophages/microglia. Markers for neurons include NeuN, or GAP43; markers for astroglia and potential neural stem cells include GFAP, nestin or vimentin; markers for oligdendroglia include NG2 or APC; markers for macrophages/microglia include ED1 or Iba-1 (Hasegawa et al., 2005. Exp Neurol 193:394-410).

Rats are injected with two different doses of dsRNA (1 μg/μl, 10 μg/μl) and are left for 1 and 3 days before sacrifice. The results indicate that dsRNA to spinal cord injury target genes increases motoneuron recovery.

Example 11. Model Systems of Glaucoma and Ischemic Optic Neuropathy (ION)

The compounds disclosed herein are tested for efficacy in treating or preventing glaucoma in the animal model, for example, as described by Pease et al., J. Glaucoma, 2006, 15(6):512-9 (Manometric calibration and comparison of TonoLab and TonoPen tonometers in rats with experimental glaucoma and in normal mice).

An animal model for Ischemic optic neuropathy was established in adults Wistar rats using a protocol of optic nerve crush injury. Seven days prior to the optic nerve crush (ONC), the retinal ganglion cells (RGC) are selectively labelled by application of the retrograde tracer FluoroGold (2%, Fluorochrome, Englewood, Colo.) to the superior colliculus. The tracer is transported by retrograde transport along RGC axons resulting in complete and specific labelling of all RGCs within 1 week post injection of the fluorescent tracer. The animals are subjected to the ONC injury 7 days post retrograde tracing. The orbital optic nerve is exposed through a supraorbital approach and all axons in the optic nerve were transected by crushing with forceps for 10 seconds, 2 mm from the lamina cribrosa. A single dose of 20 μg/5 μl of PBS of the test modified dsRNA is microinjected into the vitreous body 2 mm anterior to the nerve head, using a glass micropipette at the time of the optic nerve crush.

The survival of RGCs is determined 7 days following the optic nerve crush by counting FluoroGold-labelled RGCs on flat-mounted retinas. The experimental animals are perfused transcardially with 4% paraformaldehyde at 1 week after the optic nerve crush. Both retinas are dissected out, fixed for an additional 30 min and flat-mounted on a glass slide for ganglion cell layer quantification. The number of fluorescent RGCs is counted in 16 distinct areas in each retina and the percent of survival of the RGCs is determined compared to samples obtained from rats which did not undergo optic nerve crush injury at all or samples obtained from rats which were injected with PBS, control siRNA or GFP siRNA along with the optic nerve crush injury. Microglia cells that may have incorporated FluoroGold after phagocytosis of dying RGCs were distinguished by their characteristic morphology and excluded from quantitative analyses.

Another model of optic nerve axotomy where the entire population of RGCs are axotomized by transecting the optic nerve close to the eye is utilized. (Cheng L, et al. *J. Neurosci.* 2002; 22:3977-3986).

Example 12. Rat Model Systems of Ischemia/Reperfusion Injury Following Lung Transplantation The compounds disclosed herein are tested for efficacy in treating ischemia/reperfusion injury or hypoxic injury following lung transplantation in one or more of the experimental animal models, for example as described by Mizobuchi et al., 2004. J. Heart Lung Transplant, 23:889-93; Huang, et al., 1995. J. Heart Lung Transplant. 14: S49; Matsumura, et al., 1995. Transplantation 59: 1509-1517; Wilkes, et al., 1999. Transplantation 67:890-896; Naka, et al., 1996. Circulation Research, 79: 773-783.

Example 13. Model Systems of Acute Respiratory Distress Syndrome

The compounds disclosed herein are tested for efficacy in treating acute respiratory distress syndrome in inter alia in the animal model described by Chen et al (J Biomed Sci. 2003; 10 (6 Pt 1):588-92.

Example 14. Model Systems of Hearing Loss Conditions

Representative models for hearing loss include the Chinchilla model of carboplatin-induced or cisplatin-induced cochlea hair cell death and Chinchilla model of acoustic-induced cochlea hair cell death A method of treating Ménière's disease is tested in the Phex genetic mouse model (Megerian et al ("A mouse model with postnatal endolymphatic hydrops and hearing loss", Hearing Res 2008; 237(1-2):90-105).

Example 15. Animal Models of Osteoarthritis (OA)

Collagen induced arthritis (CIA): CIA in mice is described in Trentham et al. (1977. J. Exp. Med. 146: 857-868). Adjuvant-induced arthritis (AA):AA is described in Kong et al., (1999. Nature, 402:304-308). A menisectomy model is described in Han et al., (1999. Nagoya J Med Sci 62(3-4):115-26).

The effect of different dsRNA, on different parameters related to OA such as chondrocyte proliferation, terminal differentiation and development of arthritis, is evaluated using one or more of the above models, in addition to in vitro models known in the art.

Example 16. Rat Model Systems for Transplantation-Associated Acute Kidney Injury Cold Ischemia—

A left nephrectomy is performed on a donor animal, followed by a cold preservation (on ice) of the harvested kidney for a period of 5 hours. At the end of this period, the recipient rat will undergo a bilateral nephrectomy, followed by transplantation of the cold-preserved kidney graft. The total warm ischemia time (including surgical procedure) is about 30 minutes. Chemically modified siRNA is administered intravenously via the femoral vein, either to the donor animal prior to the kidney harvest ("pre"), or to the recipient animal 15 minutes ("post 15 min") or 4 hours (post 4 hrs) post-transplantation.

Warm Ischemia—

In test rats a left nephrectomy is performed, followed by auto transplantation that results in a warm kidney graft preservation period of 45 minutes. Following auto transplantation, a right nephrectomy is performed on the same animal. Chemically modified siRNA to a target is administered intravenously via the femoral vein either before harvesting of the kidney graft (mimicking donor treatment) ("pre"), or after the kidney autotransplantation (mimicking recipient treatment), or both before harvest and after transplantation (combined donor and recipient treatment) ("pre-post").

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

The invention claimed is:

1. A double stranded nucleic acid molecule having structure A1 set forth below:

(A1) 5' (N)x-Z 3' (antisense strand)
     3' Z'-(N')y z" 5' (sense strand)

wherein said double stranded nucleic acid molecule is an siRNA, siNA, or miRNA, and wherein each of N and N' is a ribonucleotide that may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present independently includes 1-5 consecutive nucleotides or non-nucleotide moieties or a combination thereof covalently attached at the 3' terminus of the strand in which it is present;

wherein z" may be present or absent, but if present is a capping moiety covalently attached at the 5' terminus of (N')y;

wherein each of x and y is independently an integer between 18 and 25;

wherein the sequence of (N')y has complementarity to the sequence of (N)x, and (N)x comprises an antisense sequence complementary to a consecutive sequence in a target RNA; and wherein the molecule comprises the following modification b and at least one of the following modifications a and c:

a. a 2'5' nucleotide or a mirror nucleotide is present in (N)x in at least one of positions 5, 6, 7, 8, or 9 from the 5' terminus;
 b. a threose nucleic acid moiety is present in the sense strand at positions 14 and 16-19, positions 13-14 and 16-19, or positions 12-14 and 16-19, and a 2'5' nucleotide is present in the same sense strand; and
 c. from 1 to 10 2'5' nucleotides are present in (N')y at the 3' terminal or penultimate positions, wherein the threose nucleic acid is an L-alpha-threofuranosyl nucleotide.

2. The double stranded nucleic acid molecule of claim 1, wherein x=y and each of x and y is 19, 20, 21, 22 or 23.

3. The double stranded nucleic acid molecule of claim 2, wherein x=y=19.

4. The double stranded nucleic acid molecule of claim 1, wherein the covalent bond joining each consecutive N or N' is a phosphodiester bond.

5. The double stranded nucleic acid molecule of claim 1, wherein the sequence of (N')y is fully complementary to the sequence of (N)x.

6. The double stranded nucleic acid molecule of claim 1, wherein the double stranded nucleic acid molecule comprises a mismatch to the target mRNA at the 5' terminal ribonucleotide of the antisense strand.

7. The double stranded nucleic acid molecule of claim 1, wherein a 2'5' nucleotide or a mirror nucleotide is present in at least one of positions 5, 6, 7, 8, or 9 from the 5' terminus of the antisense strand.

8. The double stranded nucleic acid molecule of claim 7, wherein the antisense strand comprises a 2'-5' nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9, or in positions 5-9.

9. The double stranded nucleic acid molecule of claim 8, wherein the antisense strand comprises a 2'-5' nucleotide in position 5, in position 6, in position 7, or in position 8.

10. The double stranded nucleic acid molecule of claim 7, wherein the antisense strand comprises a mirror nucleotide in position 5, in position 6, in position 7, in position 8, in position 9, in positions 5-6, in positions 6-7, in positions 7-8, in positions 8-9, in positions 5-7, in positions 6-8, in positions 7-9, in positions 5-8, in positions 6-9, or in positions 5-9.

11. The double stranded nucleic acid molecule of claim 10, wherein the antisense strand comprises a mirror nucleotide in position 5, in position 6, in position 7, or in position 8.

12. The double stranded nucleic acid molecule of claim 1, wherein the sense strand comprises at least four consecutive 2'5' nucleotides at the 3' terminal or penultimate position.

13. The double stranded nucleic acid molecule of claim 12, wherein the sense strand comprises 2'5' nucleotides in positions 15, 16, 17, and 18, or in positions 16, 17, 18, and 19.

14. The double stranded nucleic acid molecule of claim 1, further comprising at least one 2'OMe sugar modified ribonucleotide in the antisense strand.

15. The double stranded nucleic acid molecule of claim 1, further comprising at least one 2'OMe sugar modified ribonucleotide in the sense strand.

16. The double stranded nucleic acid molecule of claim 14, wherein the 2'OMe sugar modified ribonucleotides are present in positions 2, 4, and 6 from the 5' terminus of the antisense strand.

17. The double stranded nucleic acid molecule of claim 1, comprising z" covalently attached at the 5' terminus of the sense strand.

18. The double stranded nucleic acid molecule of claim 17, wherein z" is an abasic moiety.

19. The double stranded nucleic acid molecule of claim 1, comprising Z covalently attached to the 3' terminus of the antisense strand or Z' covalently attached to the 3' terminus of the sense strand, or both Z covalently attached to the 3' terminus of the antisense strand and Z' covalently attached to the 3' terminus of the sense strand.

20. The double stranded nucleic acid molecule of claim 19, wherein Z and Z' independently comprise one or two non-nucleotide moieties.

21. The double stranded nucleic acid molecule of claim 20, wherein Z and Z' independently comprise C3PiC3Pi or C3PiC3OH moieties.

22. The double stranded nucleic acid molecule of claim 1, wherein the target RNA comprises human mRNA or viral RNA.

23. A composition comprising the double stranded nucleic acid molecule of claim 1 and a pharmaceutically acceptable carrier.

* * * * *

UNITED STATES PATENT AND TRADEMARK OFFICE
CERTIFICATE OF CORRECTION

PATENT NO. : 10,144,928 B2
APPLICATION NO. : 14/996493
DATED : December 4, 2018
INVENTOR(S) : Sharon Avkin-Nachum et al.

Page 1 of 1

It is certified that error appears in the above-identified patent and that said Letters Patent is hereby corrected as shown below:

On the Title Page

First column, (63) Related U.S. Application Data, Line 2, after "now abandoned" insert --, filed as application No. PCT/US2011/063365 on Dec. 6, 2011. Provisional application no. 61/419,910, filed on Dec. 6, 2010, and provisional application no. 61/419,918, filed on Dec. 6, 2010.--.

In the Specification

Column 69
After header "TABLE C1," Line 2, delete "09-mer strand" and insert --19-mer strand--.

Column 71
After header "TABLE C1-continued," Line 2, delete "09-mer strand" and insert --19-mer strand--.

Signed and Sealed this
Thirtieth Day of April, 2019

Andrei Iancu
*Director of the United States Patent and Trademark Office*

SEQUENCE LISTING

<160> NUMBER OF SEQ ID NOS: 231

<210> SEQ ID NO 1
<211> LENGTH: 2341
<212> TYPE: RNA

<213> ORGANISM: Homo sapiens

<400> SEQUENCE: 1

| | | | | | |
|---|---|---|---|---|---|
| gggaggccgg | augugagugg | agcggccauu | uccuguuucu | cugcaguuuu | ccucagcuuu | 60 |
| ggguggtggc | cgcugccggg | caucggcuuc | caguccgcgg | agggcgaggc | ggcguggaca | 120 |
| gcggccccgg | cacccagcgc | cccgccgccc | gcaagccgcg | cgcccguccg | ccgcgccccg | 180 |
| agcccgccgc | uuccuaucuc | agcgcccugc | cgccgccgcc | gcggcccagc | gagcggcccu | 240 |
| gaugcaggcc | aucaagugug | uggugguggg | agacggagcu | guagguaaaa | cuugccuacu | 300 |
| gaucaguuac | acaaccaaug | cauuuccugg | agaauauauc | ccacugucu | uugacaauua | 360 |
| uucugccaau | guuaugguag | auggaaaacc | ggugaaucug | ggcuuauggg | auacagcugg | 420 |
| acaagaagau | uaugcagau | uacgcccccu | auccauccg | caaacagaug | uguucuaaau | 480 |
| uugcuuuucc | cuugugaguc | cugcaucauu | ugaaaaugc | cgugcaaagu | gguauccuga | 540 |
| ggugcggcac | cacugucca | acacucccau | cauccuagug | gaacuaaac | uugaucuuag | 600 |
| ggaugauaaa | gacacgaucg | agaaacugaa | ggagaagaag | cugacuccca | ucaccuaucc | 660 |
| gcagggucua | gccauggcua | aggagauugg | ugcuguaaaa | uaccggagu | gcucggcgcu | 720 |
| cacacagcga | ggcucaaga | caguguuuga | cgaagcgauc | cgagcaguc | cucgcccgcc | 780 |
| ucccgugaag | aagaggaaga | gaaaaugccu | gcuguugaa | augcucagc | cccucguucu | 840 |
| uggccugc | ccuggaacc | uuuguacgcu | ugcucaaaa | aaaaacaaaa | aaaaaaaca | 900 |
| aaaaaaaaa | acaacggugg | agccuucgca | cucaaugcca | acuuuuguu | acagauuaau | 960 |
| uuuuccauaa | aaccauuuuu | ugaaccaauc | aguaauuuua | agguuuguu | uguucuaaau | 1020 |
| guaagaguuc | agacucacau | ucuauuaaaa | uuuagcccua | aaaugacaag | ccuucuaaaa | 1080 |
| gccuuauuu | ucaaaagcgc | ccccccauu | cuuguucaga | uuaagaguug | ccaaauacc | 1140 |
| uucugaacua | cacugcauug | uguguccgag | aacaccgagc | acugaacuuu | gcaaagaccu | 1200 |
| ucgucuuuga | gaagacggua | gcuucugcag | uuaggaggug | cagacacuug | cucuccuaug | 1260 |
| uaguucucag | augcguaaag | cagaacagcc | ucccgaauga | agcguugcca | uugaacucac | 1320 |
| cagugaguua | gcagcacgug | uucccgacau | aacauuguac | uguaauggag | ugagcguagc | 1380 |
| agcucagcuc | uuuggaucag | ucuuugugau | uucauagcga | guuucugac | cagcuuuugc | 1440 |
| ggagauuuug | aacagaacug | cuauuuccuc | uaaugaagaa | uucuguuuag | cgugggugu | 1500 |
| gccgggtggg | guguguguga | ucaaaggaca | aagacaguau | uuugacaaaa | uacgaagugg | 1560 |
| agauuuacac | uacauuguac | aaggaaugaa | agugucacgg | guaaaaacuc | uaaaagguua | 1620 |
| auuucuguca | aaugcaguag | augaugaaag | aaaggguuggu | auuaucagga | aauguuuucu | 1680 |
| uaagcuuuuc | cuuucucuua | caccugccau | gccuccccaa | auugggcauu | uaauucaucu | 1740 |
| uuaaacuggu | uguucuguua | gucgcuaacu | aguaaguugc | uuucuuaua | gaaccccuuc | 1800 |
| ugacugagca | auaugccucc | uuguauuaua | aaaucuuucu | gauaaugcau | uagaagguuu | 1860 |
| uuuugucgau | uaguaaaagu | gcuuccaug | uuacuuuauu | cagagcuaau | aagugcuuuc | 1920 |
| cuuaguuuuc | uaguaacuag | guguaaaaau | caugucugc | agcuuuauag | uuuuaaaau | 1980 |
| auuuuagaua | auucuaaac | uaugaaccuu | cuuaacauca | cugucuugcc | agauuaccga | 2040 |
| cacugucacu | ugaccaauac | ugacccucuu | uaccucgccc | acgcggacac | acgccuccug | 2100 |
| uagucgcuuu | gccauugau | guccuuuugg | gucugugagg | uucuguaaac | ugugcuagug | 2160 |
| cugacgaugu | ucuguacaac | uuaacucacu | ggcgagaaua | cagcguggga | cccuucagcc | 2220 |
| acuacaacag | aauuuuuuaa | auugacaguu | gcagaauugu | ggagugutuuu | uacauugauc | 2280 |

-continued

| | |
|---|---|
| uuuugcuaau gcaauuagca uuauguuuug cauguaugac uuaauaaauc cuugaaucau | 2340 |
| a | 2341 |

<210> SEQ ID NO 2
<211> LENGTH: 2886
<212> TYPE: RNA
<213> ORGANISM: Homo sapiens

<400> SEQUENCE: 2

| | |
|---|---|
| agauuccuac uucuuacgcc ccccacauca cccgccucga gaccucaagg guagaggugg | 60 |
| gcaccccgc cuccgcacuu uugcucgggg cuccagauug uagggcaggg cggcgcuucu | 120 |
| cggaaagcga aagccggcgg ggcggggcgg gugccgcagg agaaagagga agcgcuggca | 180 |
| gacaaugcga cccgaccgcg cugaggcucc aggaccgccc gccauggcug caggaggucc | 240 |
| cggcgcgggg ucugcggccc cggucuccuc cacauccucc cuuccccugg cugcucucaa | 300 |
| caugcgagug cggcgccgcc ugucucuguu cuugaacgug cggacacagg uggcggccga | 360 |
| cuggaccgcg cuggcggagg agauggacuu ugaguacuug gagauccggc aacuggagac | 420 |
| acaagcggac cccacuggca ggcugcugga cgccuggcag ggacgcccug cgcccucugu | 480 |
| aggccgacug cucgagcugc uuaccaagcu gggccgcgac gacgugcugc uggagcuggg | 540 |
| acccagcauu gaggaggauu gccaaaagua uaucuugaag cagcagcagg aggaggcuga | 600 |
| gaagccuuua cagguggccg cuguagacag cagugucccca cggacagcag agcuggcggg | 660 |
| caucaccaca cuugaugacc cccuggggca uaugccugag cguuucgaug ccuucaucug | 720 |
| cuauugcccc agcgacaucc aguuugugca ggagaugauc cggcaacugg aacagacaaa | 780 |
| cuaucgacug aaguugugug ugucugaccg cgauguccug ccuggcaccu gugucugguc | 840 |
| uauugcuagu gagcucaucg aaaagaggu ggcuagaagg ccacggggug ggugccgccg | 900 |
| gauggugug guugcucug augauuaccu gcagagcaag gaaugugacu ccagaccaa | 960 |
| auuugcacuc agccucucuc caggugccca ucagaagcga cugauccca ucaaguacaa | 1020 |
| ggcaaugaag aaagaguucc ccagcauccu gagguucauc acugucugcg acuacaccaa | 1080 |
| ccccugcacc aaaucuuggu ucuggacucg ccuugccaag gccuugucccc ugcccugaag | 1140 |
| acuguucuga ggcccugggu gugugugua cugucugccu guccauguac uucugcccug | 1200 |
| ccuccuccuu ucguuguagg aggaaucugu gcucuacuua ccucucaauu ccuggagaug | 1260 |
| ccaacuucac agacacgucu gcagcagcug gacaucacau ucauguccu gcauggaacc | 1320 |
| aguggcugug aguggcaugu ccacuugcug gauuacagc caggacacua agaacagga | 1380 |
| ccagcugaga cuaagaagga ccagcagagc cagcucagcu cugagccauu cacacaucuu | 1440 |
| caccucagu uucccacuu gaggaguggg auggggagaa cagagaguag cuguguuuga | 1500 |
| auccuguag gaauggguga agcauagcuc ugggucuccu ggggagacc aggcuuggcu | 1560 |
| gcgggagagc uggcuguugc uggacuacau gcuggcacu gcugugacca cgacacugcu | 1620 |
| ggggcagcuu cuuccacagu gaugccuacu gaugcuucag ugccucugca caccgcccau | 1680 |
| uccacuuccu ccuucccac agggcaggug gggaagcagu uuggcccagc ccaaggagac | 1740 |
| cccaccuuga gccuuauuuc cuaaugggu caccucuca cugcaucuuu cacaccccc | 1800 |
| agcuucugcc caaccuucag cagugacaag ucccaagag acugccuga gcagcuuggg | 1860 |
| cugcuuuuca uuccaccug ucaggaugcc uguggucaug cucucagcuc caccuggcau | 1920 |
| gagaagggau ccuggccucu ggcauauuca ucaaguauga guucugggga ugagucacug | 1980 |

| | |
|---|---|
| uaaugaugug agcagggagc cuuccucccu gggccaccug cagagagcuu ucccaccaac | 2040 |
| uuuguaccuu gauugccuua caaaguuauu uguuuacaaa cagcgaccau auaaaagccu | 2100 |
| ccugccccaa agcuuguggg cacaugggca cauacagacu cacauacaga cacacacaua | 2160 |
| uauguacaga caugacucu cacacacaca ggcaccagca uacacacguu uuucuaggua | 2220 |
| cagcucccag gaacagcuag gugggaaagu cccaucacug agggagccua accaugcccc | 2280 |
| ugaacaaaaa uugggcacuc aucuauuccu uuucucuugu ucccuacuc auugaaacca | 2340 |
| aacucuggaa aggacccaau guaccaguau uuauaccucu aaugaagcac agagagagga | 2400 |
| agagagcugc uuaaacucac acaacaauga acugcagaca cagcguuucu cucccucucu | 2460 |
| ccuucccaga gcaauuuaua cuuuacccuc aggcuguccu cugggagaa ggugccaugg | 2520 |
| ucuuaggugu cugugcccca ggacagaccc uaggacccua aauccaauag aaaaugcaua | 2580 |
| ucuuugcucc acuuucagcc aggcuggagc aagguaccuu uucuuaggau cuuggagggg | 2640 |
| aauggaugcc ccucucugca ugaucuuguu gaggcauuua gcugccaugc accugucccc | 2700 |
| cuuuaauacu gggcauuuua aagccaucuc aagaggcauc uucuacaugu uuguacgca | 2760 |
| uuaaaauaau ucaaagaua ucgagaaaa gccgauauuu gccauucuuc cuauauccug | 2820 |
| gaauauaucu ugcauccuga guuuauaaua auaaauaaua uucuaccuug gaaaaaaaaa | 2880 |
| aaaaaa | 2886 |

<210> SEQ ID NO 3
<211> LENGTH: 1792
<212> TYPE: RNA
<213> ORGANISM: Rattus norvegicus

<400> SEQUENCE: 3

| | |
|---|---|
| ucugaagcuc caguucauug ggacuuaucc uugcuauagg uagcgacuac aguuagggg | 60 |
| uaccuggcau ccgggcccgc acccuacuuc ccagcagggu gucacgcucc ccugaagacu | 120 |
| ggauaacugu caugaggau ucacagucgg auaugagcau cgagcucccu cugagucagg | 180 |
| agacauuuuc augcuuaugg aaacuucuuc cuccagauga uauucugccc accacagcga | 240 |
| cagggucacc uaauuccaug gaagaucugu uccugcccca ggauguugca gaguuguuag | 300 |
| aaggcccaga ggaagcccuc caagugucag cuccugcagc acaggaaccu ggaacugagg | 360 |
| ccccugcacc cguggcccu gcuucagcua caccgguggcc ucugucaucu uccgucccuu | 420 |
| cucaaaaaac uuaccaaggc aacuauggcu uccaccuggg cuuccugcag ucaggggacag | 480 |
| ccaagucugu uaugugcacg uacucaauuu cccucaauaa gcuguucugc cagcuggcga | 540 |
| agacaugccc ugugcaguug ugggucaccu ccacaccucc accugguacc cguguccgug | 600 |
| ccauggccau cuacaagaag ucacaacaca ugacugaggu cgugagacgc ugcccccacc | 660 |
| augagcguug cucugauggu gacggccugg cuccucccca acaucuuauc cggguggaag | 720 |
| gaaauccgua ugcugaguau cuggacgaca ggcagacuuu ucggcacagc gugguggauac | 780 |
| cguaugagcc accugaggu ggcucgacu auaccacuau ccacuacaag uacaugugca | 840 |
| acagcuccug caugggggc augaaccgcc ggcccauccu uaccaucauc acgcuggaag | 900 |
| acuccagugg gaaucuucug gacgggaca gcuugagggu ucguuuugu gccuguccug | 960 |
| ggagagaccg ucggacagag gaagaaaauu uccgcaaaaa agaagagcau ugcccggagc | 1020 |
| ugccccaggg gagugcaaag agagcacugc ccaccagcac aagcccucu ccccagcaaa | 1080 |
| agaaaaaacc acucgaugga gaauauuuca ccccuuaagau ccgugggcgu gagcgcuucg | 1140 |
| agauguuccg agagcugaau gaggccuugg aauuaaagga ugcccgugcu gccgaggagu | 1200 |

| | | |
|---|---|---|
| caggagacag cagggcucac uccagcuacc cgaagaccaa gaagggccag ucuacguccc | 1260 | |
| gccauaaaaa accaaugauc aagaaagugg ggccugacuc agacugacag ccucugcauc | 1320 | |
| cgucccccau caccagccuc cccgucccu ccuuucuugc cauuuauga cuuuagggcu | 1380 | |
| uguuaugaga gcugacaaga caaugcuagu cccuucacug ccuuuuuua ccuuguagau | 1440 | |
| aguacucggc ccccucuaug caaacugguu ccuggcccag auuggggaau ggguugguag | 1500 | |
| uugcuggguc ucgcugguc cagcgaaauc cuauccgguc aguuguugga ccuggcaccu | 1560 | |
| acagugaaau uucaccccac cccaccgccu guaagauucu aucuugggcc cucauacgau | 1620 | |
| cuguauccuc caggacccau uuccuccacu cugcaaagcc ugucgcauu uauccauccc | 1680 | |
| ccacccucu cccucuuuuu aucucuuuuu auauaucaau uucuuauuuu acaauaaacu | 1740 | |
| uuuguuacca cuuguaaaaa aaaaaaaaaa aaaaaaaaaa aaaaaaaaaa aa | 1792 | |

<210> SEQ ID NO 4
<211> LENGTH: 19
<212> TYPE: RNA
<213> ORGANISM: Artificial Sequence
<220> FEATURE:
<223> OTHER INFORMATION: Chemically synthesized

<400> SEQUENCE: 4
gaguccugca ucauuugaa                                              19

<210> SEQ ID NO 5
<211> LENGTH: 19
<212> TYPE: RNA
<213> ORGANISM: Artificial Sequence
<220> FEATURE:
<223> OTHER INFORMATION: Chemically synthesied

<400> SEQUENCE: 5
uucaaaugau gcaggacuc                                              19

<210> SEQ ID NO 6
<211> LENGTH: 19
<212> TYPE: RNA
<213> ORGANISM: Artificial Sequence
<220> FEATURE:
<223> OTHER INFORMATION: Chemically synthesized

<400> SEQUENCE: 6
gaaugugacu uccagacca                                              19

<210> SEQ ID NO 7
<211> LENGTH: 19
<212> TYPE: RNA
<213> ORGANISM: Artificial Sequence
<220> FEATURE:
<223> OTHER INFORMATION: Chemically synthesized

<400> SEQUENCE: 7
uggucuggaa gucacauuc                                              19

<210> SEQ ID NO 8
<211> LENGTH: 19
<212> TYPE: RNA
<213> ORGANISM: Artificial Sequence
<220> FEATURE:
<223> OTHER INFORMATION: Chemically synthesized

<400> SEQUENCE: 8
gaagaaaauu uccgcaaaa                                             19

<210> SEQ ID NO 9
<211> LENGTH: 19
<212> TYPE: RNA
<213> ORGANISM: Artificial Sequence
<220> FEATURE:
<223> OTHER INFORMATION: Chemically synthesized

<400> SEQUENCE: 9
uuuugcggaa auuuucuuc                                             19

<210> SEQ ID NO 10
<211> LENGTH: 19
<212> TYPE: RNA
<213> ORGANISM: Artificial Sequence
<220> FEATURE:
<223> OTHER INFORMATION: Chemically synthesized

<400> SEQUENCE: 10
agggcgucau ccaacacaa                                             19

<210> SEQ ID NO 11
<211> LENGTH: 19
<212> TYPE: RNA
<213> ORGANISM: Artificial Sequence
<220> FEATURE:
<223> OTHER INFORMATION: Chemically synthesized

<400> SEQUENCE: 11
uuguguugga ugacgcccu                                             19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
gaguccugca ucauuugaa                                             19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gaguccugca ucauuugaa                                             19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaguccugca ucauuugaa                                             19

<210> SEQ ID NO 15

```
<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gaguccugca ucauuugaa                                                  19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gaguccugca ucauuugaa                                                  19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gaguccugca ucauuugaa                                                  19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gaguccugca ucauuugaa                                                  19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaguccugca ucauuugaa                                                  19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gaguccugca ucauuugaa                                                  19

<210> SEQ ID NO 21
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gaguccugca ucauuugaa                                               19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gaguccugca ucauuugaa                                               19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
gaguccugca ucauuugaa                                               19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gaguccugca ucauuugaa                                               19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gaguccugca ucauuugaa                                               19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gaguccugca ucauuugaa                                               19

<210> SEQ ID NO 27
<211> LENGTH: 19
<212> TYPE: RNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 27
gaguccugca ucauuugaa                                               19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
gaguccugca ucauuugaa                                               19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gaguccugca ucauuugaa                                               19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gaguccugca ucauuugaa                                               19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gaguccugca ucauuugaa                                               19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gaguccugca ucauuugaa                                               19

<210> SEQ ID NO 33
<211> LENGTH: 19
<212> TYPE: RNA
<213> ORGANISM: Artificial Sequence -continued
<220> FEATURE:
<223> OTHER INFORMATION: Description of Artificial Sequence: Synthetic
      oligonucleotide

<400> SEQUENCE: 33
gaguccugca ucauuugaa                                              19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
gaguccugca ucatttgaa                                              19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gaguccugca ucatttgaa                                              19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
gaguccugca ucatttgaa                                              19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
gaguccugca ucatttgaa                                              19

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide

<400> SEQUENCE: 38
gaguccugca ucattgaa                                                 18

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
gaguccugca ucatttgaa                                                19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
gaguccugca ucatttgaa                                                19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gaguccugca ucatttgaa                                                19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
gaguccugca ucatttgaa                                                19

<210> SEQ ID NO 43
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
gaguccugca ucatttgaa                                              19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaguccugca ucauuugaa                                              19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gaguccugca ucauuugaa                                              19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gaguccugca ucauuugaa                                              19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
gaguccugca ucatttgaa                                              19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gaguccugca ucauuugaa                                              19
```

-continued

```
<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gaguccugca ucauuugaa                                                19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
gaguccugca ucauuugaa                                                19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gaguccugca ucauuugaa                                                19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gaguccugca ucauuugaa                                                19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gaguccugca ucauuugaa                                                19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gaguccugca ucauuugaa                                                19
```

```
<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gaguccugca ucauuugaa                                                    19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gaguccugca ucauuugaa                                                    19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gaguccugca ucauuugaa                                                    19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gaguccugca ucauuugaa                                                    19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uucaaaugau gcaggacuc                                                    19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uucaaaugau gcaggacuc                                                    19
```

```
<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uucaaaugau gcaggacuc                                                       19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uucaaaugau gcaggacuc                                                       19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uucaaaugau gcaggacuc                                                       19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uucaaaugau gcaggacuc                                                       19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uucaaaugau gcaggacuc                                                       19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uucaaaugau gcaggacuc                                                       19
```

```
<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uucaaaugau gcaggacuc                                                  19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
uucaaatgau gcaggacuc                                                  19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uucaaaugau gcaggacuc                                                  19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
uucaaaugau gcaggacuc                                                  19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uucaaaugau gcaggacuc                                                  19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 72
uucaaaugau gcaggacuc                                              19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uucaaaugau gcaggacuc                                              19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uucaaaugau gcaggacuc                                              19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uucaaaugau gcaggacuc                                              19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uucaaaugau gcaggacuc                                              19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uucaaaugau gcaggacuc                                              19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
```
uucaaaugau gcaggacuc                                            19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
uucaaatgau gcaggacuc                                            19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uucaaaugau gcaggacuc                                            19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uucaaaugau gcaggacuc                                            19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uucaaaugau gcaggacuc                                            19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uucaaaugau gcaggacuc                                            19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 84
uucaaaugau gcaggacuc                                                 19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uucaaaugau gcaggacuc                                                 19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uucaaaugau gcaggacuc                                                 19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uucaaaugau gcaggacuc                                                 19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uucaaaugau gcaggacuc                                                 19

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
uucaaatgau gcaggacuc                                                 19

<210> SEQ ID NO 90
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 90
uucaaaugau gcaggacuc                                                    19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uucaaaugau gcaggacuc                                                    19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uucaaaugau gcaggacuc                                                    19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uucaaaugau gcaggacuc                                                    19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uucaaaugau gcaggacuc                                                    19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
uucaaaugau gcaggacuc                                                    19

<210> SEQ ID NO 96
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
uucaaaugau gcaggacuc                                                      19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uucaaaugau gcaggacuc                                                      19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uucaaaugau gcaggacuc                                                      19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uucaaaugau gcaggacuc                                                      19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uucaaaugau gcaggacuc                                                      19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uucaaaugau gcaggacuc                                                      19

<210> SEQ ID NO 102
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uucaaaugau gcaggacuc                                                     19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uucaaaugau gcaggacuc                                                     19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uucaaaugau gcaggacuc                                                     19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uucaaaugau gcaggacuc                                                     19

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
bgaaugugac uuccagacca                                                    20

<210> SEQ ID NO 107
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
bgaaugugac uuccagacca                                                    20

<210> SEQ ID NO 108
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
bgaaugugac uuccagacca                                                    20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
bgaaugugac uuccagacca                                                    20

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
bgaaugugac uuccagacca                                                    20

<210> SEQ ID NO 111
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
bgaaugugac uuccagacca                                                    20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
bgaaugugac uuccagacca                                                    20

<210> SEQ ID NO 113
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
bgaaugugac uuccagacca                                                    20

<210> SEQ ID NO 114
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 114
bgaaugugac uuccagacca                                                     20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
bgaaugugac uuccagacca                                                     20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
bgaatgtgac ttccagacca                                                     20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
bgaatgtgac ttccagacca                                                     20

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
bgaaugugac uuccagacca                                                     20

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gaaugugacu uccagacca                                                      19
```

```
<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
gaaugugacu uccagacca                                                   19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gaaugugacu uccagacca                                                   19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gaaugugacu uccagacca                                                   19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gaaugugacu uccagacca                                                   19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gaaugugacu uccagacca                                                   19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gaaugugacu uccagacca                                                   19
```

```
<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gaaugugacu uccagacca                                                      19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gaaugugacu uccagacca                                                      19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
gaaugugacu uccagacca                                                      19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
gaaugugacu uccagacca                                                      19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
gaaugugacu uccagacca                                                      19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
gaaugugacu uccagacca                                                      19
```

```
<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
gaaugugacu uccagacca                                                    19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
gaaugugacu uccagacca                                                    19

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
bgaaugugac uuccagacca                                                   20

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gaaugugacu uccagacca                                                    19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
gaaugugacu uccagacca                                                    19

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 137
gaaugugacu uccagacca                                                      19

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
gaaugugacu uccagacca                                                      19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gaaugugacu uccagacca                                                      19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gaaugugacu uccagacca                                                      19

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
gaaugugacu uccagacca                                                      19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
```
gaaugugacu uccagacca                                          19

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
gaaugugacu uccagacca                                          19

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
uggtctggaa gtcacautct ttt                                     23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
uggucuggaa gucacauuct ttt                                     23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
uggtctggaa gtcacautct ttt                                     23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
uggucuggaa gucacauuct ttt                                             23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
uggtctggaa gtcacautct ttt                                             23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
uggucuggaa gucacauuct ttt                                             23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
uggtctggaa gtcacautct ttt                                             23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
uggucuggaa gucacauuct ttt                                             23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
uggtctggaa gtcacautct ttt					23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
uggucuggaa gucacauuct ttt					23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
uggtctggaa gtcacautct ttt					23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
uggucuggaa gucacauuct ttt					23

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uggucuggaa gucacauuc					19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uggucuggaa gucacauuc					19

```
<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uggucuggaa gucacauuc                                                 19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uggucuggaa gucacauuc                                                 19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
uggucuggaa gucacauuc                                                 19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uggucuggaa gucacauuc                                                 19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uggucuggaa gucacauuc                                                 19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uggucuggaa gucacauuc                                                 19

<210> SEQ ID NO 164
```

-continued

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
uggucuggaa gucacauuc                                                19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uggucuggaa gucacauuc                                                19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
uggucuggaa gucacauuc                                                19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uggucuggaa gucacauuc                                                19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
uggucuggaa gucacauuc                                                19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uggucuggaa gucacauuc                                                19

<210> SEQ ID NO 170
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uggucuggaa gucacauuc                                                    19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uggucuggaa gucacauuc                                                    19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uggucuggaa gucacauuc                                                    19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uggucuggaa gucacauuc                                                    19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uggucuggaa gucacauuc                                                    19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uggucuggaa gucacauuc                                                    19

<210> SEQ ID NO 176
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
uggucuggaa gucacauuct ttt                                          23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
uggucuggaa gucacauuct ttt                                          23

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
uggucuggaa gucacauuc                                               19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uggucuggaa gucacauuc                                               19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
uggucuggaa gucacauuc                                               19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uggucuggaa gucacauuc                                               19
```

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
gaagaaaauu uccgcaaaa                                                19

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
gaagaaaauu uccgcaaaa                                                19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gaagaaaauu uccgcaaaa                                                19

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
gaagaaaauu uccgcaaaa                                                19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uuuugcggaa auuuucuuc                                                19

<210> SEQ ID NO 187
<211> LENGTH: 19
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 187
uuuugcggaa auuucuuc                                                19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uuuugcggaa auuucuuc                                                19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
uuuugcggaa auuucuuc                                                19

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
gaagaaaauu uccgcaaaa                                               19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
gaagaaaauu uccgcaaaa                                               19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
gaagaaaauu uccgcaaaa                                               19

<210> SEQ ID NO 193

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
gaagaaaauu uccgcaaaa                                              19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
gaagaaaauu uccgcaaaa                                              19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gaagaaaauu uccgcaaaa                                              19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gaagaaaauu uccgcaaaa                                              19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gaagaaaauu uccgcaaaa                                              19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uuuugcggaa auuuucuuc                                              19
```

```
<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uuuugcggaa auuucuuc                                                    19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uuuugcggaa auuucuuc                                                    19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uuuugcggaa auuucuuc                                                    19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uuuugcggaa auuucuuc                                                    19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uuuugcggaa auuucuuc                                                    19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uuuugcggaa auuucuuc                                                    19
```

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uuuugcggaa auuuucuuc                                                  19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
agggcgucau ccaacacaa                                                  19

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
acccccucau ccaacacaa                                                  19

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
acccccucau ccaacacaa                                                  19

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
acccccucau ccaacacaa                                                  19

<210> SEQ ID NO 210
<211> LENGTH: 19

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
acccccucau ccaacacaa                                                      19

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
acccccucau ccaacacaat ttt                                                 23

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
acccccucau ccaacacaa                                                      19

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
acccccucau ccaacacaat ttt                                                 23

<210> SEQ ID NO 214
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
acccccucau ccaacacaa                                                      19

<210> SEQ ID NO 215
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
accccaucau ccaacacaa                                                    19

<210> SEQ ID NO 216
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
accccaucau ccaacacaa                                                    19

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
accccaucau ccaacacaa                                                    19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
accccaucau ccaacacaa                                                    19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
uuguguugga ugacgccutt                                                   20

<210> SEQ ID NO 220
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
uucucuucca ucaccccut ttt                                              23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
uucucuucca ucaccccut ttt                                              23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
uucucuucca ucaccccut ttt                                              23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
uucucuucca ucaccccut ttt                                              23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
uucucuucca ucaccccut ttt                                              23

<210> SEQ ID NO 225
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
uucucuucca ucacccccut ttt                                          23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
tucucuucca ucacccccut ttt                                          23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
tucucuucca ucacccccut ttt                                          23

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
tucucuucca ucacccccut ttt                                          23

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
tucucuucca ucacccccut ttt                                          23

<210> SEQ ID NO 230
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
tucucuucca ucacccccut ttt                                              23

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
tucucuucca ucacccccut ttt                                              23
```